(12) United States Patent
Gonzalez-Zugasti et al.

(10) Patent No.: US 10,799,166 B2
(45) Date of Patent: *Oct. 13, 2020

(54) DELIVERING AND/OR RECEIVING FLUIDS

(71) Applicant: Seventh Sense Biosystems, Inc., Medford, MA (US)

(72) Inventors: Javier Gonzalez-Zugasti, North Billerica, MA (US); A. David Boccuti, Arlington, MA (US); Donald E. Chickering, III, Framingham, MA (US); Mark Michelman, Reading, MA (US); Ramin Haghgooie, Arlington, MA (US); Shawn Davis, Santa Monica, CA (US); Scott James, Epping, NH (US); Maisam Dadgar, Cambridge, MA (US); Greg Fisher, Boston, MA (US); Richard L. Miller, Needham, MA (US); Christopher J. Morse, Malden, MA (US); Howard Bernstein, Cambridge, MA (US); Douglas A. Levinson, Sherborn, MA (US)

(73) Assignee: Seventh Sense Biosystems, Inc., Medford, MA (US)

( * ) Notice: Subject to any disclaimer, the term of this patent is extended or adjusted under 35 U.S.C. 154(b) by 224 days.

This patent is subject to a terminal disclaimer.

(21) Appl. No.: 15/634,354

(22) Filed: Jun. 27, 2017

(65) Prior Publication Data

US 2018/0132774 A1 May 17, 2018
US 2018/0317829 A9 Nov. 8, 2018

Related U.S. Application Data

(63) Continuation of application No. 14/328,892, filed on Jul. 11, 2014, now Pat. No. 9,730,624, which is a
(Continued)

(51) Int. Cl.
*A61B 5/00* (2006.01)
*A61B 5/15* (2006.01)
(Continued)

(52) U.S. Cl.
CPC ...... *A61B 5/150374* (2013.01); *A61B 5/1411* (2013.01); *A61B 5/14546* (2013.01);
(Continued)

(58) Field of Classification Search
CPC ............... A61B 5/1405; A61B 5/1411; A61B 5/150022; A61B 5/150099; A61B 5/150374; A61B 10/0045
See application file for complete search history.

(56) References Cited

U.S. PATENT DOCUMENTS 2,735,671 A 2/1956 Kuhn
2,961,233 A 11/1960 Ullrich
(Continued)

FOREIGN PATENT DOCUMENTS

CN 2065878 U 11/1990
CN 1222334 A 7/1999
(Continued)

OTHER PUBLICATIONS

Australian Examination Report dated Sep. 4, 2017 in connection with Australian Application No. 2016266112.
(Continued)

*Primary Examiner* — Max F Hindenburg
(74) *Attorney, Agent, or Firm* — Wolf, Greenfield & Sacks, P.C.

(57) ABSTRACT

The present invention generally relates to receiving bodily fluid through a device opening. In one aspect, the device includes a flow activator arranged to cause fluid to be released from a subject. A deployment actuator may actuate the flow activator in a deployment direction, which may in
(Continued)

turn cause fluid release from a subject. The flow activator may also be moved in a retraction direction by a retraction actuator. In one aspect, the device may include a vacuum source that may help facilitate fluid flow into the opening of the device and/or may help facilitate fluid flow from the opening to a storage chamber. In one aspect, a device actuator may enable fluid communication between the opening and the vacuum source and the flow activator may be actuated after the enablement of fluid communication.

32 Claims, 49 Drawing Sheets

Related U.S. Application Data continuation of application No. 13/680,351, filed on Nov. 19, 2012, now Pat. No. 8,821,412, which is a continuation-in-part of application No. 13/456,570, filed on Apr. 26, 2012, now Pat. No. 8,827,971, which is a continuation-in-part of application No. 13/456,394, filed on Apr. 26, 2012, now Pat. No. 9,295,417, which is a continuation-in-part of application No. 13/456,505, filed on Apr. 26, 2012, now Pat. No. 9,119,578, said application No. 13/680,351 is a continuation-in-part of application No. 13/456,546, filed on Apr. 26, 2012, now abandoned, said application No. 13/680,351 is a continuation-in-part of application No. PCT/US2011/047565, filed on Aug. 12, 2011, said application No. 13/680,351 is a continuation-in-part of application No. PCT/US2011/043698, filed on Jul. 12, 2011, which is a continuation-in-part of application No. 13/166,451, filed on Jun. 22, 2011, now Pat. No. 9,033,898, which is a continuation-in-part of application No. 13/016,575, filed on Jan. 28, 2011, now Pat. No. 9,041,541, which is a continuation-in-part of application No. 13/006,165, filed on Jan. 13, 2011, now abandoned, said application No. 13/680,351 is a continuation-in-part of application No. 13/006,177, filed on Jan. 13, 2011, now abandoned, said application No. 13/680,351 is a continuation-in-part of application No. 12/953,744, filed on Nov. 24, 2010, now abandoned, said application No. 13/680,351 is a continuation-in-part of application No. 12/915,735, filed on Oct. 29, 2010, now abandoned, said application No. 13/680,351 is a continuation-in-part of application No. 12/915,789, filed on Oct. 29, 2010, now abandoned, said application No. 13/680,351 is a continuation-in-part of application No. 12/915,820, filed on Oct. 29, 2010, now abandoned, said application No. 13/680,351 is a continuation-in-part of application No. 12/716,229, filed on Mar. 2, 2010, now Pat. No. 9,113,836, said application No. 13/680,351 is a continuation-in-part of application No. 12/716,226, filed on Mar. 2, 2010, now abandoned.

(60) Provisional application No. 61/480,977, filed on Apr. 29, 2011, provisional application No. 61/480,960, filed on Apr. 29, 2011, provisional application No. 61/549,437, filed on Oct. 20, 2011, provisional application No. 61/480,941, filed on Apr. 29, 2011, provisional application No. 61/577,399, filed on Dec. 19, 2011, provisional application No. 61/373,764, filed on Aug. 13, 2010, provisional application No. 61/367,607, filed on Jul. 26, 2010, provisional application No. 61/357,582, filed on Jun. 23, 2010, provisional application No. 61/299,283, filed on Jan. 28, 2010, provisional application No. 61/334,533, filed on May 13, 2010, provisional application No. 61/334,529, filed on May 13, 2010, provisional application No. 61/294,543, filed on Jan. 13, 2010, provisional application No. 61/263,882, filed on Nov. 24, 2009, provisional application No. 61/256,880, filed on Oct. 30, 2009, provisional application No. 61/256,874, filed on Oct. 30, 2009, provisional application No. 61/256,871, filed on Oct. 30, 2009, provisional application No. 61/256,863, filed on Oct. 30, 2009, provisional application No. 61/256,910, filed on Oct. 30, 2009, provisional application No. 61/256,931, filed on Oct. 30, 2009, provisional application No. 61/256,933, filed on Oct. 30, 2009, provisional application No. 61/257,731, filed on Nov. 3, 2009, provisional application No. 61/269,436, filed on Jun. 24, 2009, provisional application No. 61/168,710, filed on Mar. 26, 2009, provisional application No. 61/156,632, filed on Mar. 2, 2009, provisional application No. 61/294,543, filed on Jan. 13, 2010.

(51) Int. Cl.
*A61B 5/151* (2006.01)
*A61B 10/00* (2006.01)
*A61B 5/145* (2006.01)
*A61M 37/00* (2006.01)
*G16H 10/40* (2018.01)
*G06F 19/00* (2018.01)
*A61B 5/154* (2006.01)
*A61B 5/1459* (2006.01)
*A61B 5/1486* (2006.01)

(52) U.S. Cl.
CPC .............. *A61B 5/151* (2013.01); *A61B 5/154* (2013.01); *A61B 5/150022* (2013.01); *A61B 5/150099* (2013.01); *A61B 5/15113* (2013.01); *A61B 5/15117* (2013.01); *A61B 5/15144* (2013.01); *A61B 5/150412* (2013.01); *A61B 5/150503* (2013.01); *A61B 5/150969* (2013.01); *A61B 5/150977* (2013.01); *A61B 5/150984* (2013.01); *A61B 5/411* (2013.01); *A61B 5/685* (2013.01); *A61B 10/0045* (2013.01); *A61M 37/0015* (2013.01); *G06F 19/00* (2013.01); *G16H 10/40* (2018.01); *A61B 5/1459* (2013.01); *A61B 5/14532* (2013.01); *A61B 5/14539* (2013.01); *A61B 5/14865* (2013.01); *A61B 5/150221* (2013.01); *A61B 5/150358* (2013.01); *A61B 5/150755* (2013.01); *A61B 10/007* (2013.01); *A61B 10/0051* (2013.01); *A61B 2010/008* (2013.01)

(56) References Cited

U.S. PATENT DOCUMENTS

| | | |
|---|---|---|
| 2,976,735 A | 3/1961 | Witte |
| 3,060,429 A | 10/1962 | Winston |
| 3,072,122 A | 1/1963 | Rosenthall |
| 3,339,546 A | 9/1967 | Chen |
| 3,519,171 A | 7/1970 | Kinnavy |
| 3,551,554 A | 12/1970 | Herschler |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,908,657 A | 9/1975 | Kowarski |

(56) References Cited

U.S. PATENT DOCUMENTS

| | | |
|---|---|---|
| 3,964,482 A | 6/1976 | Gerstel et al. |
| 4,103,684 A | 8/1978 | Ismach |
| 4,150,744 A | 4/1979 | Fennimore |
| 4,253,460 A | 3/1981 | Chen et al. |
| 4,280,509 A | 7/1981 | Bethkenhagen et al. |
| 4,329,999 A | 5/1982 | Phillips |
| 4,340,067 A * | 7/1982 | Rattenborg ........ A61B 5/15003 600/576 |
| 4,537,776 A | 8/1985 | Cooper |
| 4,553,552 A | 11/1985 | Valdespino et al. |
| 4,557,943 A | 12/1985 | Rosler et al. |
| 4,572,210 A * | 2/1986 | McKinnon .......... A61M 5/3145 600/578 |
| 4,615,697 A | 10/1986 | Robinson |
| 4,621,268 A | 11/1986 | Keeling et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,856,533 A | 8/1989 | Anraku et al. |
| 4,863,970 A | 9/1989 | Patel et al. |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,014,718 A | 5/1991 | Mitchen |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,145,565 A | 9/1992 | Kater et al. |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,238,655 A | 8/1993 | Laible et al. |
| 5,279,294 A | 1/1994 | Anderson et al. |
| 5,320,607 A | 6/1994 | Ishibashi |
| 5,402,798 A | 4/1995 | Swierczek et al. |
| 5,415,177 A | 5/1995 | Zadini et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D' Angelo et al. |
| 5,445,611 A | 8/1995 | Eppstein et al. |
| 5,458,140 A | 10/1995 | Eppstein et al. |
| 5,504,011 A | 4/1996 | Gavin et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,701,910 A | 12/1997 | Powles et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,897,508 A | 4/1999 | Konrad |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,972,386 A | 10/1999 | Burgoyne |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,024,710 A | 2/2000 | Miller et al. |
| 6,027,459 A | 2/2000 | Shain et al. |
| 6,040,135 A | 3/2000 | Tyrell |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,133,318 A | 10/2000 | Hart |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,261,245 B1 | 7/2001 | Kawai et al. |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,319,210 B1 | 11/2001 | Douglas et al. |
| 6,322,574 B1 | 11/2001 | Llyod |

(56) References Cited

U.S. PATENT DOCUMENTS

| | | |
|---|---|---|
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,317 B1 | 4/2002 | Kintzig et al. |
| 6,379,324 B1 | 4/2002 | Gartstein et al. |
| 6,391,471 B1 | 5/2002 | Hiraoka et al. |
| 6,406,919 B1 | 6/2002 | Tyrrell |
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,925,317 B1 | 8/2005 | Samuels et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,351 B2 | 11/2005 | Knoll |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,025,774 B2 | 4/2006 | Freeman et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,131,987 B2 | 11/2006 | Sherman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,172,071 B2 | 2/2007 | Hawkins |
| 7,174,199 B2 | 2/2007 | Berner et al. |
| 7,182,910 B2 | 2/2007 | Allen et al. |
| 7,185,764 B2 | 3/2007 | Lee et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 | 1/2008 | Lastovich et al. |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,556,615 B2 | 7/2009 | Pettis et al. |
| 7,572,237 B2 | 8/2009 | Saikley et al. |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,236 B2 | 10/2010 | List et al. |
| 7,811,302 B2 | 10/2010 | Steg |
| 7,833,172 B2 | 11/2010 | Hein et al. |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,058,077 B2 | 11/2011 | Groll et al. |
| 8,071,384 B2 | 12/2011 | Burke et al. |
| 8,075,826 B2 | 12/2011 | Lastovich et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,344,028 B2 | 1/2013 | Xu et al. |

(56) References Cited

U.S. PATENT DOCUMENTS

| | | | |
|---|---|---|---|
| 8,383,044 B2 | 2/2013 | Davis et al. | |
| 8,465,425 B2 | 6/2013 | Heller et al. | |
| 8,523,894 B2 | 9/2013 | Schmelzeisen-Redeker et al. | |
| 8,561,795 B2 | 10/2013 | Schott | |
| 8,808,202 B2 | 8/2014 | Brancazio | |
| 8,821,412 B2 * | 9/2014 | Gonzalez-Zugasti | A61B 5/1411 600/583 |
| 8,821,446 B2 | 9/2014 | Trautman et al. | |
| 8,827,971 B2 | 9/2014 | Chickering, III et al. | |
| 8,870,903 B2 * | 10/2014 | LeVaughn | A61B 5/1411 604/218 |
| 8,882,794 B2 * | 11/2014 | Lum | A61B 5/1411 606/181 |
| 8,900,180 B2 | 12/2014 | Wolter et al. | |
| 8,934,955 B2 | 1/2015 | Schraga | |
| 8,971,980 B2 | 3/2015 | Mace et al. | |
| 9,028,426 B2 | 5/2015 | List et al. | |
| 9,033,898 B2 | 5/2015 | Chickering, III et al. | |
| 9,033,989 B2 * | 5/2015 | Wolfson | A61B 17/155 606/87 |
| 9,039,638 B2 | 5/2015 | Arnitz | |
| 9,041,541 B2 * | 5/2015 | Levinson | G06F 19/3456 340/573.1 |
| 9,101,302 B2 | 8/2015 | Mace et al. | |
| 9,113,836 B2 | 8/2015 | Bernstein et al. | |
| 9,119,578 B2 * | 9/2015 | Haghgooie | A61B 5/1411 |
| 9,295,417 B2 * | 3/2016 | Haghgooie | A61B 5/1411 |
| 9,730,624 B2 * | 8/2017 | Gonzalez-Zugasti | A61B 5/1411 |
| 9,775,551 B2 | 10/2017 | Bernstein et al. | |
| 10,188,335 B2 | 1/2019 | Haghgooie et al. | |
| 10,543,310 B2 | 1/2020 | Bernstein et al. | |
| 2001/0005772 A1 | 6/2001 | Kisakibaru | |
| 2002/0010414 A1 | 1/2002 | Coston et al. | |
| 2002/0013538 A1 | 1/2002 | Teller | |
| 2002/0065453 A1 | 5/2002 | Lesho et al. | |
| 2002/0076443 A1 | 6/2002 | Stein et al. | |
| 2002/0077584 A1 | 6/2002 | Lin et al. | |
| 2002/0082543 A1 | 6/2002 | Park et al. | |
| 2002/0099308 A1 | 7/2002 | Bojan et al. | |
| 2002/0099356 A1 | 7/2002 | Unger et al. | |
| 2002/0112981 A1 | 8/2002 | Cooper et al. | |
| 2002/0115967 A1 | 8/2002 | Svedman | |
| 2002/0119136 A1 | 8/2002 | Johansen | |
| 2002/0130042 A1 | 9/2002 | Moerman et al. | |
| 2002/0130093 A1 | 9/2002 | Ferrara et al. | |
| 2002/0138049 A1 | 9/2002 | Allen | |
| 2002/0143320 A1 | 10/2002 | Levin | |
| 2002/0168290 A1 | 11/2002 | Yuzhakov et al. | |
| 2002/0169393 A1 | 11/2002 | Cunningham et al. | |
| 2002/0169394 A1 | 11/2002 | Eppstein et al. | |
| 2002/0169411 A1 | 11/2002 | Sherman et al. | |
| 2002/0177761 A1 | 11/2002 | Orloff et al. | |
| 2002/0187556 A1 | 12/2002 | Shartle et al. | |
| 2002/0188221 A1 | 12/2002 | Sohrab | |
| 2003/0004437 A1 | 1/2003 | Collins et al. | |
| 2003/0040682 A1 | 2/2003 | Tapper | |
| 2003/0055326 A1 | 3/2003 | Sohrab | |
| 2003/0083618 A1 | 5/2003 | Angel et al. | |
| 2003/0083645 A1 | 5/2003 | Angel et al. | |
| 2003/0083685 A1 | 5/2003 | Freeman et al. | |
| 2003/0100846 A1 | 5/2003 | Custer et al. | |
| 2003/0109807 A1 | 6/2003 | Knoll | |
| 2003/0113540 A1 | 6/2003 | Anderson et al. | |
| 2003/0135158 A1 | 7/2003 | Gonnelli | |
| 2003/0135167 A1 | 7/2003 | Gonnelli | |
| 2003/0135201 A1 | 7/2003 | Gonnelli | |
| 2003/0135333 A1 | 7/2003 | Aceti et al. | |
| 2003/0143746 A1 | 7/2003 | Sage | |
| 2003/0159615 A1 | 8/2003 | Anderson et al. | |
| 2003/0162304 A1 | 8/2003 | Dority et al. | |
| 2003/0181863 A1 | 9/2003 | Ackley et al. | |
| 2003/0187394 A1 | 10/2003 | Wilkinson et al. | |
| 2003/0187395 A1 | 10/2003 | Gabel et al. | |
| 2003/0195398 A1 | 10/2003 | Suzuki et al. | |
| 2003/0204148 A1 | 10/2003 | Lange et al. | |
| 2003/0208138 A1 | 11/2003 | Olson | |
| 2003/0212344 A1 | 11/2003 | Yuzhakov et al. | |
| 2003/0212345 A1 | 11/2003 | McAllister et al. | |
| 2003/0212347 A1 | 11/2003 | Sohrab | |
| 2003/0212423 A1 | 11/2003 | Pugh et al. | |
| 2003/0228367 A1 | 12/2003 | Mathiowitz et al. | |
| 2004/0010207 A1 | 1/2004 | Flaherty et al. | |
| 2004/0053894 A1 | 3/2004 | Mazess et al. | |
| 2004/0058458 A1 | 3/2004 | Anker et al. | |
| 2004/0087990 A1 | 5/2004 | Boecker et al. | |
| 2004/0096959 A1 | 5/2004 | Stiene et al. | |
| 2004/0098009 A1 | 5/2004 | Boecker et al. | |
| 2004/0102717 A1 | 5/2004 | Qi | |
| 2004/0106904 A1 | 6/2004 | Gonnelli et al. | |
| 2004/0133126 A1 | 7/2004 | McNenny | |
| 2004/0137640 A1 | 7/2004 | Hirao et al. | |
| 2004/0138688 A1 | 7/2004 | Giraud | |
| 2004/0162521 A1 | 8/2004 | Bengtsson | |
| 2004/0171980 A1 | 9/2004 | Mitragotri et al. | |
| 2004/0199103 A1 | 10/2004 | Kwon | |
| 2004/0204744 A1 | 10/2004 | Penner et al. | |
| 2004/0236250 A1 | 11/2004 | Hodges et al. | |
| 2004/0247016 A1 | 12/2004 | Faries et al. | |
| 2004/0249310 A1 | 12/2004 | Shartle et al. | |
| 2004/0253185 A1 | 12/2004 | Herweck et al. | |
| 2005/0015055 A1 | 1/2005 | Yang | |
| 2005/0019902 A1 | 1/2005 | Mathies et al. | |
| 2005/0027176 A1 | 2/2005 | Xie | |
| 2005/0027308 A1 | 2/2005 | Davis et al. | |
| 2005/0033197 A1 | 2/2005 | Cottler | |
| 2005/0038669 A1 | 2/2005 | Sachdeva et al. | |
| 2005/0054907 A1 | 3/2005 | Page et al. | |
| 2005/0064529 A1 | 3/2005 | Kwon | |
| 2005/0069925 A1 | 3/2005 | Ford et al. | |
| 2005/0070819 A1 | 3/2005 | Poux et al. | |
| 2005/0085838 A1 | 4/2005 | Thompson et al. | |
| 2005/0106066 A1 | 5/2005 | Saltsman et al. | |
| 2005/0106713 A1 | 5/2005 | Phan et al. | |
| 2005/0137481 A1 | 6/2005 | Sheard et al. | |
| 2005/0137531 A1 | 6/2005 | Prausnitz et al. | |
| 2005/0137536 A1 | 6/2005 | Gonnelli | |
| 2005/0172852 A1 | 8/2005 | Anderson et al. | |
| 2005/0182307 A1 | 8/2005 | Currie et al. | |
| 2005/0196747 A1 | 9/2005 | Stiene | |
| 2005/0201974 A1 | 9/2005 | Schestopol et al. | |
| 2005/0203360 A1 | 9/2005 | Brauker et al. | |
| 2005/0215923 A1 | 9/2005 | Wiegel | |
| 2005/0221276 A1 | 10/2005 | Rozakis et al. | |
| 2005/0227269 A1 | 10/2005 | Lloyd, Jr. et al. | |
| 2005/0228313 A1 | 10/2005 | Kaler et al. | |
| 2005/0245844 A1 | 11/2005 | Mace et al. | |
| 2005/0249672 A1 | 11/2005 | Bolbot | |
| 2005/0251152 A1 | 11/2005 | Herweck et al. | |
| 2005/0261632 A1 | 11/2005 | Xu | |
| 2005/0261639 A1 | 11/2005 | Herweck | |
| 2005/0267422 A1 | 12/2005 | Kriesel | |
| 2006/0001551 A1 | 1/2006 | Kraft et al. | |
| 2006/0004271 A1 | 1/2006 | Peyser et al. | |
| 2006/0004303 A1 | 1/2006 | Weidenhaupt et al. | |
| 2006/0030790 A1 | 2/2006 | Braig et al. | |
| 2006/0036187 A1 | 2/2006 | Vos et al. | |
| 2006/0058602 A1 | 3/2006 | Kwiatkowski et al. | |
| 2006/0089566 A1 | 4/2006 | DeHart | |
| 2006/0100654 A1 | 5/2006 | Fukuda et al. | |
| 2006/0129065 A1 | 6/2006 | Matsumoto et al. | |
| 2006/0142651 A1 | 6/2006 | Brister et al. | |
| 2006/0157362 A1 * | 7/2006 | Schraga | A61B 5/1411 206/363 |
| 2006/0182738 A1 | 8/2006 | Holmes et al. | |
| 2006/0189895 A1 | 8/2006 | Neel et al. | |
| 2006/0200046 A1 | 9/2006 | Windus-Smith et al. | |
| 2006/0202385 A1 | 9/2006 | Xu et al. | |
| 2006/0228259 A1 | 10/2006 | Samsoondar | |
| 2006/0257883 A1 | 11/2006 | Bjorkaker et al. | |
| 2006/0264779 A1 | 11/2006 | Kemp et al. | |
| 2006/0264782 A1 | 11/2006 | Holmes et al. | |

(56) References Cited

U.S. PATENT DOCUMENTS

| | | |
|---|---|---|
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0083131 A1 | 4/2007 | Escutia et al. |
| 2007/0088248 A1 | 4/2007 | Glenn et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161964 A1 | 7/2007 | Yukhazov |
| 2007/0167340 A1 | 7/2007 | Barthel et al. |
| 2007/0169411 A1 | 7/2007 | Thiessen et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0185515 A1 | 8/2007 | Stout |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2007/0275193 A1 | 11/2007 | DeSimone et al. |
| 2008/0009763 A1 | 1/2008 | Chiou et al. |
| 2008/0014627 A1 | 1/2008 | Merchant et al. |
| 2008/0021491 A1 | 1/2008 | Freeman et al. |
| 2008/0033319 A1 | 2/2008 | Kloepfer et al. |
| 2008/0051689 A1 | 2/2008 | Gura et al. |
| 2008/0077096 A1 | 3/2008 | Nakamura et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0103434 A1 | 5/2008 | Lastovich et al. |
| 2008/0108959 A1 | 5/2008 | Jung et al. |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelmann et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183140 A1 | 7/2008 | Paproski et al. |
| 2008/0183144 A1 | 7/2008 | Trautmann et al. |
| 2008/0200791 A1 | 8/2008 | Simpson et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0275378 A1 | 11/2008 | Herndon |
| 2008/0281290 A1 | 11/2008 | Yodfat et al. |
| 2008/0300508 A1 | 12/2008 | Tomer |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0054813 A1 | 2/2009 | Freeman et al. |
| 2009/0054971 A1 | 2/2009 | Mitsunaga et al. |
| 2009/0076453 A1 | 3/2009 | Mejlhede et al. |
| 2009/0099427 A1 | 4/2009 | Jina et al. |
| 2009/0099478 A1 | 4/2009 | Cassells et al. |
| 2009/0099529 A1 | 4/2009 | Anderson et al. |
| 2009/0105614 A1 | 4/2009 | Momose et al. |
| 2009/0118662 A1 | 5/2009 | Schnall |
| 2009/0124994 A1 | 5/2009 | Roe |
| 2009/0131829 A1 | 5/2009 | Freeman et al. |
| 2009/0182306 A1 | 7/2009 | Lee et al. |
| 2009/0187160 A1 | 7/2009 | McAllister et al. |
| 2009/0187167 A1 | 7/2009 | Sexton et al. |
| 2009/0198189 A1 | 8/2009 | Simons et al. |
| 2009/0198215 A1 | 8/2009 | Chong et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0021947 A1 | 1/2010 | Emery et al. |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0114014 A1 | 5/2010 | Roser |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0240079 A1 | 9/2010 | Jackson |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0292191 A1 | 11/2010 | Mainx et al. |
| 2010/0318111 A1 | 12/2010 | Sarna et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0034830 A1 | 2/2011 | Nakamura et al. |
| 2011/0040208 A1 | 2/2011 | Mcminn et al. |
| 2011/0040317 A1 | 2/2011 | Lee et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0112384 A1 | 5/2011 | Eisenhardt et al. |
| 2011/0112438 A1 | 5/2011 | Radzuinas et al. |
| 2011/0125058 A1 | 5/2011 | Levinson et al. |
| 2011/0137203 A1 | 6/2011 | Nishiuchi et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0282173 A1 | 11/2011 | Fonduca et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0089050 A1 | 4/2012 | Fukuda |
| 2012/0123297 A1 | 5/2012 | Brancazio |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |

(56) References Cited

U.S. PATENT DOCUMENTS

| | | |
|---|---|---|
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0278476 A1 | 10/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2016/0262676 A1 | 9/2016 | Haghgooie et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0023473 A1 | 1/2019 | Schott |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0336058 A1 | 11/2019 | Haghgooie et al. |
| 2020/0015751 A9 | 1/2020 | Chickering et al. |

FOREIGN PATENT DOCUMENTS

| | | |
|---|---|---|
| CN | 2331315 Y | 8/1999 |
| CN | 2462854 Y | 12/2001 |
| CN | 2600055 Y | 1/2004 |
| CN | 1499949 A | 5/2004 |
| CN | 1501788 A | 6/2004 |
| CN | 1524493 A | 9/2004 |
| CN | 1551743 A | 12/2004 |
| CN | 1753646 A | 3/2006 |
| CN | 101248998 A | 8/2008 |
| CN | 101347384 A | 1/2009 |
| CN | 101678196 A | 3/2010 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 535 266 A1 | 4/1993 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 027 864 A1 | 8/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 2 064 993 A1 | 6/2009 |
| EP | 2 077 128 A1 | 7/2009 |
| EP | 1 187 653 B1 | 3/2010 |
| EP | 2 701 601 A1 | 3/2014 |
| FR | 2929135 A1 | 10/2009 |
| GB | 2153223 A | 8/1985 |
| JP | 61-198061 A2 | 9/1986 |
| JP | 03-060645 A2 | 3/1991 |
| JP | 4-053536 A2 | 2/1992 |
| JP | 5-63506 A | 8/1993 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-517463 A | 6/2005 |
| JP | 2005-522243 | 7/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-280912 A | 10/2006 |
| JP | 2007-209549 A | 8/2007 |
| JP | 2007-236686 | 9/2007 |
| JP | 2007-526460 A | 9/2007 |
| JP | 2008-022988 A | 2/2008 |
| JP | 2008-54884 A | 3/2008 |
| JP | 2008-079853 A | 4/2008 |
| JP | 2008-099988 A | 5/2008 |
| JP | 2008-099992 A | 5/2008 |
| JP | 2008-518662 A | 6/2008 |
| JP | 2008-534192 A | 8/2008 |
| JP | 2009-509679 A | 3/2009 |
| JP | 2009-066385 A | 4/2009 |
| JP | 2009-078173 A | 4/2009 |
| JP | 2009-519064 A | 5/2009 |
| JP | 2009-254899 A2 | 8/2009 |
| JP | 2010-520036 A | 6/2010 |
| JP | 2011-511660 A | 4/2011 |
| JP | 2011-522593 A | 8/2011 |
| WO | WO 1992/002175 A1 | 2/1992 |
| WO | WO 1992/004867 A1 | 4/1992 |
| WO | WO 1993/000043 A1 | 1/1993 |
| WO | WO 1995/010223 A2 | 4/1995 |
| WO | WO 1995/015783 A1 | 6/1995 |
| WO | WO 1997/008987 A1 | 3/1997 |
| WO | WO 1997/010745 A1 | 3/1997 |
| WO | WO 1997/034587 A2 | 9/1997 |
| WO | WO 1997/048442 A1 | 12/1997 |
| WO | WO 1998/024366 A2 | 6/1998 |
| WO | WO 1999/027852 A1 | 6/1999 |
| WO | WO 1999/059657 A1 | 11/1999 |
| WO | WO 2000/035357 A1 | 6/2000 |
| WO | WO 2000/035530 A1 | 6/2000 |
| WO | WO 2000/074763 A2 | 12/2000 |
| WO | WO 2001/043643 A1 | 6/2001 |
| WO | WO 2001/093946 A1 | 12/2001 |
| WO | WO 2002/000101 A2 | 1/2002 |
| WO | WO 2002/005890 A2 | 1/2002 |
| WO | WO 2002/030301 A1 | 4/2002 |
| WO | WO 2002/030506 A2 | 4/2002 |
| WO | WO 2002/078533 A2 | 10/2002 |
| WO | WO 2002/091922 A1 | 11/2002 |
| WO | WO 2002/100253 A2 | 12/2002 |
| WO | WO 2002/100460 A2 | 12/2002 |
| WO | WO 2002/101359 A2 | 12/2002 |
| WO | WO 2003/020134 A2 | 3/2003 |
| WO | WO 2003/026611 A2 | 4/2003 |
| WO | WO 2003/030984 A2 | 4/2003 |
| WO | WO 2003/037403 A1 | 5/2003 |
| WO | WO 2003/039632 A2 | 5/2003 |
| WO | WO 03/070099 A1 | 8/2003 |
| WO | WO 2003/082091 A2 | 10/2003 |
| WO | WO 2003/083469 A2 | 10/2003 |
| WO | WO 2003/088851 A1 | 10/2003 |
| WO | WO 2003/099123 A2 | 12/2003 |
| WO | WO 2004/006982 A3 | 1/2004 |
| WO | WO 2004/022133 A2 | 3/2004 |

(56) References Cited

FOREIGN PATENT DOCUMENTS

| | | |
|---|---|---|
| WO | WO 2005/000118 A1 | 1/2005 |
| WO | WO 2005/025413 A2 | 3/2005 |
| WO | WO 2005/084534 A1 | 9/2005 |
| WO | WO 2005/095965 A1 | 10/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/050032 A2 | 5/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A1 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/079530 A1 | 7/2007 |
| WO | WO 2007/091671 A1 | 8/2007 |
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/004627 A3 | 1/2009 |
| WO | WO 2009/008267 A1 | 1/2009 |
| WO | WO 2009/011138 A1 | 1/2009 |
| WO | WO 2009/027950 A2 | 3/2009 |
| WO | WO 2009/055693 A2 | 4/2009 |
| WO | WO 2009/071775 A1 | 6/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/148624 A1 | 12/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | WO 2012/149134 A1 | 11/2012 |
| WO | WO 2014/160893 A2 | 10/2014 |

OTHER PUBLICATIONS

Australian Examination Report dated Feb. 1, 2019 in connection with Australian Application No. 2018223046.
Australian Examination Report dated Dec. 20, 2019 in connection with Australian Application No. 2018223046.
Notice of Acceptance dated Jan. 15, 2020 in connection with Australian Application No. 2018223046.
Brazilian Office Action dated Dec. 24, 2019 in connection with Brazilian Application No. BR1120130273518.
Canadian Examiner's Report dated Jan. 29, 2018 in connection with Canadian Application No. 2,833,275.
Canadian Examiner's Report dated Jan. 24, 2019 in connection with Canadian Application No. 2,833,275.
Chinese Office Action dated Mar. 24, 2015 for Application No. 201280021297.9.
European Intention to Grant dated Apr. 16, 2018 in connection with European Application No. 16162360.8.
European Notice of Opposition mailed Jul. 2, 2019 in connection with EP 16162360.8.
European Office Action dated Jun. 30, 2015 for Application No. 12721066.4.
Extended European Search Report for Application No. EP 16162360.8 dated Sep. 13, 2016.
International Preliminary Report on Patentability for PCT/US2012/035191 dated Nov. 7, 2013.
International Search Report and Written Opinion dated Oct. 4, 2012 in connection with PCT/US2012/035191.
Invitation to Pay Additional Fees dated Aug. 17, 2012 in connection with PCT/US2012/035191.
Japanese Office Action dated Mar. 12, 2018 in connection with Japanese Application No. 2017-65121.
Japanese Office Action dated Apr. 12, 2016 for Application No. 2014-508548.
Korean Office Action dated Dec. 9, 2019 in connection with Korean Application No. 10-2019-7023871.
[No Author Listed] Air-Tite Products Co., Inc.—Luer Lock. Oct. 14, 2008. Retrieved from the Internet: https://web.archive.org/web/20081023203858/https://www.air-tite-shop.com/c-7-luer-lock.aspx on Aug. 28, 2019. 2 pages.
[No Author Listed] Greiner Bio-One Preanalytics Catalogue. www.gbo.com/preanalytics. Feb. 2012. 76 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
[No Author Listed] Sof-Tact Manual. Date Unknown. 57 pages. (After reasonable inquiry, the undersigned believes this manual was available beginning 2001, but cannot determine the exact date of this publication. The year of publication is sufficiently earlier than the effective U.S. filing date and priority date so that the particular month and year of publication is not in issue. See MPEP 609.04(a).)
[No Author Listed], Whatman Neonatal Screening Cards—Capabilities. GE Healthcare. Dec. 2009; 12 pages. www.gelifesciences.com/whatman.
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption—Mechanisms—Methodology. Bronaugh et al., eds. Marcell Dekker. 1989;3-12. (The year of publication is sufficiently earlier than the effective U.S. filing date and any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Fuhrer et al., Building a Smart Hospital using RFID technologies: Use Cases and Implementation. 2006; 14 pages.

(56) References Cited

OTHER PUBLICATIONS

Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Matriano et al., Macroflux microprojection array patch technology: a new and efficient approach for intracutaneous immunization. Pharm Res. Jan. 2002;19(1):63-70.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.
McShane, Microcapsules as 'smart tattoo' glucose sensors: engineering systems with enzymes and glucose-binding sensing elements, *Top Fluor. Spec.*, 2006, vol. 11, *Glc. Sens.*, p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transdermal Drug Delivery by Application of Ultrasound. In: Encl. of Pharm. Tech., vol. 14, Swarbrick, J., Boylan, J., (Eds.), vol. 14, 103-122, 1996. (After reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95. (The year of publication is sufficiently earlier than the effective U.S. filing date and any foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1):155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.
U.S. Appl. No. 15/916,330, filed Mar. 9, 2018, Davis et al.
U.S. Appl. No. 15/828,908, filed Dec. 1, 2017, Chickering et al.
U.S. Appl. No. 15/387,459, filed Dec. 21, 2016, Levinson et al.
U.S. Appl. No. 15/285,034, filed Oct. 4, 2016, Levinson et al.
U.S. Appl. No. 15/899,613, filed Feb. 20, 2018, Schott.
U.S. Appl. No. 16/048,722, filed Jul. 30, 2018, Chickering et al.
U.S. Appl. No. 15/290,217, filed Oct. 11, 2016, Levinson et al.
U.S. Appl. No. 15/297,253, filed Oct. 19, 2016, Brancazio.
U.S. Appl. No. 15/693,666, filed Sep. 1, 2017, Chickering et al.
U.S. Appl. No. 14/987,973, filed Jan. 5, 2016, Haghgooie et al.
U.S. Appl. No. 16/218,441, filed Dec. 12, 2018, Haghgooie et al.
U.S. Appl. No. 16/705,286, filed Dec. 11, 2019, Bernstein et al.
U.S. Appl. No. 15/156,386, filed May 17, 2016, Bernstein et al.
U.S. Appl. No. 16/321,123, filed Jan. 28, 2019, Barone et al.
AU 2016266112, Sep. 4, 2017, Australian Examination Report.
AU 2018223046, Feb. 1, 2019, Australian Examination Report.
AU 2018223046, Dec. 20, 2019, Australian Exam Report.
AU 2018223046, Jan. 15, 2020, Notice of Acceptance.
BR 1120130273518, Dec. 24, 2019, Brazilian Office Action.
CA 2,833,275, Jan. 29, 2018, Canadian Examiner's Report.
CA 2,833,275, Jan. 24, 2019, Canadian Examiner's Report.
CN 201280021297.9, Mar. 24, 2015, Chinese Office Action.
EP 12721066.4, Jun. 30, 2015, European Office Action.
EP 16162360.8, Sep. 13, 2016, Extended European Search Report.
EP 16162360.8, Sep. 16, 2018, European Intention to Grant.
16162360.8, Jul. 2, 2019, Notice of Opposition.
JP 2014-508548, Apr. 12, 2016, Japanese Office Action.
JP 2017-65121, Mar. 12, 2018, Japanese Office Action.
JP 2017-65121, Feb. 20, 2019, Japanese Office Action.
KR 10-2013-7031309, May 21, 2019, Notice of Allowance.
KR 10-2019-7023871, Dec. 9, 2019, Korean Office Action.
PCT/US2012/035191, Aug. 17, 2012, Invitation to Pay Additional Fees.
PCT/US2012/035191, Oct. 4, 2012, International Search Report and Written Opinion.
PCT/US2012/035191, Nov. 7, 2013, International Preliminary Report on Patentability.

\* cited by examiner

DELIVERING AND/OR RECEIVING FLUIDS

RELATED APPLICATIONS

This application is a continuation of U.S. patent application Ser. No. 14/328,892, filed Jul. 11, 2014, which is a continuation of U.S. patent application Ser. No. 13/680,351, filed Nov. 19, 2012, which is a continuation-in-part of U.S. patent application Ser. No. 12/716,229, filed Mar. 2, 2010, which claims the benefit of U.S. Provisional Patent Application Ser. No. 61/156,632, filed Mar. 2, 2010; U.S. Provisional Patent Application Ser. No. 61/163,710, filed Mar. 26, 2009; U.S. Provisional Patent Application Ser. No. 61/269,436, filed Jun. 24, 2009; U.S. Provisional Patent Application Ser. No. 61/257,731, filed Nov. 3, 2009; and U.S. Provisional Patent Application Ser. No. 61/294,543, filed Jan. 13, 2010.

U.S. patent application Ser. No. 13/680,351 is also a continuation-in-part of U.S. patent application Ser. No. 12/716,226, filed Mar. 2, 2010, which claims the benefit of U.S. Provisional Patent Application Ser. No. 61/156,632, filed Mar. 2, 2009; U.S. Provisional Patent Application Ser. No. 61/163,710, filed Mar. 26, 2009; U.S. Provisional Patent Application Ser. No. 61/269,436, filed Jun. 24, 2009; U.S. Provisional Patent Application Ser. No. 61/257,731, filed Nov. 3, 2009; and U.S. Provisional Patent Application Ser. No. 61/294,543, filed Jan. 13, 2010.

U.S. patent application Ser. No. 13/680,351 is also a continuation-in-part of U.S. patent application Ser. No. 12/915,735, filed Oct. 29, 2010, which claims the benefit of U.S. Provisional Patent Application Ser. No. 61/256,880, filed Oct. 30, 2009; U.S. Provisional Patent Application Ser. No. 61/256,874, filed Oct. 30, 2009; U.S. Provisional Patent Application Ser. No. 61/256,871, filed Oct. 30, 2009; U.S. Provisional Patent Application Ser. No. 61/256,863, filed Oct. 30, 2009; U.S. Provisional Patent Application Ser. No. 61/256,910, filed Oct. 30, 2009; U.S. Provisional Patent Application Ser. No. 61/256,931, filed Oct. 30, 2009; U.S. Provisional Patent Application Ser. No. 61/256,933, filed Oct. 30, 2009; U.S. Provisional Patent Application Ser. No. 61/294,543, filed Jan. 13, 2010; U.S. Provisional Patent Application Ser. No. 61/334,533, filed May 13, 2010; U.S. Provisional Patent Application Ser. No. 61/334,529, filed May 13, 2010; U.S. Provisional Patent Application Ser. No. 61/357,582, filed Jun. 23, 2010; U.S. Provisional Patent Application Ser. No. 61/367,607, filed Jul. 26, 2010; and U.S. Provisional Patent Application Ser. No. 61/373,764, filed Aug. 13, 2010.

U.S. patent application Ser. No. 13/680,351 is also a continuation-in-part of U.S. patent application Ser. No. 12/915,789, filed Oct. 29, 2010, which claims the benefit of U.S. Provisional Patent Application Ser. No. 61/256,880, filed Oct. 30, 2009; U.S. Provisional Patent Application Ser. No. 61/256,874, filed Oct. 30, 2009; U.S. Provisional Patent Application Ser. No. 61/256,871, filed Oct. 30, 2009; U.S. Provisional Patent Application Ser. No. 61/256,863, filed Oct. 30, 2009; U.S. Provisional Patent Application Ser. No. 61/256,910, filed Oct. 30, 2009; U.S. Provisional Patent Application Ser. No. 61/256,931, filed Oct. 30, 2009; U.S. Provisional Patent Application Ser. No. 61/256,933, filed Oct. 30, 2009; U.S. Provisional Patent Application Ser. No. 61/294,543, filed Jan. 13, 2010; U.S. Provisional Patent Application Ser. No. 61/334,533, filed May 13, 2010; U.S. Provisional Patent Application Ser. No. 61/334,529, filed May 13, 2010; U.S. Provisional Patent Application Ser. No. 61/357,582, filed Jun. 23, 2010; U.S. Provisional Patent Application Ser. No. 61/367,607, filed Jul. 26, 2010; and U.S. Provisional Patent Application Ser. No. 61/373,764, filed Aug. 13, 2010.

U.S. patent application Ser. No. 13/680,351 is also a continuation-in-part of U.S. patent application Ser. No. 12/915,820, filed Oct. 29, 2010, which claims the benefit of U.S. Provisional Patent Application Ser. No. 61/256,880, filed Oct. 30, 2009; U.S. Provisional Patent Application Ser. No. 61/256,874, filed Oct. 30, 2009; U.S. Provisional Patent Application Ser. No. 61/256,871, filed Oct. 30, 2009; U.S. Provisional Patent Application Ser. No. 61/256,863, filed Oct. 30, 2009; U.S. Provisional Patent Application Ser. No. 61/256,910, filed Oct. 30, 2009; U.S. Provisional Patent Application Ser. No. 61/256,931, filed Oct. 30, 2009; U.S. Provisional Patent Application Ser. No. 61/256,933, filed Oct. 30, 2009; U.S. Provisional Patent Application Ser. No. 61/294,543, filed Jan. 13, 2010; U.S. Provisional Patent Application Ser. No. 61/334,533, filed May 13, 2010; U.S. Provisional Patent Application Ser. No. 61/334,529, filed May 13, 2010; U.S. Provisional Patent Application Ser. No. 61/357,582, filed Jun. 23, 2010; U.S. Provisional Patent Application Ser. No. 61/367,607, filed Jul. 26, 2010; and U.S. Provisional Patent Application Ser. No. 61/373,764, filed Aug. 13, 2010.

U.S. patent application Ser. No. 13/680,351 is also a continuation-in-part of U.S. patent application Ser. No. 12/953,744, filed Nov. 24, 2010, which claims the benefit of U.S. Provisional Patent Application Ser. No. 61/263,882, filed Nov. 24, 2009; and U.S. Provisional Patent Application Ser. No. 61/373,764, filed Aug. 13, 2010.

U.S. patent application Ser. No. 13/680,351 is also a continuation-in-part of U.S. patent application Ser. No. 13/006,165, filed Jan. 13, 2011, which claims the benefit of U.S. Provisional Patent Application Ser. No. 61/294,543, filed Jan. 13, 2010; U.S. Provisional Patent Application Ser. No. 61/334,533, filed May 13, 2010; U.S. Provisional Patent Application Ser. No. 61/334,529, filed May 13, 2010; U.S. Provisional Patent Application Ser. No. 61/357,582, filed Jun. 23, 2010; U.S. Provisional Patent Application Ser. No. 61/367,607, filed Jul. 26, 2010; and U.S. Provisional Patent Application Ser. No. 61/373,764, filed Aug. 13, 2010.

U.S. patent application Ser. No. 13/680,351 is also a continuation-in-part of U.S. patent application Ser. No. 13/006,177, filed Jan. 13, 2011, which claims the benefit of U.S. Provisional Patent Application Ser. No. 61/294,543, filed Jan. 13, 2010; U.S. Provisional Patent Application Ser. No. 61/334,533, filed May 13, 2010; U.S. Provisional Patent Application Ser. No. 61/334,529, filed May 13, 2010; U.S. Provisional Patent Application Ser. No. 61/357,582, filed Jun. 23, 2010; U.S. Provisional Patent Application Ser. No. 61/367,607, filed Jul. 26, 2010; and U.S. Provisional Patent Application Ser. No. 61/373,764, filed Aug. 13, 2010.

U.S. patent application Ser. No. 13/680,351 is also a continuation-in-part of U.S. patent application Ser. No. 13/016,575, filed Jan. 28, 2011, which claims the benefit of U.S. Provisional Patent Application Ser. No. 61/299,283, filed Jan. 28, 2010.

U.S. patent application Ser. No. 13/680,351 is also a continuation-in-part of U.S. patent application Ser. No. 13/166,451, filed Jun. 22, 2011, which claims the benefit of U.S. Provisional Patent Application Ser. No. 61/357,582, filed Jun. 23, 2010.

U.S. patent application Ser. No. 13/680,351 is also a continuation-in-part of PCT Application No. PCT/US2011/043698, filed Jul. 12, 2011, which claims the benefit of U.S. Provisional Patent Application Ser. No. 61/367,607, filed Jul. 26, 2010.

U.S. patent application Ser. No. 13/680,351 is also a continuation-in-part of PCT Application No. PCT/US2011/047565, filed Aug. 12, 2011, which claims the benefit of U.S. Provisional Patent Application Ser. No. 61/373,764, filed Aug. 13, 2010.

U.S. patent application Ser. No. 13/680,351 is also a continuation-in-part of U.S. patent application Ser. No. 13/456,570, filed Apr. 26, 2012, which claims the benefit of U.S. Provisional Patent Application Ser. No. 61/480,977, filed Apr. 29, 2011.

U.S. patent application Ser. No. 13/680,351 is also a continuation-in-part of U.S. patent application Ser. No. 13/456,394, filed Apr. 26, 2012, which claims the benefit of U.S. Provisional Patent Application Ser. No. 61/480,960, filed Apr. 29, 2011.

U.S. patent application Ser. No. 13/680,351 is also a continuation-in-part of U.S. patent application Ser. No. 13/456,505, filed Apr. 26, 2012, which claims the benefit of U.S. Provisional Patent Application Ser. No. 61/480,941, filed Apr. 29, 2011; and U.S. Provisional Patent Application Ser. No. 61/549,437, filed Oct. 20, 2011.

U.S. patent application Ser. No. 13/680,351 is also a continuation-in-part of U.S. patent application Ser. No. 13/456,546, filed Apr. 26, 2012, which claims the benefit of U.S. Provisional Patent Application Ser. No. 61/480,941, filed Apr. 29, 2011; and U.S. Provisional Patent Application Ser. No. 61/549,437, filed Oct. 20, 2011.

U.S. patent application Ser. No. 13/680,351 also claims the benefit of U.S. Provisional Patent Application Ser. No. 61/577,399, filed Dec. 19, 2011.

Each of these applications is incorporated herein by reference.

FIELD OF INVENTION

The present invention generally relates to systems and methods for delivering to and/or receiving fluids or other materials, such as blood or interstitial fluid, from subjects, e.g., to or from the skin and/or beneath the skin.

BACKGROUND

Phlebotomy or venipuncture is the process of obtaining intravenous access for the purpose of intravenous therapy or obtaining a sample of venous blood. This process is typically practiced by medical practitioners, including paramedics, phlebotomists, doctors, nurses, and the like. Substantial equipment is needed to obtain blood from a subject, including the use of evacuated (vacuum) tubes, e.g., such as the Vacutainer™ (Becton, Dickinson and company) and Vacuette™ (Greiner Bio-One GmBH) systems. Other equipment includes hypodermic needles, syringes, and the like. However, such procedures are complicated and require sophisticated training of practitioners, and often cannot be done in non-medical settings. Accordingly, improvements in methods of obtaining blood or other fluids from or through the skin are still needed.

SUMMARY OF INVENTION

In some embodiments, the present invention generally relates to devices and methods for receiving fluids from a subject, such as the reception and separation of blood to form plasma or serum. The subject matter of the present invention involves, in some cases, interrelated products, alternative solutions to a particular problem, and/or a plurality of different uses of one or more systems and/or articles.

In one aspect of the invention, the device includes a flow activator arranged to cause fluid to be released from a subject. The flow activator may be moved in a deployment direction by a deployment actuator. The flow activator may also be moved in a retraction direction by a retraction actuator. In one aspect, the flow activator may be at a distance from the opening before deployment that is different from its distance from the opening after retraction.

In another aspect of the invention, an effector that includes only mechanical components moves the flow activator for deployment and retraction. Deployment movement may occur substantially faster than retraction movement.

In another aspect of the invention, the device may include a fluid transporter including an opening and a flow activator, the flow activator being arranged to cause fluid to be released from the subject, as well as a vacuum source that provides a pressure less than ambient pressure. The device may also include a channel that is fluidly coupled between the opening and the vacuum source. In one aspect of the invention, the flow activator is actuated after enablement of fluid communication between the opening and the vacuum source along the channel. In one aspect of the invention, fluid communication between the opening and the vacuum source along the channel is enabled before the flow activator is moved in a retraction direction. In another aspect, a device actuator that actuates the flow activator also enables fluid communication between the opening and the vacuum source along the channel.

In another aspect of the invention, the effector may have an initial stored potential energy prior to any deployment movement of the flow activator. The effector may be arranged to release the stored potential energy to retract the flow activator.

In another aspect of the invention, flow activator, retraction actuator, and deployment actuator may be concentrically aligned with one another. Additionally, the device may include a spacer element that is also concentrically aligned with the flow activator, retraction actuator, and deployment actuator.

In another aspect, the present invention encompasses methods of making one or more of the embodiments described herein, for example, a device for receiving fluid. In still another aspect, the present invention encompasses methods of using one or more of the embodiments described herein, for example, a device for receiving fluid.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments that incorporate one or more aspects of the invention will be described by way of example with reference to the accompanying figures, which are schematic and are not necessarily intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
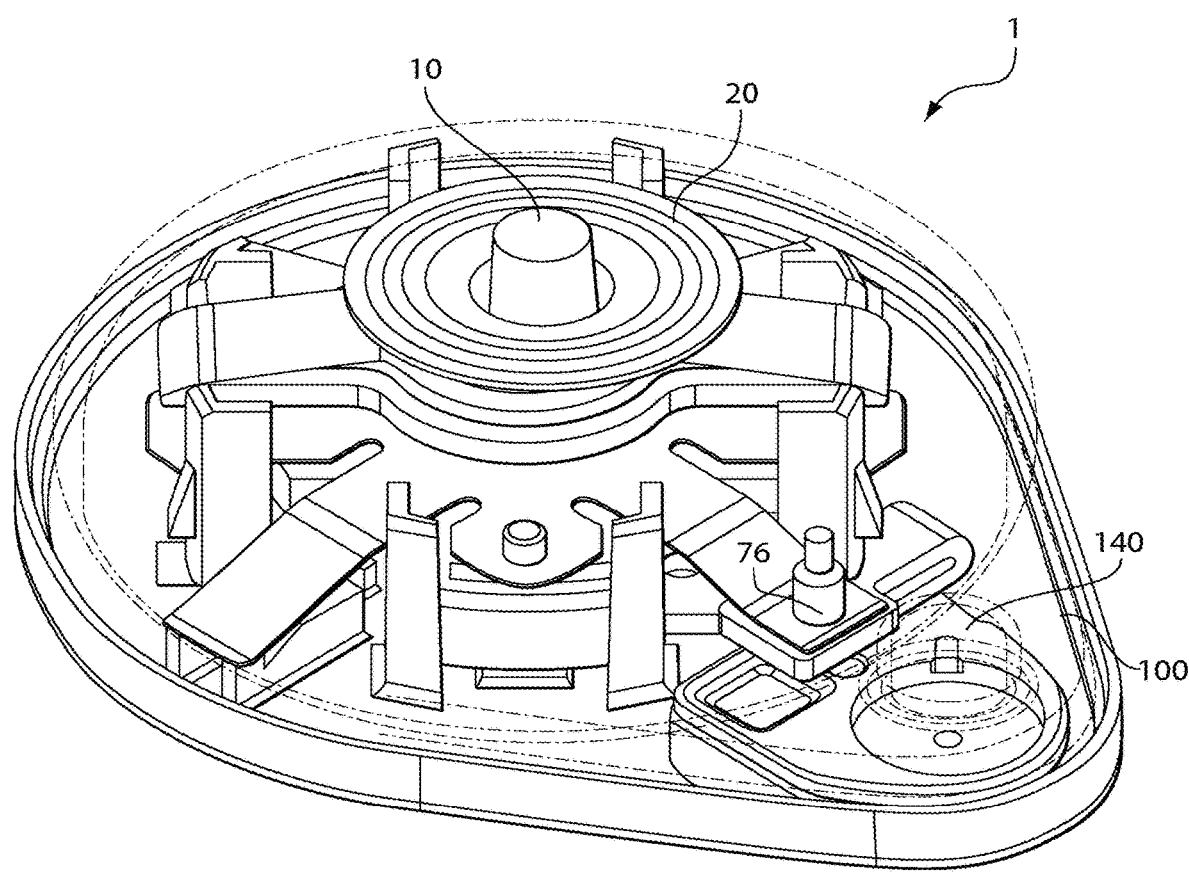
FIG. 1 is a perspective view of a fluid receiving device in accordance with aspects of the invention.

Aspects of the invention are not limited in application to the details of construction and the arrangement of components set forth in the following description or illustrated in the drawings. For example, illustrative embodiments relating to piercing skin and receiving blood released from the pierced skin are discussed below, but aspects of the invention are not limited to use with devices that pierce skin and/or receive blood. Other embodiments may be employed, such as devices that receive other bodily fluids without piercing, and aspects of the inventions may be practiced or be carried out in various ways. Also, the phraseology and terminology used herein is for the purpose of description and should not be regarded as limiting.

FIG. 1 shows a fluid receiving device 1 that incorporates various aspects of the invention. Although FIG. 1 incorporates many of the aspects of the invention, any suitable number of aspects of the invention may be incorporated into a fluid receiving device. Thus, aspects of the invention may be used alone or in any suitable combination with each other. This illustrative embodiment includes a cover 20 and a base 100 that are joined together and may cooperate to enclose various parts of the device 1 and support one or more external features, such as a device actuator 10 that is used to cause the device 1 to receive fluid from a subject. The base 100 and the cover 20 may be formed from or otherwise include Polyester (PCTA or PETG) or other polymers with low gas permeability. Although the device actuator 10 in this embodiment is arranged to be actuated by a user (e.g., by the press of a finger), the device actuator 10 may be arranged in other ways, e.g., for actuation by a machine, an electrical signal, or other suitable arrangement to cause the fluid receiving device 1 to receive fluid from a subject. Actuation of the device actuator 10 may occur automatically, e.g., in response to an elapsed timer or other stimulus or condition, or manually. In some embodiments, the device actuator 10 may include a push-button as shown, a sliding button discussed more below, a touch-screen interface, a switch, or other user-actuatable arrangement, etc. In some cases, the device actuator 10 may allow for actuation of the device 1 only once, e.g., the device actuator 10 may become locked in a position that prevents further actuation, or may allow the device 1 to be actuated multiple times.

According to one aspect of the invention, the device 1 may include a fluid transporter that receives fluid from a subject. The fluid transporter may include an applicator region where bodily fluids from the body may accumulate. In some embodiments, the applicator region may be a recess or an indentation within the base of the device, which can receive a fluid from the surface of the skin. The applicator region may have any suitable shape. For example, the applicator region can be generally hemispherical, semi-oval, rectangular, irregular, etc. More details regarding the applicator region can be found in U.S. and international patent applications each entitled "Systems and Methods for Collecting a Fluid from a Subject", filed on even date herewith, incorporated herein by reference in its entireties. Also incorporated herein by reference in its entirety is U.S. Provisional Patent Application Ser. No. 61/480,960, entitled "Systems and Methods for Collecting a Fluid from a Subject," by Haghgooie, et. al., filed on Apr. 29, 2011.

The fluid transporter may include an opening of any size and/or geometry that is constructed to receive fluid into the device. For example, the opening may lie in a two-dimensional plane or the opening may include a three-dimensional cavity, hole, groove, slit, etc. In some embodiments, the fluid transporter may also include a flow activator, such as one or more microneedles, arranged to cause fluid to be released from the subject, e.g., by piercing the skin of a subject. In some embodiments, if fluid may partially or fully fill an enclosure surrounding a flow activator, then the enclosure can define at least part of a fluid transporter.

It should be noted that a flow activator need not be included with all embodiments as the device may not necessarily employ a mechanism for causing fluid release from the subject. For instance, the device may receive fluid that has already been released due to another cause, such as a cut or an abrasion, fluid release due to a separate and independent device, such as a separate lancet, an open fluid access such as during a surgical operation, and so on. Additionally, fluid may be introduced into the device via urination, spitting, pouring fluid into the device, etc. If included, a flow activator may physically penetrate, pierce, and/or or abrade, chemically peel, corrode and/or irritate, release and/or produce electromagnetic, acoustic or other waves, other otherwise operate to cause fluid release from a subject. The flow activator may include a moveable mechanism, e.g., to move a needle, or may not require movement to function. For example, the flow activator may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of a flow activator to cause fluid release from a subject.

Figure 2:
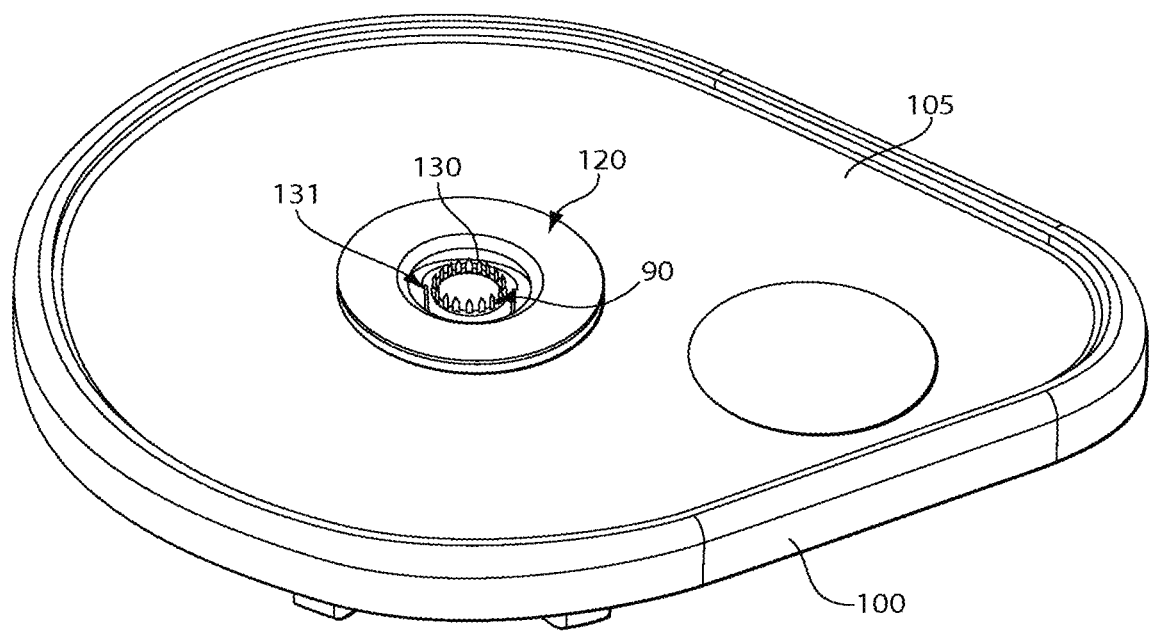
FIG. 2 is a perspective view of the underside of the device shown in FIG. 1.

FIG. 2 shows an underside of the fluid receiving device 1 of FIG. 1 with a fluid transporter 120 that includes an opening 130, an applicator region 131, and a flow activator 90. In this embodiment, the flow activator 90 includes one or more needles. As described in more detail below, the needles may be extended from the opening 130 to pierce a subject's skin, and then retracted back into the opening to allow blood or other fluid to enter the opening 130. That is, to use the device 1 to receive blood from a subject, the base 100 may be placed on the skin so that the opening 130 is adjacent the skin. Thereafter, the device actuator 10 may be depressed to cause the needles to be deployed, piercing the skin and causing blood to be released. Blood may enter the opening and be collected in the storage chamber 140. In one embodiment, blood may flow into the storage chamber 140 as a result of a relatively low pressure (vacuum) in the device 1 that draws blood from the opening 130 and into the storage chamber 140 (see FIG. 4).

The needles may be of any suitable width, length and/or other size, and the needles may each be solid or hollow. The needles may have any suitable cross-section (e.g., perpendicular to the direction of penetration), such as circular, square, oval, elliptical, rectangular, rounded rectangle, triangular, polygonal, hexagonal, irregular, etc. In some embodiments, the needles may have a length of about 5 mm or less. Additional information regarding alternative needle arrangements is provided below.

In this embodiment (FIG. 4), activation of the device actuator 10 causes the flow activator 90 to release blood or other fluid from a subject, which is then received at the opening 130. The blood or other fluid may then be collected in one or more chambers 140. Collection of the blood or other fluid may be done in any suitable way, such as by absorption, capillary action, suction, or other means. In this illustrative embodiment, activation of the device actuator 10 causes a seal 76 to open so that blood or other fluid may flow from the opening 130, through a channel (see FIG. 4, element 110) to a chamber 140. As is explained more below, the device 1 may include a vacuum source that draws the blood or other fluid from the opening 130 and into the chamber 140 upon opening of the seal 76. That is, opening of the seal 76 may introduce a relatively low pressure to the chamber 140, which causes blood or other fluid to be drawn from the opening 130 and into the chamber 140.

In one aspect of the invention, the flow activator may be actuated by a deployment actuator and a retraction actuator. For example, the flow activator may be moveable and movement of the flow activator may be caused by a deployment actuator and a retraction actuator. The deployment actuator may cause the flow activator to move in a deployment direction towards the skin and/or other surface of a subject, and the retraction actuator may cause the flow activator to move in a retraction direction away from the skin and/or body of a subject. As discussed in more detail below, providing separate actuators for deployment and retraction movement may provide advantages in some cases, such as enabling the flow activator to be moved at different speeds for deployment and retraction, allowing the actuators to perform other additional functions such as opening a fluid flow path for blood or other fluid, enabling the flow activator to start and finish at different positions in the device before deployment and after retraction, and others. The deployment actuator and the retraction actuator may each include any number of suitable components, such as a button, a switch, a lever, a slider, a dial, a compression spring, a Belleville spring, a servo, rotary or linear electric motor, and/or a pneumatic apparatus, or other suitable device. Also, the deployment actuator and the retraction actuator may be of the same type, or may be different types of devices. Each actuator may operate manually, mechanically, electrically, pneumatically, electromagnetically, or other suitable mode of operation, and may or may not require user input for activation.

Figure 3:
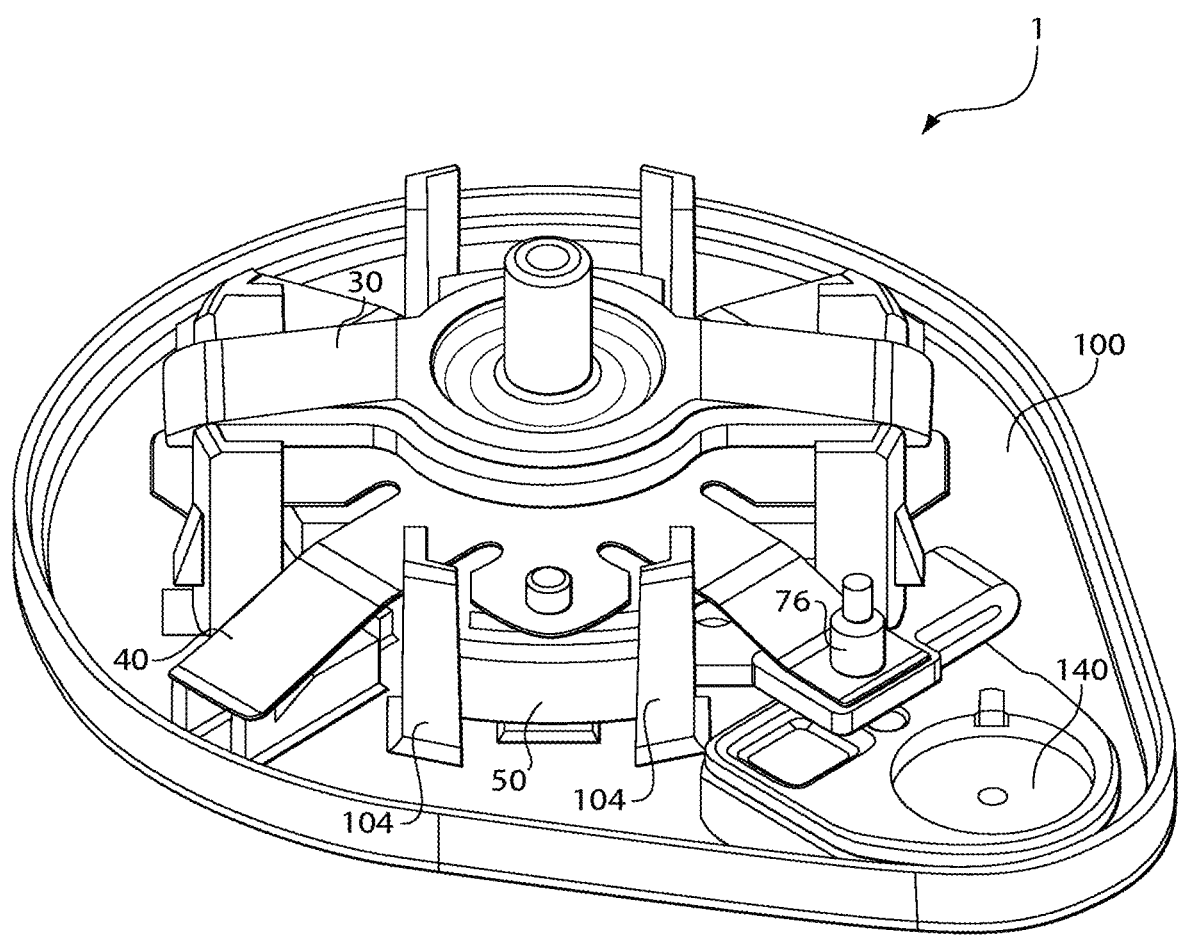
FIG. 3 is a perspective view of the device shown in FIG. 1 with the cover removed.
Figure 4:
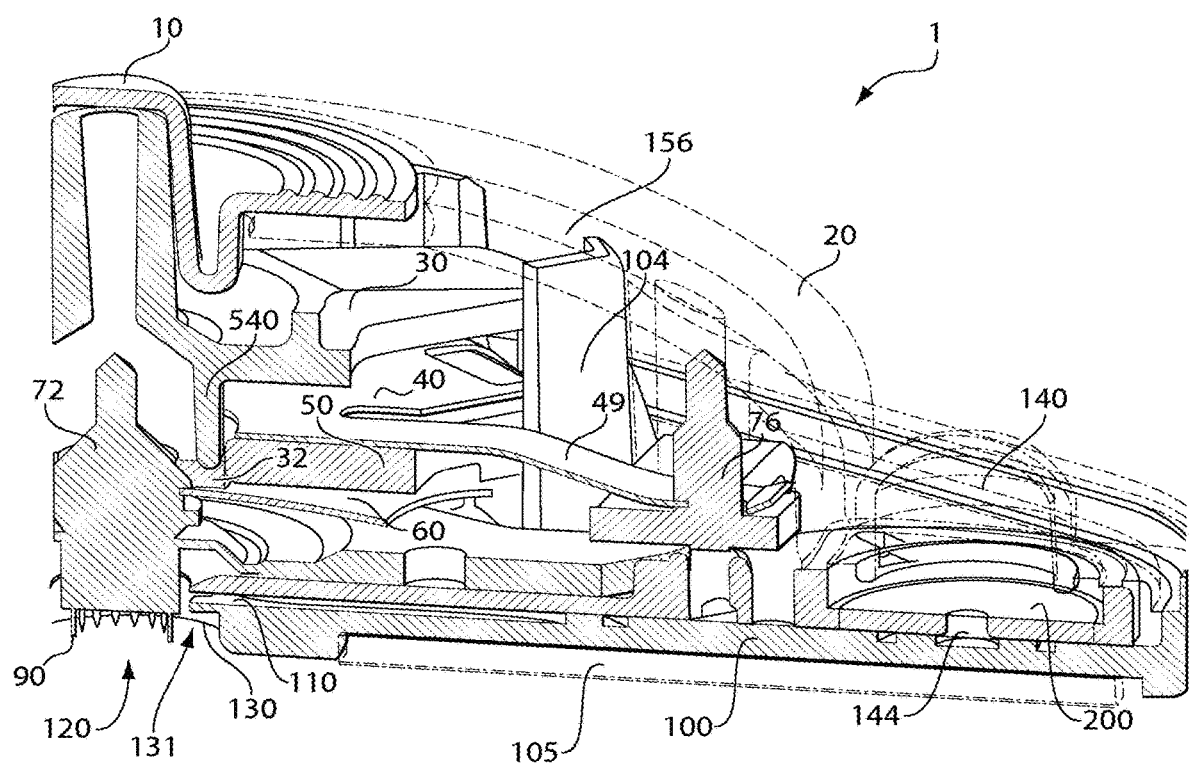
FIG. 4 is a cross-sectional view of the device shown in FIG. 1.
Figure 5:
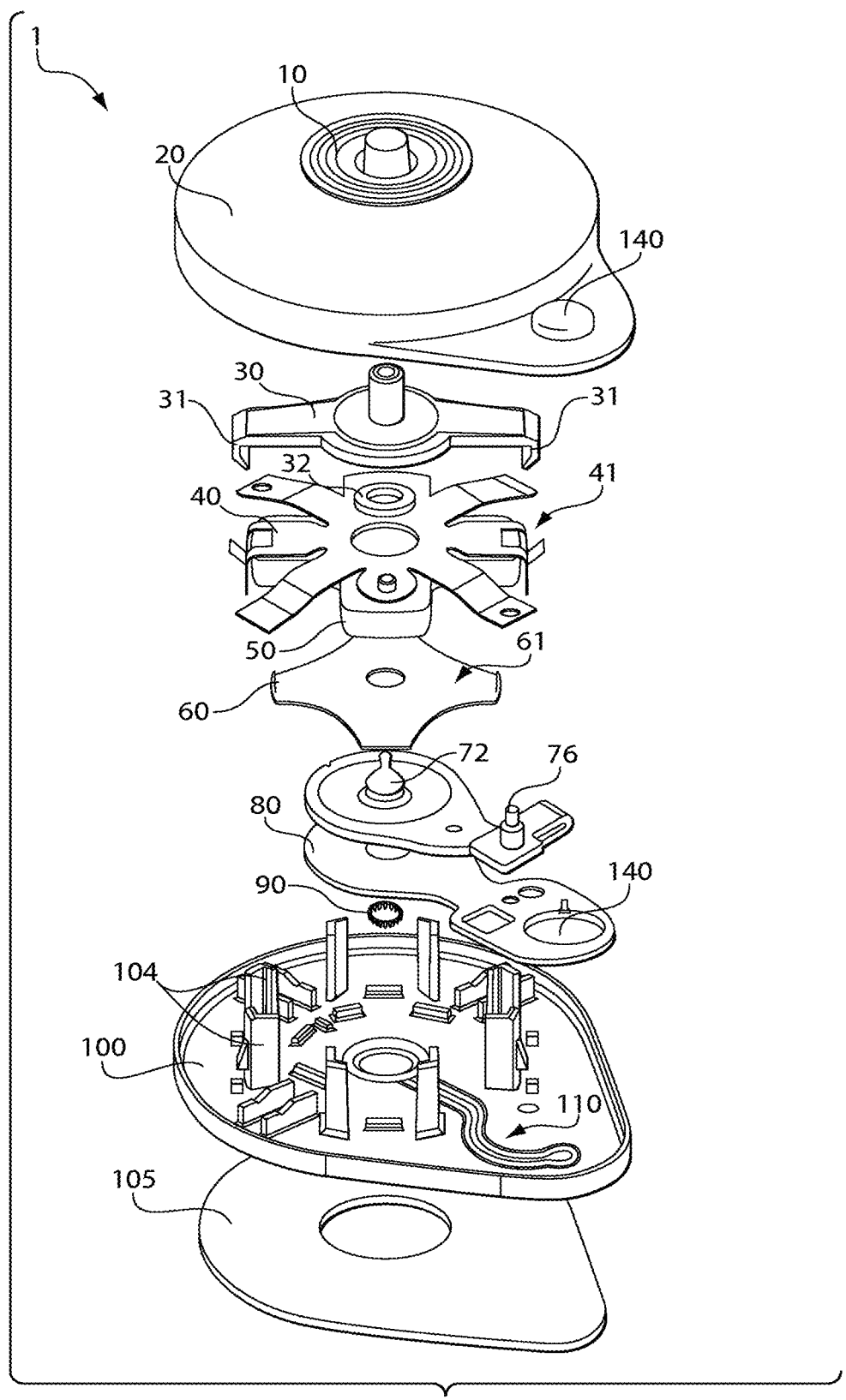
FIG. 5 is an exploded view of the device shown in FIG. 1.

In accordance with an aspect of the invention, an effector may be arranged to cause deployment and/or retraction movement of a flow activator. For example, an effector may include both a deployment actuator and a retraction actuator. The effector may be formed from or otherwise include polyester (PETG or PCTA), or acetal resin, acrylonitrile butadiene styrene (ABS), etc. FIGS. 3, 4, and 5 illustrate a perspective view of device 1 of FIG. 1 with the cover 20 removed from the base 100, a partial cross sectional view of the device 1, and an exploded view of the device 1, respectively. In this embodiment, the device 1 includes an effector 50 that includes a retraction actuator 40 and a deployment actuator 60 and that is movable in up and down directions relative to the base 100 along effector guides 104. The deployment actuator 60 is attached to the flow activator 90 via a membrane 72 (see FIG. 4) so that downward movement of the deployment actuator 60 may cause the flow activator 90 to at least partially extend from the opening 130. (As discussed more below, the membrane 72 may separate a vacuum source 156 in the device 1 from the opening 130 so that a relatively low pressure is maintained in the vacuum source 156 until controllably opened to cause flow into the storage chamber 140. The vacuum source 156 may be in the form of a sealed vacuum chamber.) In this embodiment, the deployment actuator 60 has a generally domed shape (e.g., as in a Belleville spring) with a central hole that receives a part of the membrane 72 which attaches the deployment actuator 60 to the flow activator 90. (Although in this embodiment the flow activator 90 is attached to the deployment actuator 60 via the membrane 72, the flow activator 90 may be directly connected to the deployment actuator 60, e.g., via a vertical post or other structure that extends from the flow activator 90 to the deployment actuator 60.) The deployment actuator 60 may initially be arranged in a concave-down configuration shown in FIG. 4 and moved to a concave-up configuration, e.g., by a user pressing the device actuator 10 to cause a release element 30 to push a center portion of the deployment actuator 60 downwardly. The deployment actuator 60 may be made of a suitable material and configuration to rapidly move from the concave-down to concave-up configurations so as to rapidly extend the flow activator 90 from the opening 130 and pierce a subject's skin or other surface. While the deployment actuator 60 in this embodiment is arranged as a flexible spring with a dome shape, the deployment actuator 60 may be of any suitable shape and/or size. For example, the deployment actuator 60 may be circular (having no "legs" unlike the four legs shown in FIG. 5), oblong, triangular (have 3 legs), square (4 legs with straight sides between each leg), pentagonal (5 legs), hexagonal (6 legs), spider-legged, star-like, clover-shaped (with any number of lobes, e.g., 2, 3, 4, 5, etc.), a serrated disc or a wave shape, or the like. The deployment actuator 60 may have, in some embodiments, a central hole as shown or another feature, such as a dimple, or button in the center or other location. The deployment actuator 60 may be formed from or otherwise include any suitable material, for example, a metal such as stainless steel (e.g., 301, 301LN, 304, 304L, 304LN, 304H, 305, 312, 321, 321H, 316, 316L, 316LN, 316Ti, 317L, 409, 410, 430, 440A, 440B, 440C, 440F, 904L), carbon steel, spring steel, spring brass, phosphor bronze, beryllium copper, titanium, titanium alloy steels, chrome vanadium, nickel alloy steels (e.g., Monel 400, Monel K 500, Inconel 600, Inconel 718, Inconel×750, etc.), a polymer (e.g., polyvinylchloride, polypropylene, polycarbonate, etc.), a composite or a laminate (e.g., comprising fiberglass, carbon fiber, bamboo, Kevlar, etc.), or the like.

In some embodiments, all portions of the deployment actuator may move less than a certain distance when the deployment actuator moves in a deployment direction towards opening 130. In some embodiments, all portions of the deployment actuator may move less than about 10 mm, less than about 5 mm, less than about 3 mm, less than about 2 mm, or less than about 1 mm. The retraction actuator 40 in this embodiment includes a reversibly deformable structure in the form of a leaf spring, but, like the deployment actuator 60, other arrangements are possible such as a coil spring, foam, an elastic bladder, or the like. The retraction actuator may be formed from or otherwise include any suitable material, for example, 1095 spring steel or 301 stainless steel or other spring material such as 1074/1075, 5160, 9255 spring steel etc. The retraction actuator 40 is attached to the deployment actuator 60 via the effector body 50 so that when the retraction actuator 40 is released upon actuation of the device actuator 10, the retraction actuator 40 (and other portions of the effector 50) can move away from the opening 130 along the effector guides 104. This retraction motion draws the flow activator 90 and the deployment actuator 60 away from the opening as well. Specifically, and as shown at least in part in FIGS. 4 and 5, before actuation of the device 1, the retraction actuator 40 is in a compressed state, storing potential energy. That is, the center of the retraction actuator 40 is pressed downwardly during assembly so that four arms of the retraction actuator 40 are elastically deformed. The retraction actuator 40 is held in this depressed condition by ear portions 103 (see FIGS. 8 and 9) of the retraction actuator 40 engaging with the base 100 until the device 1 is actuated. However, when the device actuator 10 is pushed down during device actuation, arms 31 of the release element 30 engage with the tabs 41 to release the ear portions 103 from the base 100, allowing the center portion of the retraction actuator 40 to move in a retraction direction away from the opening 130. Since the deployment actuator 60 and flow activator 90 are attached to the retraction actuator 40, movement of the retraction actuator 40 upward away from the opening 130 retracts the flow activator 90 from the opening 130. Additionally, movement of the retraction actuator 40 upward away from the opening 130 may also move the deployment actuator 60 in a retraction direction away from the opening 130 as well. In some embodiments, all portions of the deployment actuator 60 may move less than a certain distance when the deployment actuator 60 moves in a retraction direction away from the opening 130. In some embodiments, all portions of the deployment actuator may move less than about 10 mm, less than about 5 mm, less than about 3 mm, less than about 2 mm, or less than about 1 mm.

In some embodiments, as shown in FIG. 4, a spacer element 32 is located between the deployment actuator 60 and the retraction actuator 40. The spacer element 32 may help to eliminate a gap between the deployment actuator 60 and the release element 30. Actuation of device actuator 10 may cause the release element 30 to push down on the spacer element 32, which may in turn push on the deployment actuator 60 and cause the deployment actuator 60 to move the flow activator 90 in a deployment direction. In some embodiments, the flow activator 90, deployment actuator 60, retraction actuator 40, and spacer element 32 are substantially concentrically aligned. By providing both a deployment actuator 60 and a retraction actuator 40 for the flow activator 90, the flow activator 90 may be controlled to have any suitable movement for both deployment and retraction. For example, the flow activator 90 may be caused to move more rapidly in the deployment direction than in the retraction direction, which has been found to potentially reduce pain when piercing skin to release blood. That is, the deployment actuator 60 may be arranged to relatively rapidly move from the concave-down to concave-up configuration, quickly inserting the flow activator 90 into skin or another surface. Thereafter, the flow activator 90 may be more slowly withdrawn from the skin by the retraction actuator 40, e.g., as controlled by a relatively lower force exerted by the retraction actuator 40 on the flow activator 90 than the deployment actuator 60, by damped motion of the retraction actuator 40, or other suitable arrangements. In other embodiments, having separate deployment and retraction actuators may allow for a shorter range of motion in one direction, such as in the deployment direction, than in another direction, such as the retraction direction. For example, by having the flow activator 90 move a relatively short distance for deployment, the deployment actuator 60 may be made relatively compact, yet generate suitably high force to insert the flow activator 90 into skin. In contrast, a relatively longer distance traveled by the flow activator 90 during retraction may withdraw the activator 90 suitably to allow a pool or other collection of blood to enter a cavity or other space for reception by the device 1. Additionally, a short deployment distance may minimize alignment errors inherent in long travel distances.

Figure 6A:
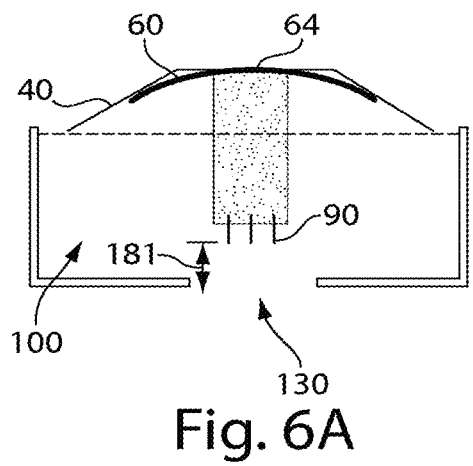
FIGS. 6A-6C show a series of three states of a flow activator of the device of FIG. 1.
Figure 6B:
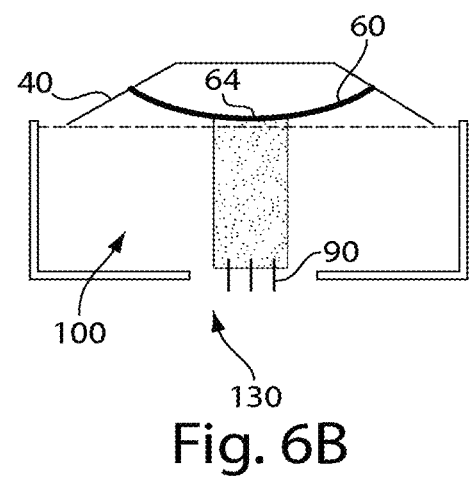
Figure 6C:
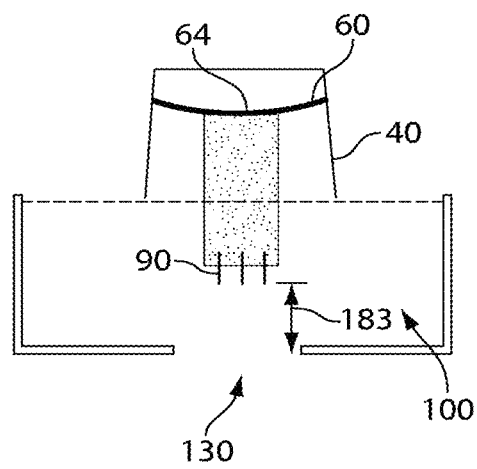

Accordingly, in one aspect of the invention, the flow activator may be located at an initial pre-deployment distance from skin or another surface that is different from a final post-retraction distance between the flow activator and the skin or other surface. While this aspect can be provided in many different ways, such as by a motor, servo, or automated device as part of an effector, the effector 50 of the FIGS. 1-5 embodiment may provide an arrangement in which flow activator 90 is relatively close to the opening 130 prior to deployment, and is located relatively further away from the opening 130 after retraction. FIGS. 6A-6C show a series of schematic representations of three states of the device 1 of FIGS. 1-5, including an initial state before deployment of the flow activator 90, an intermediate state where the flow activator is extended from the opening 130 or otherwise positioned to cause release of fluid from a target skin or other surface, and a final state where the flow activator 90 is retracted, respectively.

As can be seen in FIG. 6A, a pre-deployment distance 181 between the opening 130 and the flow activator 90 is relatively small, such as 1 mm or less. In this state, the retraction actuator 40 is compressed, and the deployment actuator 60 is in a concave-down arrangement. As shown in FIG. 6B, the deployment actuator 60 is inverted to a concave-up configuration so that the flow activator 90 is deployed. The retraction actuator 40 may also be further compressed, e.g., by the user pressing down on the release element 30, but in other embodiments, the retraction actuator 40 need not be further compressed or otherwise deformed. As shown in FIG. 6C, a post-retraction distance 183 between the opening 130 and the flow activator 90 may be larger, in some cases significantly larger, than the pre-deployment distance 181. For example, the post-retraction distance 183 in which the flow activator 90 is fully retracted from the opening 130 may be 2-3 mm or more. Retraction of the flow activator 90 from the opening 130 may provide a space into which blood or other fluid released from the subject may collect and/or otherwise be received by the device 1. However, other arrangements are possible in which the post-retraction distance is less than, or the same as, the pre-deployment distance, and all aspects of the invention are not necessarily limited in this regard.

Figure 7A:
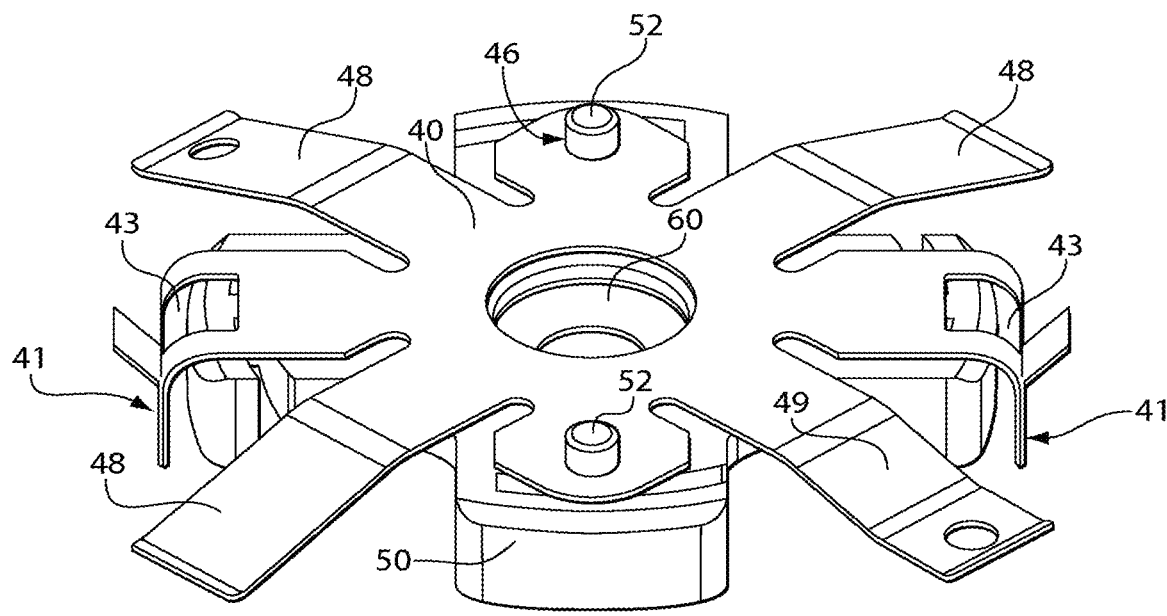
FIG. 7A is an enlarged view of an effector including a retraction actuator and deployment actuator in a specific arrangement.
Figure 7B:
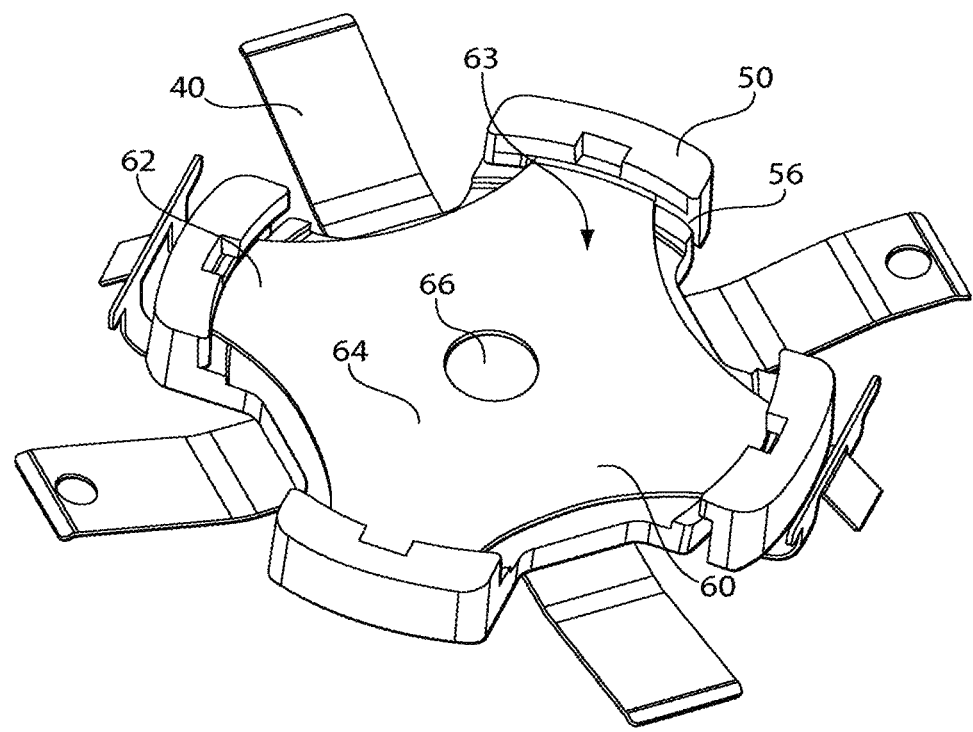
FIG. 7B is an underside view of the arrangement shown in FIG. 7A.

FIGS. 7A and 7B show top perspective and bottom perspective views of the effector 50 of the FIGS. 1-5 embodiment, and help to better illustrate how the motion of the effector 50 is controlled. As shown in FIG. 7A, the retraction actuator 40 has eight legs radiating from a central body having a central hole. Two of the shorter legs attach the retraction actuator 40 to the effector body 50 via two posts 52 that extend through holes 46 of the retraction actuator 40. The diameter of the post heads 52 may be made larger than the holes 46 and thus fix the retraction actuator 40 to the effector body 50. The retraction actuator 40 may alternately be attached to the effector body by 50 by adhesive (e.g. tape, liquid), mechanical fastening (e.g. interference fit, slot/groove, screws) or thermal methods (e.g. heat staking), and is not limited in this regard. Other legs 48 of the retraction actuator 40 may remain free to flex relative to the effector body 50, e.g., to provide the retraction movement of the effector 50. Two of the legs 48 include ear portions 103 which serve to engage with the base 100 and hold the retraction actuator 40 in a compressed, initial position before deployment of the flow activator 90. A space or gap 43 is provided between the ear portions 103 and the effector body 50 to allow the ear portions 103 to move toward the body for engagement with the base 100. As described above and shown in FIG. 7B, the deployment actuator 60 includes a central hole 66 and lobes 62 that are held within the grooves 56 of the effector body 50. Although the deployment actuator 60 is attached to the effector body 50, a central portion 64 of the deployment actuator 60 remains displaceable relative to the effector body 50 so that the deployment actuator 60 may move to deploy the flow activator 90.

Figure 8:
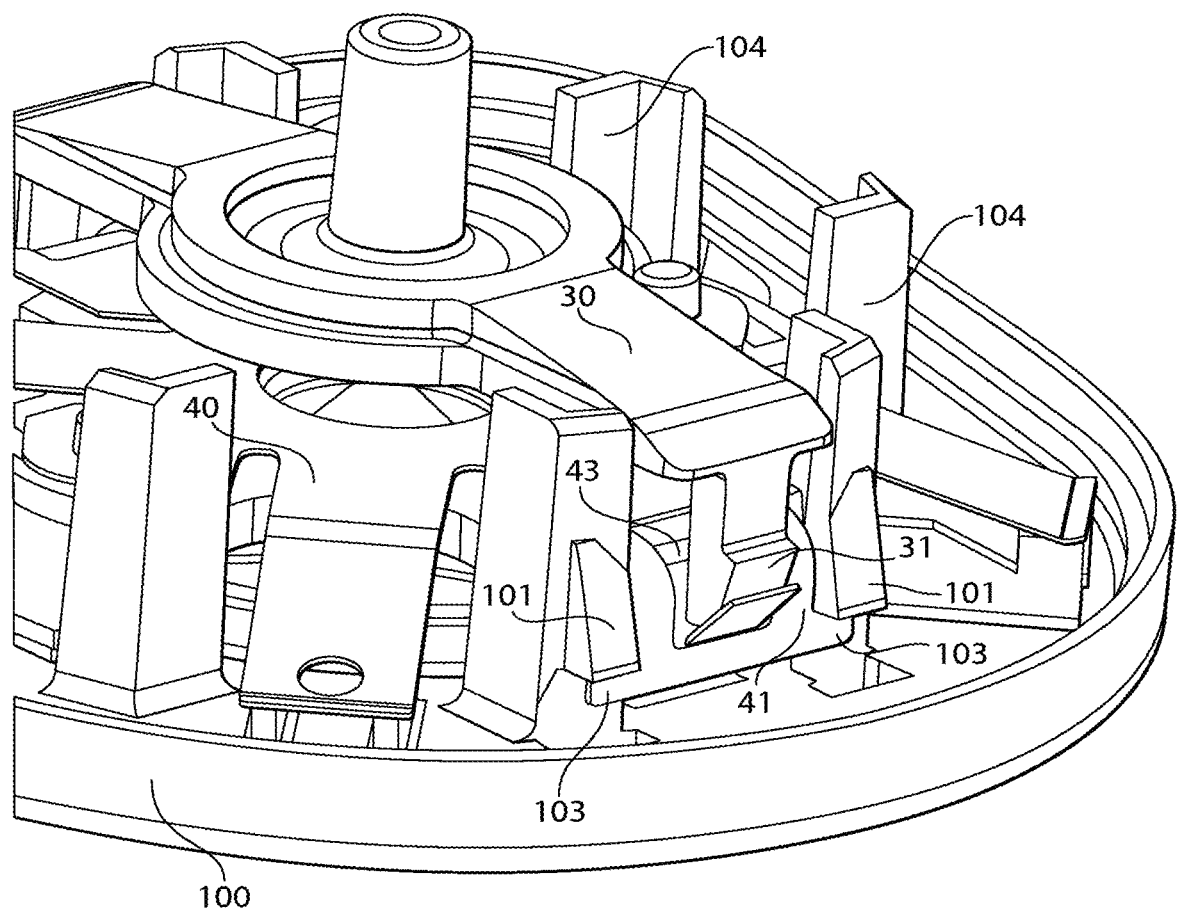
FIG. 8 is a close up view of a release element for the retraction actuator of the device shown in FIG. 1.
Figure 9:
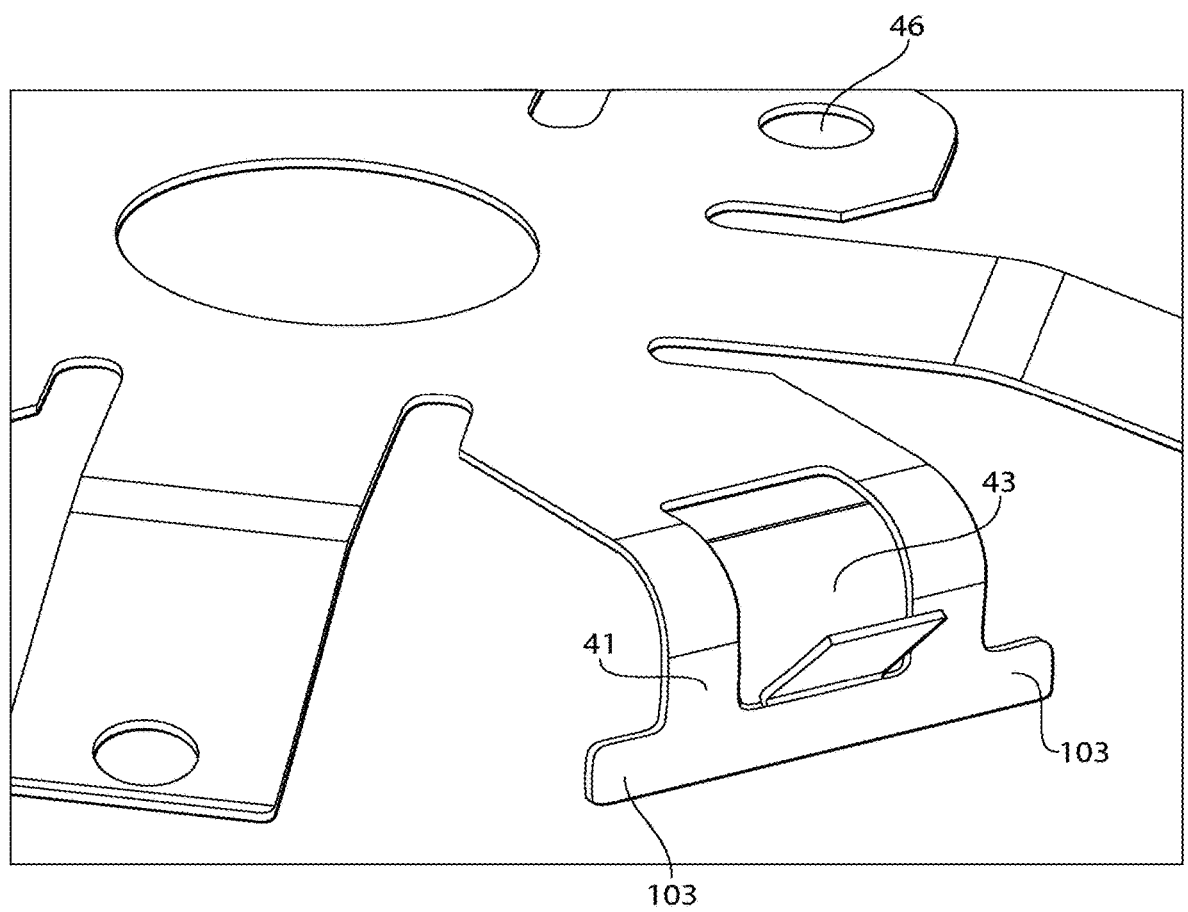
FIG. 9 is an enlarged view of a portion of the retraction actuator of the device shown in FIG. 1.

As discussed above, the effector 50 may be mounted to the base 100 and guided in motion via effector guides 104 that protrude from the base 100. FIG. 8 shows a close up view of the retraction actuator 40 illustrating how the retraction actuator 40 engages with the base 100 in a compressed, initial state, while FIG. 9 shows a close up view of the ear portions 103 on two of the legs 48 of the retraction actuator 40 that engage with the base 100 to hold the retraction actuator 40 in the compressed, initial state. With the effector 50 held suitably by the effector guides 104, the effector 50 is pressed downwardly so that ear portions 103 of the tabs 41 can be positioned under corresponding protrusions 101 on the base 100. With the ear portions 103 engaged with the protrusions 101, the effector 50 may be released so that the spring force of the legs 48 biases the effector 50 to move upwardly in the retraction direction. However, with the ear portions 103 engaged with the protrusions 101, the effector 50 is held in a compressed condition. In this pre-deployment arrangement, the flow activator 90 may be at the initial pre-deployment distance 181 (see FIG. 6) from the opening 130. In some embodiments, this pre-deployment distance 181 may be arranged such that actuation of the deployment actuator 60 will cause the flow activator 90 to reach the skin of a subject and allow the flow activator 90 to penetrate and/or pierce the skin to cause fluid flow. Thus, having the retraction actuator 40 pre-loaded in an initial semi-compressed state may hold the flow activator 90 at a pre-deployment distance 181 that enables the flow activator 90 to be ready for deployment upon actuation of the device actuator 10.

FIG. 8 also illustrates how the retraction actuator 40 may be released to retract the flow activator 90. Arms 31 of the release element 30 may engage with the tabs 41 so that sloped portions of the arms 31 push the tabs 41 outwardly and away from the effector body 50 when the device actuator 10 and the release element 30 are moved downwardly. This releases the ear portions 103 from the protrusions 101, allowing the effector 50 to move upwardly under the bias of the deformed legs of the retraction actuator 40. The release element 30 may be formed from or otherwise include polyester (PETG or PCTA), or acetal resin, acrylonitrile butadiene styrene (ABS), etc. While in this embodiment the retraction actuator 40 is shown to engage with the base 100 via a releasable latch arrangement that includes the ear portions 103 and the protrusions 101, other arrangements are possible, such as a releasable lever, a sliding release, a detent, magnets that are separable using a wedge or by flipping polarity, etc., as the invention is not limited in this regard.

In another aspect of the invention, the effector may have an initial stored potential energy prior to any deployment movement of the flow activator. That is, the effector may have stored spring energy or other mechanical energy stored, for example, in an elastically deformed element, stored chemical energy, stored electrical energy, etc., that is used to deploy and/or retract a flow activator or cause other motion of other parts of the fluid receiving device. As explained above, before deployment of the flow activator 90, the retraction actuator 40 may be held in a compressed state by engagement of the ear portions 103 of the legs 48 with protrusion elements 101 on the base 100. Compression of the retraction actuator 40 stores potential energy in the retraction actuator 40 that can be used for different actions, such as retracting the flow activator 90. Thus, having the retraction actuator 40 at an initial compressed state permits the retraction actuator 40 to store potential energy and be ready for actuation without requiring energy to be input to the system at the time of actuation of the device.

In another aspect of the invention, the flow activator may move faster in a deployment direction than in a retraction direction. In the embodiments discussed above, the deployment actuator 60 may be arranged to move from an initial, pre-deployment position to a deployment position in rapid fashion, e.g., in a bi-stable manner. In contrast, the retraction actuator 40 may be arranged, e.g., to have a relatively lower spring constant or other characteristic, to move the flow activator 90 at a slower rate during at least a part of the retraction motion. In one set of embodiments, the flow activator 90 can be deployed at a speed of at least about 0.1 cm/s, at least about 0.3 cm/s, about 1 cm/s, at least about 3 cm/s, at least about 10 cm/s, at least about 30 cm/s, at least about 1 m/s, at least about 2 m/s, at least about 3 m/s, at least about 4 m/s, at least about 5 m/s, at least about 6 m/s, at least about 7 m/s, at least about 8 m/s, at least about 9 m/s, at least about 10 m/s, at least about 12 m/s, etc., at the point where the flow activator 90 initially contacts the skin. Without wishing to be bound by any theory, it is believed that relatively faster deployment speeds may increase the ability of the flow activator to penetrate the skin (without deforming the skin or causing the skin to move in response), and/or decrease the amount of pain felt by the application of the flow activator to the skin. Any suitable method of controlling the penetration speed into the skin may be used, including those described herein. Retraction of the flow activator 90 may occur at a slower speed than deployment, e.g., to help reduce any pain associated with withdrawal of the flow activator 90. Where the retraction actuator 40 includes only mechanical elements that are not electronically controlled, e.g., as in the case of a spring, an elastic member, collapsible foam, etc., the spring or other element may be designed or otherwise arranged to provide a desired retraction speed. Alternately, other mechanical elements, such as one or more dampers may be provided to control a withdrawal speed. Other, electronically controlled systems, such as some servos, pneumatic systems, or the like, may incorporate open or closed loop control to provide a desired retraction rate. In the case of a manually-operated retraction actuator, the user may be able to control the speed of retraction. For example, a retraction actuator in the form of a spring may retract more slowly if force is gradually eased off the device actuator. However, if the force is abruptly removed, (e.g. a user suddenly releases the device actuator), the retraction may occur more quickly, although the fastest possible retraction speed may still be slower than the deployment speed. In some aspects, the fluid receiving device may contain one or more chambers or vessels 140 for holding fluid received from a subject. In some cases, the chambers may be in fluidic communication with one or more fluid transporters and/or one or more microfluidic channels. For instance, the fluid receiving device may include a chamber for collecting fluid withdrawn from a subject (e.g., for storage and/or later analysis), a chamber for containing a fluid for delivery to the subject (e.g., blood, saline, optionally containing drugs, hormones, vitamins, pharmaceutical agents, or the like), etc.

In one aspect of the invention, the device may include a vacuum source. Vacuum (a pressure below ambient) may help facilitate fluid flow into the opening 130 of the device, and/or may help draw skin into the opening 130 for contact with the flow activator 90, and/or may help facilitate fluid flow from the opening 130 to a chamber 140. In some cases, the vacuum source may be one that is self-contained within the device, i.e., the device need not be connected to an external vacuum source (e.g., a house vacuum) during use of the device to withdraw blood or interstitial fluid from the skin and/or from beneath the skin. For example, as shown in FIG. 4, in one set of embodiments, the vacuum source may include a vacuum source 156 having a pressure less than ambient pressure before blood (or other fluid) is withdrawn into the device, i.e., the vacuum source 156 may be at a "negative pressure" (that is, negative relative to ambient pressure) or at a "vacuum pressure" (or just having a "vacuum"). For example, if ambient pressure is at atmospheric pressure, the vacuum in the vacuum source may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg, i.e., below the ambient atmospheric pressure. However, in other embodiments, it should be understood that other pressures may be used and/or that different methods may be used to produce other pressures (greater than or less than atmospheric pressure). As non-limiting examples, an external vacuum or a mechanical device may be used as the vacuum source. For example, the device may comprise an internal vacuum source, and/or be connectable to a vacuum source that is external to the device, such as a vacuum pump or an external (line) vacuum source. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like.

Thus, in some cases, the device may be "pre-packaged" with a suitable vacuum source (e.g., a pre-evacuated vacuum source 156); for instance, in one embodiment, the device may be applied to the skin and activated in some fashion to create and/or access the vacuum source. In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

In some cases, the device includes an interface 105 (see FIGS. 2, 4 and 5) that is able to help the device apply a vacuum to the skin and/or at the opening 130. The interface 105 may be, for example, a suction cup, a layer of a hydrogel material, such as Katecho 10G or other suitable hydrogel, or a circular bowl that is placed on the surface of the skin, and vacuum may be applied to the portion of skin exposed to the device 1 by the interface 105. In one set of embodiments, the interface is part of a support structure, e.g., the base 100. The interface 105 may be formed from any suitable material, e.g., glass, rubber, polymers such as silicone, polyurethane, nitrile rubber, EPDM rubber, neoprene, or the like. In some cases, the seal between the interface 105 and the skin may be enhanced (e.g., reducing leakage), for instance, using vacuum grease, petroleum jelly, a gel, an adhesive or the like. In some cases, the interface 105 may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface 105 may be circular, although other shapes are also possible, for example, square, star-shaped (having 5, 6, 7, 8, 9, 10, 11, etc. points), tear-drop, oval, rectangular, or the like.

Figure 10:
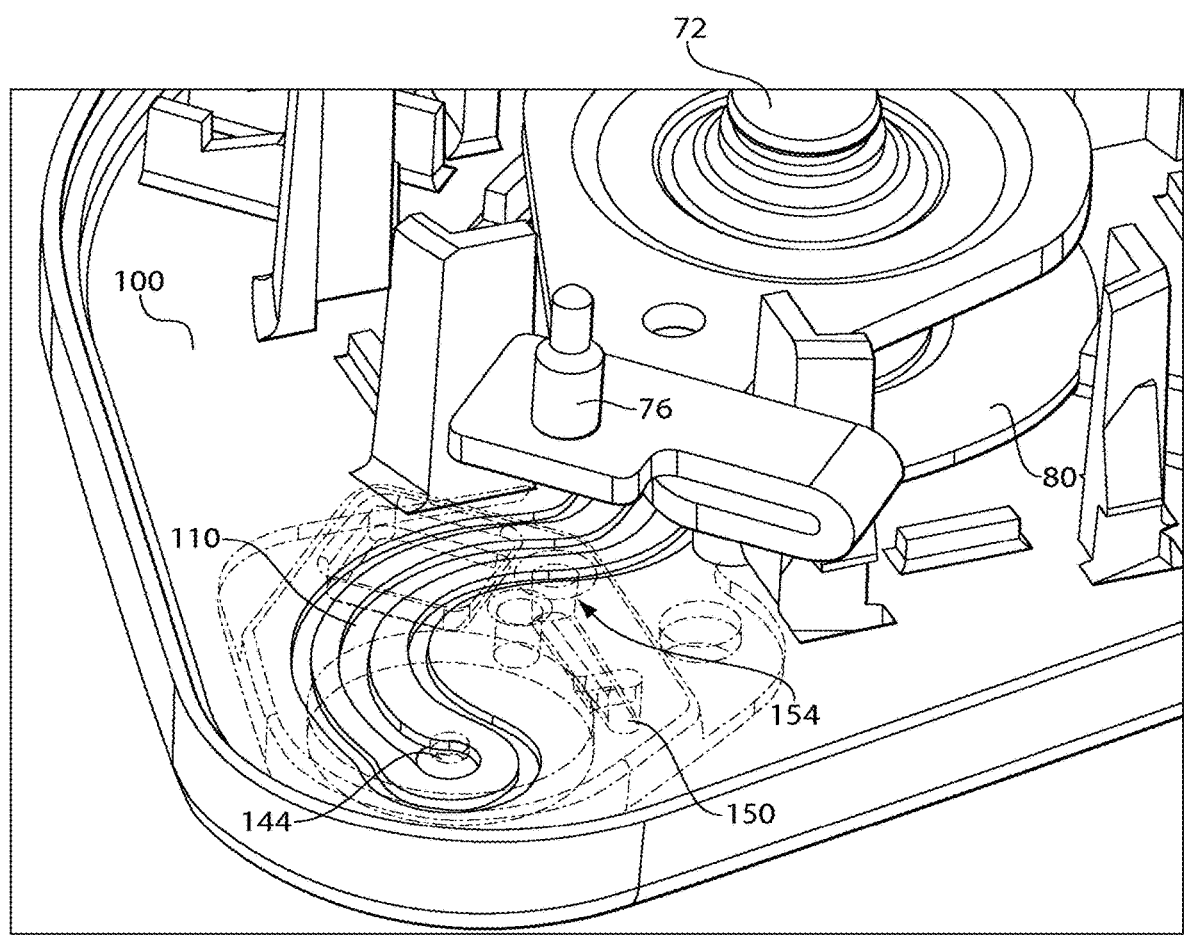
FIG. 10 is an enlarged view of a region of the device shown in FIG. 1 that illustrates a relationship between a storage vessel and a vacuum source.

In some embodiments, vacuum from a vacuum source may facilitate the movement of blood or other fluids from an opening of a fluid transporter to a storage vessel. In the FIGS. 1-5 embodiment, vacuum may be stored in a vacuum source 156, e.g., a majority of space enclosed between device cover 20, base 100, and membrane 72. Vacuum in the vacuum source 156 may be selectively coupled to the storage chamber 140 so as to cause fluid at the opening 130 to be drawn into a channel 110 and to the chamber 140. For example, and as can be seen in FIG. 5, one or more channels 110 may be formed into the base 100 or otherwise provided between the opening 130 and the storage chamber 140. The channel 110 may be covered at an upper side by a lower surface of a channel plate 80. In some embodiments, the channel plate 80, membrane 72 and seal 76 could form a single part. (Additional configuration options for the channel 110 are discussed below.) The channel plate 80 may not only help to define the channel 110, but also define at least a portion of the cavity at the fluid transporter 120, part of the storage chamber 140, a vacuum inlet 154 and flow path 150 used for control of flow between the vacuum source 156 and the storage chamber 140, and a flow path between the channel 110 and the storage chamber 140. That is, as shown in FIGS. 4 and 10, the channel plate 80 helps to define a flow path between the opening 130 and the vacuum source 156 such that flow from the opening 130 may pass through the channel 110 and to an opening 144 in the channel plate 80 that connects the channel 110 and the storage chamber 140. The opening 144 may include a filter, a hydrophobic element (e.g., to help prevent aqueous fluid in the storage chamber 140 from later exiting the chamber 140), a one-way valve, or may be completely unobstructed. As can be seen in FIG. 10, flow may also occur from the storage chamber 140 through a passage 150 in the channel plate 80 to the vacuum inlet 154. The vacuum inlet 154 is normally closed by a seal 76, which may be part of the membrane 72, which also helps to isolate the vacuum source 156 from the opening 130 and other potential outlets for the low pressure in the vacuum source 156. As can be seen in FIG. 4, the seal 76 is engaged with one of the legs 48 of the retraction actuator 40 (a seal leg 49) so that when the retraction actuator 40 is in a compressed, initial state, the seal leg 49 presses the seal 76 into contact with the vacuum inlet 154 so as to close the passage 150 and prevent communication between the vacuum source 156 and the storage chamber 140. However, once the retraction actuator 40 is released, the seal leg 49 may move upwardly and/or the force of the seal leg 49 on the seal 76 may be reduced to a point at which the vacuum inlet 154 is open for flow from the storage chamber 140 to the vacuum source 156. Thus, once the seal 76 opens the vacuum inlet 154, the vacuum source 156 may draw fluid (e.g., air and/or liquid) from the storage chamber 140 so that fluid in the channel 110 is drawn into the storage chamber 140. Although not shown, a hydrophobic membrane or other suitable element may be provided at the vacuum inlet 154 or other suitable location (such as in the passage 150) to prevent liquid from flowing from the storage chamber 140 into the vacuum source 156.

In accordance with one aspect of the invention, fluid communication between the fluid transporter opening and the vacuum source may be enabled in response to actuation of the flow activator or prior to actuation of the flow activator. For example, depression of the device actuator 10 may permit communication between the vacuum source 156 and the storage chamber 140/opening 130. While other arrangements are possible, in the illustrative embodiment of FIGS. 1-10, the seal 76 may be coupled to the seal leg 49 of the retraction actuator 40 so that once the flow activator 90 is actuated, e.g., deployment and retraction are initiated, the seal 76 may be released from the vacuum inlet 154 to permit fluid communication between the vacuum source 156 and the storage chamber 140. Although in this embodiment, the seal leg 49 of the retraction actuator 40 moves away from the vacuum inlet 154 (or at least reduces a pressure on the seal 76) as the flow activator 90 is retracted, it is possible to arrange the opening of the seal 76 upon deployment of the flow activator 90 or at any other point in the movement of the flow activator 90, as well as before movement begins or after movement is completed. For example, flow between the vacuum source 156 and the storage chamber 140 may be enabled by piercing a membrane or foil, e.g., with deployment of the flow activator 90 or upon full retraction of the flow activator 90. In one embodiment, a membrane seal could be located at the opening 130, and the flow activator 90 itself could serve to puncture the membrane, allowing flow from the opening 130 to the vacuum source 156. Thus, this puncture could serve to expose fluid at the opening 130 to vacuum to draw the fluid into a storage chamber 140. Of course, a membrane seal may be positioned at locations other than the opening 130, such as at the vacuum inlet 154, and a separate piercing element, such as a spike on the release element 30, could be used to puncture the membrane. Other arrangements are possible as well, such as actuating a vacuum source (such as a chemical vacuum source or vacuum pump) in response to flow activator actuation. For example, the retraction actuator 40 may be coupled to a syringe piston so that as the retraction actuator 40 moves in the retraction direction, the piston is moved to generate suction at the storage chamber 140.

As will be appreciated from the description above, in another aspect of the invention, the flow activator may be moved in a deployment direction to deploy the flow activator, and moved in a retraction direction to both retract the flow activator and enable fluid communication between the vacuum source and a fluid transporter opening. In the illustrative embodiment described above, the seal 76 may be released from the vacuum inlet 154 as the flow activator 90 is retracted. Opening of the flow path at the seal 76 may occur at the start of retraction, during retraction, and/or after retraction is complete. In some embodiments, the seal 76 and flow activator 90 may be both moved in the same retraction direction by the retraction actuator. That is, during retraction, the flow activator 90 may be retracted and the seal 76 lifted to enable fluid communication between the vacuum source 156 and the device opening 130 through a channel 110. The seal 76 may be formed from or otherwise include latex or other flexible material such as a thermoplastic elastomer (TPE) or polyurethane. In other embodiments, a force on the seal 76 may be sufficiently released to allow the relatively low pressure in the vacuum source 156 to cause flow from the storage chamber 140 to the vacuum source 156 to occur. Thus, the seal 76 need not necessarily be lifted from the vacuum inlet 154, but instead may act as a kind of check valve with a desired crack pressure that permits flow from the storage chamber 140 to the vacuum source 156 while a suitable pressure differential is present across the seal 76, but otherwise inhibits flow through the inlet 154. Other arrangements for opening fluid communication during retraction of the flow activator are possible, such as a spike on the retraction actuator 40 that pierces a membrane to open the fluid communication. In another embodiment, an electrical switch may be opened or closed by the retraction actuator, causing a vacuum source (such as a pump) to be activated. In another embodiment, movement of the retraction actuator may release a latch or other device, which allows a spring-loaded syringe piston or other device to move, creating a desired vacuum. In another embodiment, retraction movement of the retraction actuator 40 itself may move a syringe piston or other device to provide a desired vacuum. Thus, enabling of fluid communication between a vacuum source and a fluid transporter opening need not necessarily involve the opening of a valve or other device that blocks flow, but instead may involve the creation of suitable vacuum to cause flow. Other arrangements are possible as well.

In another aspect of the invention, an effector that deploys and/or retracts the flow activator may also enable fluid communication between the fluid transporter opening and the vacuum source. Providing a single component or assembly to both deploy and/or retract a flow activator as well as open fluid communication between a fluid transporter and vacuum source may, in some embodiments, provide for a fluid receiving device that is simpler in operation or construction. For example, a single device, such as a retraction actuator 40 in the FIGS. 1-10 embodiment, may serve to both retract and open a flow path. This may reduce parts needed for construction of the fluid receiving device, reducing cost and/or assembly complexity. Of course, the effector need not necessarily perform both deployment and retraction functions, but instead may provide only deployment or retraction together with enabling fluid communication. For example, the effector may serve to only deploy a flow activator and enable fluid communication between the fluid transporter opening and vacuum source, e.g., in an embodiment where a flow activator is not retracted after deployment, but instead is permitted to remain embedded in skin to withdraw fluid as vacuum is applied to the flow activator. As discussed above, enabling of fluid communication between the fluid transporter opening and vacuum source may be provided in different ways, such as by opening a valve or similar structure (such as the seal 76), piercing a membrane, actuating a vacuum source (such as moving a syringe plunger or similar element), activating a chemically-operated vacuum source, and so on.

In another aspect of the invention, the flow activator and the vacuum seal may be attached together, e.g., as part of a single unitary structure or component. For example, as shown in FIGS. 4 and 5, the flow activator 90 may be attached to the membrane 72, e.g., by co-molding the flow activator 90 with the membrane, adhering the flow activator 90 to the membrane, etc., while the seal 76 is formed from part of the membrane 72 itself. Such an arrangement may ease assembly and reduce the number of components in the fluid receiving device 1. As discussed above, flow enabled by movement of the seal 76 may cause flow along the channel 110 to the storage chamber 140. The channel 110 may be formed, at least in part, by a single component, e.g. an etched substrate or molded unit such as the base 100. The channel can have any cross-sectional shape, for example, circular, oval, triangular, irregular, square or rectangular (having any aspect ratio), or the like, and can be covered or uncovered (i.e., open to the external environment surrounding the channel). The channel 110 may be of any length. In some cases, the channel 110 can be a simple two-dimensional opening that creates a fluidic coupling between the opening 130 and another vessel such as a vacuum source or a storage vessel. In these cases, the channel may not have any length at all (e.g., as in a two-dimensional opening). In embodiments where the channel is completely covered, at least one portion of the channel can have a cross-section that is completely enclosed, and/or the entire channel may be completely enclosed along its entire length with the exception of its inlet and outlet.

A channel may have any aspect ratio (length to average cross-sectional dimension), e.g., an aspect ratio of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

Fluids received from the skin and/or from beneath the skin of the subject will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. Still other analytes include, but not limited to, high-density lipoprotein ("HDL"), low-density lipoprotein ("LDL"), albumin, alanine transaminase ("ALT"), aspartate transaminase ("AST"), alkaline phosphatase ("ALP"), bilirubin, lactate dehydrogenase, etc. (e.g., for liver function tests); luteinizing hormone or beta-human chorionic gonadotrophin (hCG) (e.g., for fertility tests); prothrombin (e.g., for coagulation tests); troponin, BNT or B-type natriuretic peptide, etc., (e.g., as cardiac markers); infectious disease markers for the flu, respiratory syncytial virus or RSV, etc.; or the like.

The fluid receiving device 1 may include one or more sensors for detecting one more characteristics of a fluid received from a subject. The sensor(s) may be located in any suitable way or location with respect to the device, such as at the storage chamber 140, at the channel 110, on the cover 20, etc. For example, the device 1 may include a pH sensor, an optical sensor, an oxygen sensor, a sensor able to detect the concentration of a substance, or the like. Non-limiting examples of sensors useful in the invention include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other suitable sensors. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

In one set of embodiments, the sensor may be a test strip, for example, test strips that can be obtained commercially. Examples of test strips include, but are not limited to, glucose test strips, urine test strips, pregnancy test strips, or the like. A test strip will typically include a band, piece, or strip of paper or other material and contain one or more regions able to determine an analyte, e.g., via binding of the analyte to a diagnostic agent or a reaction entity able to interact with and/or associate with the analyte. For example, the test strip may include various enzymes or antibodies, glucose oxidase and/or ferricyanide, or the like. The test strip may be able to determine, for example, glucose, cholesterol, creatinine, ketones, blood, protein, nitrite, pH, urobilinogen, bilirubin, leucocytes, luteinizing hormone, etc., depending on the type of test strip. The test strip may be used in any number of different ways. In some cases, a test strip may be obtained commercially and inserted into the device, e.g., before or after receiving blood, interstitial fluid, or other fluids from a subject. At least a portion of the blood or other fluid may be exposed to the test strip to determine an analyte, e.g., in embodiments where the device uses the test strip as a sensor so that the device itself determines the analyte. In some cases, the device may be sold with a test strip pre-loaded, or a user may need to insert a test strip in a device (and optionally, withdraw and replace the test strip between uses). In certain cases, the test strip may form an integral part of the device that is not removable by a user. In some embodiments, after exposure to the blood or other fluid withdrawn from the subject, the test strip may be removed from the device and determined externally, e.g., using other apparatuses able to determine the test strip, for example, commercially-available test strip readers.

In some embodiments, the device may include a separation membrane that is impermeable to blood cells and other substances. Fluid received from the subject may flow through a separation membrane, and the received fluid may include components of various sizes. For example, the device may receive blood that includes blood cells, clotting factors, proteins, and blood plasma, among other components. Larger components such as blood cells and other larger substances may not be able to pass through the separation membrane while blood plasma is free to pass. In some embodiments, this blood plasma is collected into a storage chamber. If anticoagulant is not introduced to the blood plasma, the blood plasma, which contains clotting factors such as fibrinogen, may clot, thereby resulting in a solid clot component and a liquid component. This liquid component is known as serum, which is blood plasma without fibrinogen or other clotting factors. This serum can be collected via aspiration or other suitable method out of the storage chamber, leaving the blood clots in the storage chamber. If anticoagulant is introduced to the blood plasma, the blood plasma will not clot and blood plasma can be collected out of the storage chamber instead. Thus, the embodiments described throughout the specification may be used to produce plasma or serum. More details regarding plasma and serum production can be found in U.S. and international patent applications each entitled "Plasma or Serum Production and Removal of Fluids Under Reduced Pressure," filed on even date herewith, incorporated herein by reference in its entireties. Also incorporated herein by reference in its entirety is U.S. provisional Patent Application Ser. No. 61/480,941, entitled "Plasma or Serum Production and Removal of Fluids Under Reduced Pressure," by Haghgooie, et. al., filed on Apr. 29, 2011.

In some embodiments, the device may be connected to an external apparatus for determining at least a portion of the device, a fluid removed from the device, an analyte suspected of being present within the fluid, or the like. For example, the device may be connected to an external analytical apparatus, and fluid removed from the device for later analysis, or the fluid may be analyzed within the device in situ, e.g., by adding one or more reaction entities to the device, for instance, to a storage chamber, or to analytical chamber within the device. In some embodiments, assay disks 200 or membranes may be included in storage chamber 140, as shown in FIG. 4. In one embodiment, the external apparatus may have a port or other suitable surface for mating with a port or other suitable surface on the device, and blood, interstitial fluid, or other fluid can be removed from the device using any suitable technique, e.g., using vacuum or pressure, etc. The blood or other fluid may be removed by the external apparatus, and optionally, stored and/or analyzed in some fashion. For example, in one set of embodiments, the device may include an exit port for removing a fluid from the device (e.g., blood). In some embodiments, fluid contained within a storage chamber in the device may be removed from the device, and stored for later use or analyzed outside of the device. In some cases, the exit port may be separate from the fluid transporter. In some cases, an exit port can be in fluidic communication with a vacuum source, which can also serve as a fluid reservoir in some cases. Other methods for removing blood, interstitial fluid, or other fluids from the device include, but are not limited to, removal using a vacuum line, a pipette, extraction through a septum instead of an exit port, or the like. In some cases, the device may also be positioned in a centrifuge and subjected to various g forces (e.g., to a centripetal force of at least 50 g), e.g., to cause at separation of cells or other substances within a fluid within the device to occur.

The device may include an anticoagulant or a stabilizing agent for stabilizing the fluid withdrawn from the skin and/or beneath the skin. As a specific non-limiting example, an anticoagulant may be used for blood withdrawn from the skin. Examples of anticoagulants include, but are not limited to, heparin, citrate, thrombin, oxalate, ethylenediaminetetraacetic acid (EDTA), sodium polyanethol sulfonate, acid citrate dextrose. Other agents may be used in conjunction with or instead of anticoagulants, for example, stabilizing agents such as solvents, diluents, buffers, chelating agents, enzyme inhibitors (ie. Protease or Nuclease inhibitor), antioxidants, binding agents, preservatives, antimicrobials, or the like. Examples of preservatives include, for example, benzalkonium chloride, chlorobutanol, parabens, or thimerosal. Non-limiting examples of antioxidants include ascorbic acid, glutathione, lipoic acid, uric acid, carotenes, alpha-tocopherol, ubiquinol, or enzymes such as catalase, superoxide dismutase, or peroxidases. Examples of microbials include, but are not limited to, ethanol or isopropyl alcohol, azides, or the like. Examples of chelating agents include, but are not limited to, ethylene glycol tetraacetic acid or ethylenediaminetetraacetic acid. Examples of buffers include phosphate buffers such as those known to ordinary skill in the art.

In one set of embodiments, at least a portion of the device may be colored to indicate the anticoagulant(s) contained within the device. In some cases, the colors used may be identical or equivalent to that commercially used for Vacutamers™, Vacuettes™, or other commercially-available phlebotomy equipment. For example, lavender and/or purple may indicate ethylenediaminetetraacetic acid, light blue may indicate citrate, dark blue may indicate ethylenediaminetetraacetic acid, green may indicate heparin, gray may indicate a fluoride and/or an oxalate, orange may indicate a thrombin, yellow may indicate sodium polyanethol sulfonate and/or acid citrate dextrose, black may indicate citrate, brown may indicate heparin, etc. In other embodiments, however, other coloring systems may be used.

Other coloring systems may be used in other embodiments of the invention, not necessarily indicative of anticoagulants. For example, in one set of embodiments, the device carries a color indicative of a recommended bodily use site for the device, e.g., a first color indicative of a device suitable for placement on the back, a second color indicative of a device suitable for placement on a leg, a third color indicative of a device suitable for placement on the arm, etc.

As mentioned, in one set of embodiments, a device of the invention as discussed herein may be shipped to another location for analysis. In some cases, the device may include an anticoagulant or a stabilizing agent contained within the device, e.g., within a storage chamber for the fluid. Thus, for example, fluid such as blood or interstitial fluid withdrawn from the skin and/or beneath the skin may be delivered to a chamber (e.g., a storage chamber) within the device, then the device, or a portion of the device (e.g., a module) may be shipped to another location for analysis. Any form of shipping may be used, e.g., via mail.

Alternative Embodiments

Alternative embodiments that may incorporate one or more aspects of the invention are discussed further below.

Figure 11:
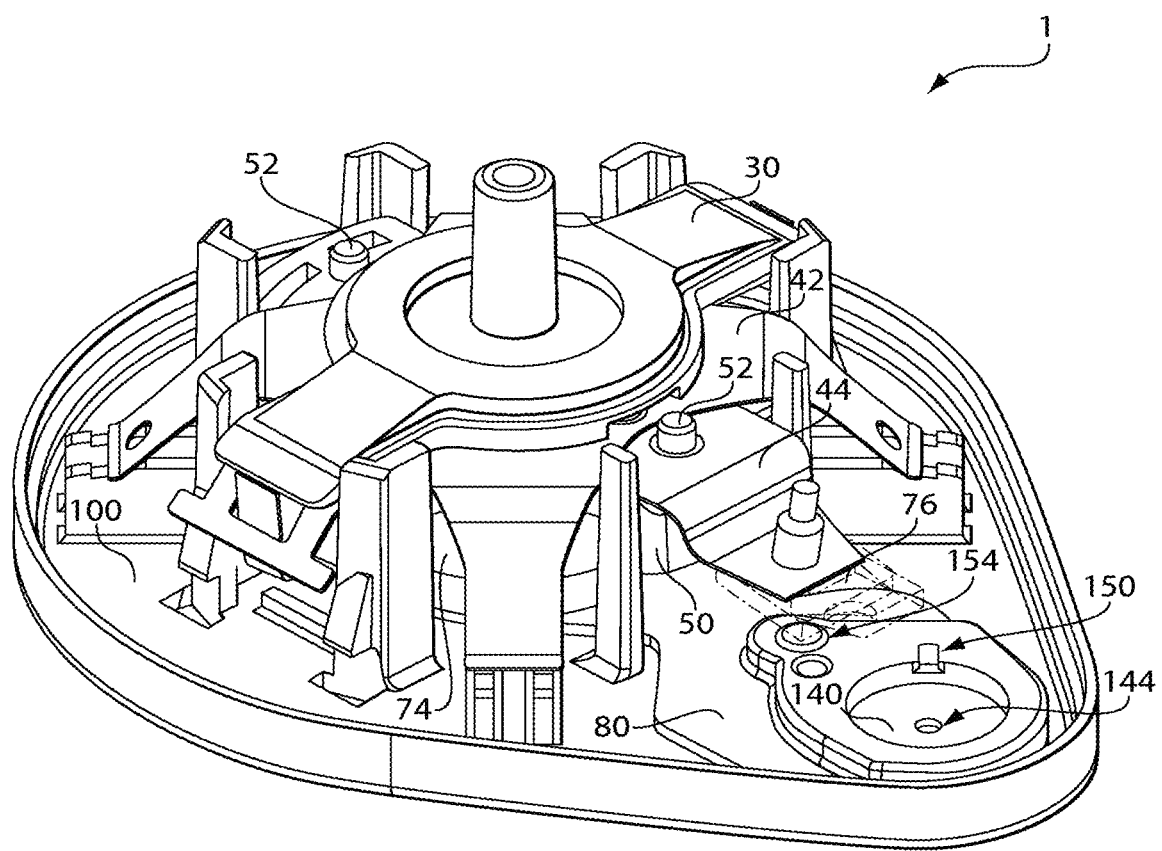
FIG. 11 is a perspective view of a device in another embodiment of the invention, having separate retractor and seal actuator portions.
Figure 12:
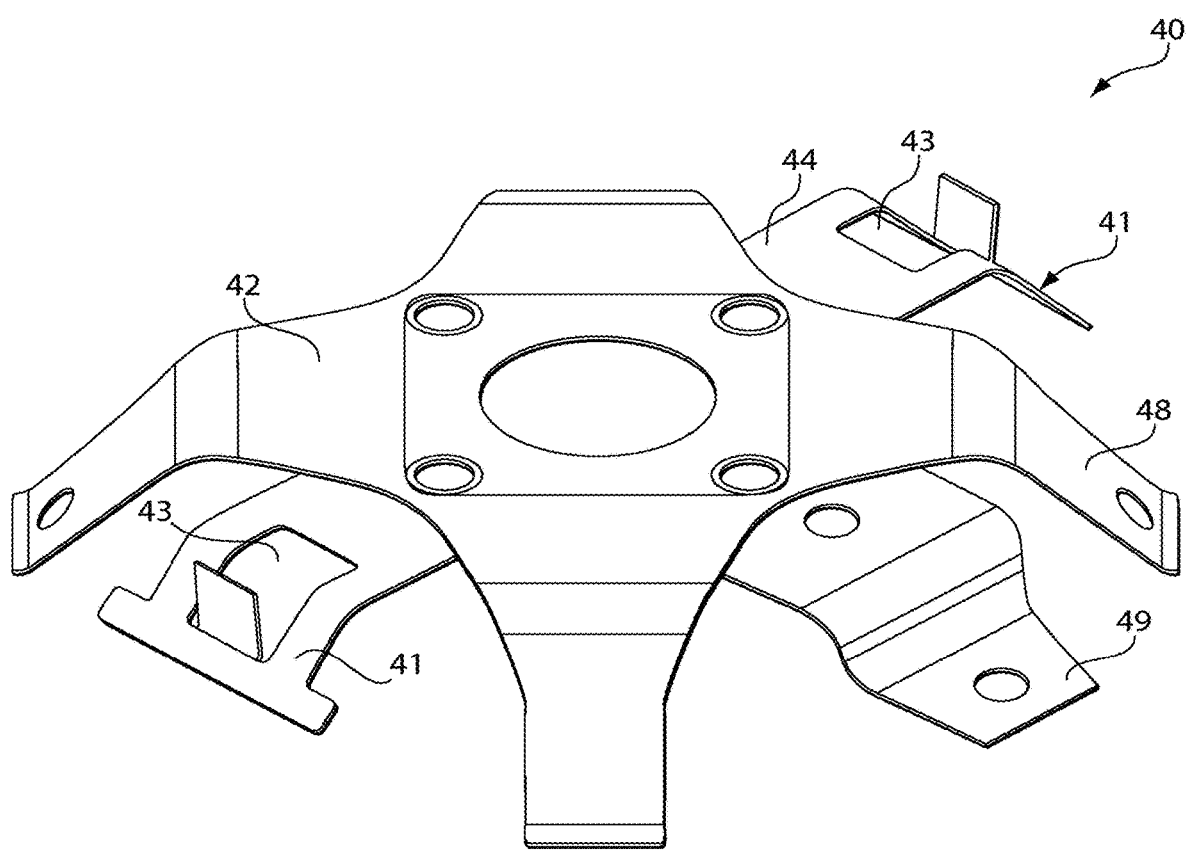
FIG. 12 is an enlarged view of the retractor portion and seal actuator portion in the device shown in FIG. 11.
Figure 13:
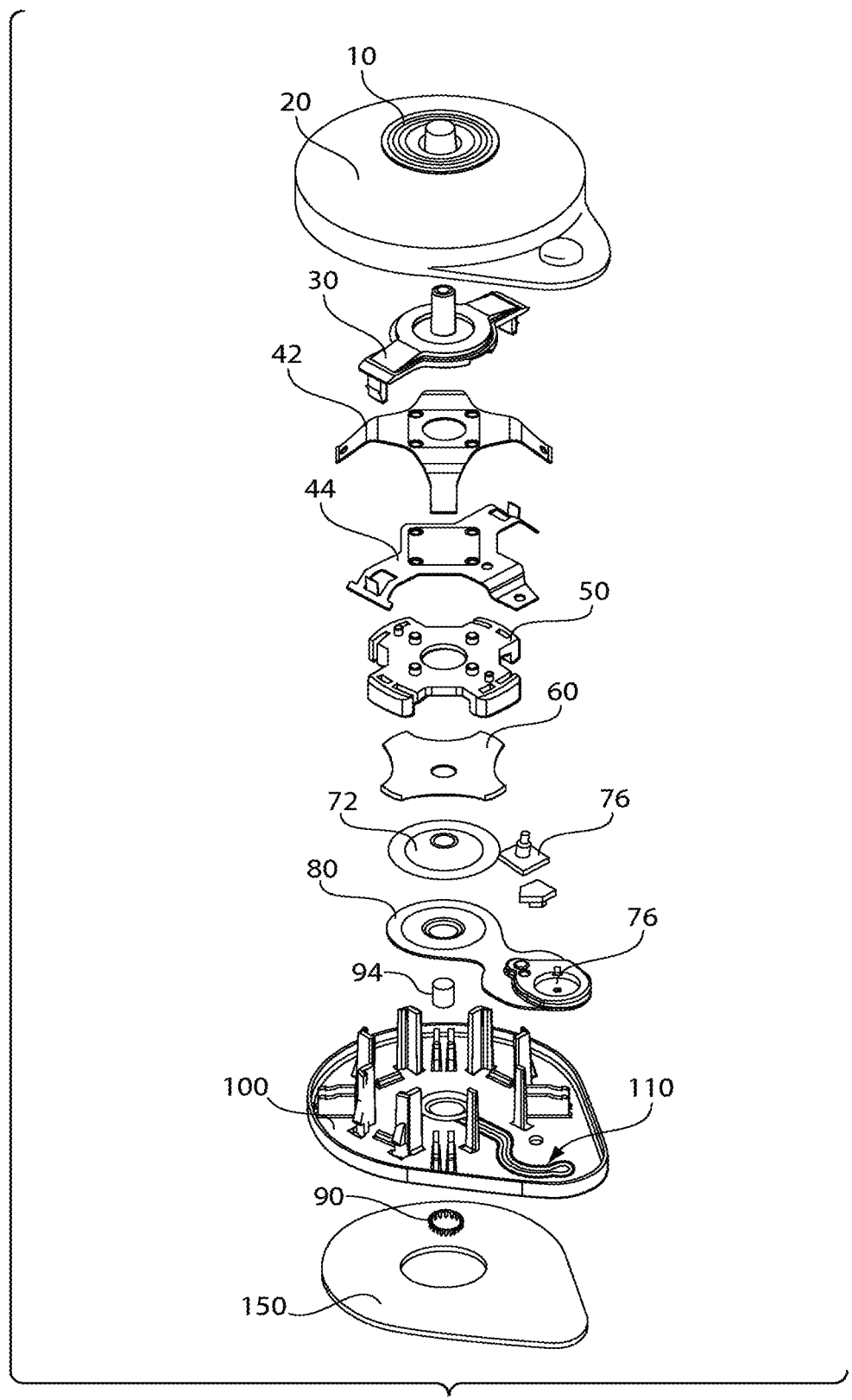
FIG. 13 is an exploded view of the device shown in FIG. 11.
Figure 14:
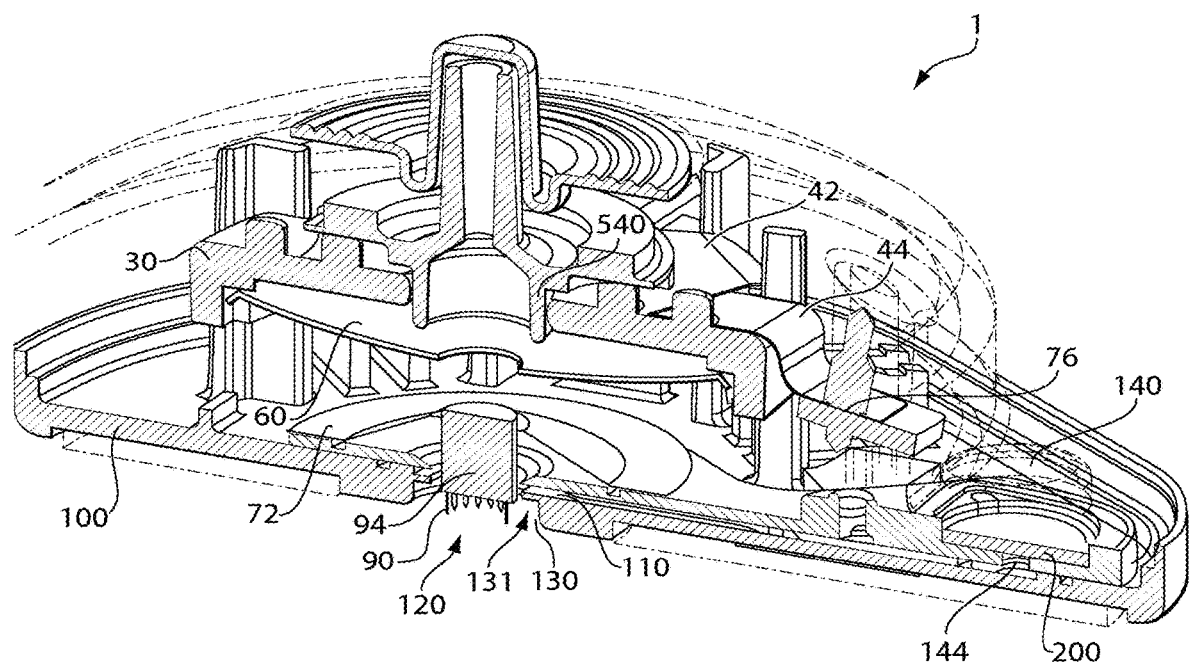
FIG. 14 is a cross-sectional view of the device shown in FIG. 11.
Figure 15:
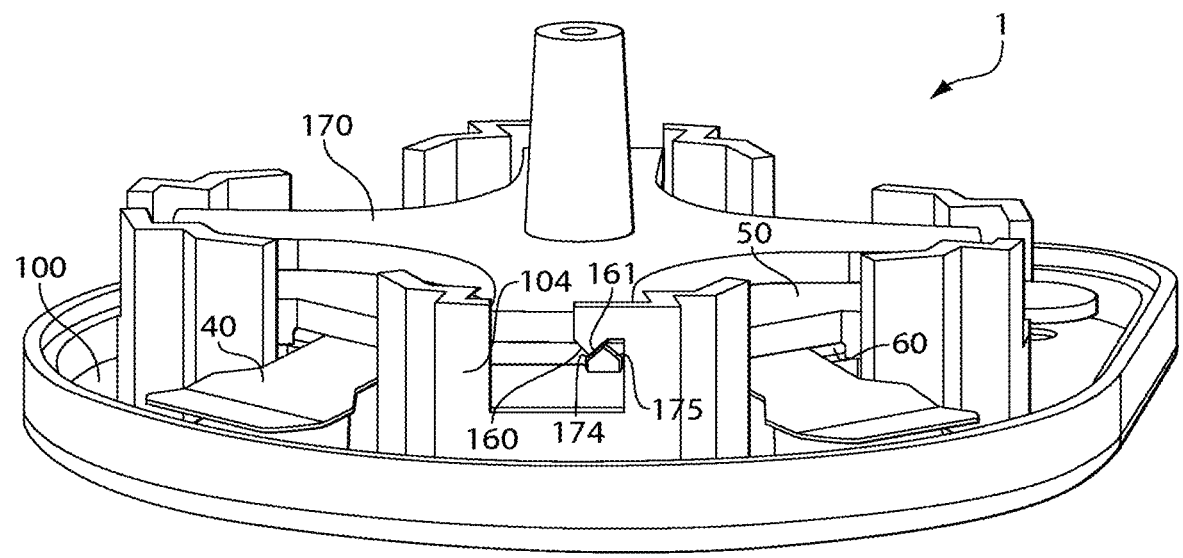
FIG. 15 is a perspective view of a device in yet another embodiment of the invention with the cover removed and having a rotatable release element.
Figure 16:
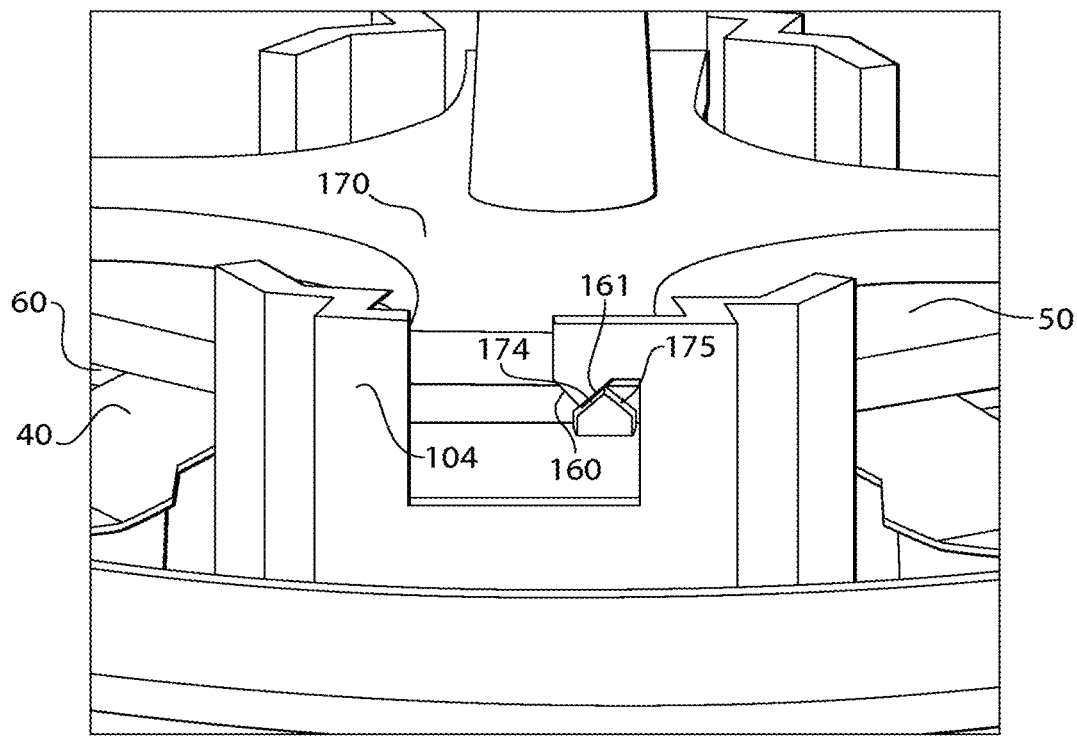
FIG. 16 is an enlargement of a ramp engagement region in the device shown in FIG. 15.
Figure 17:
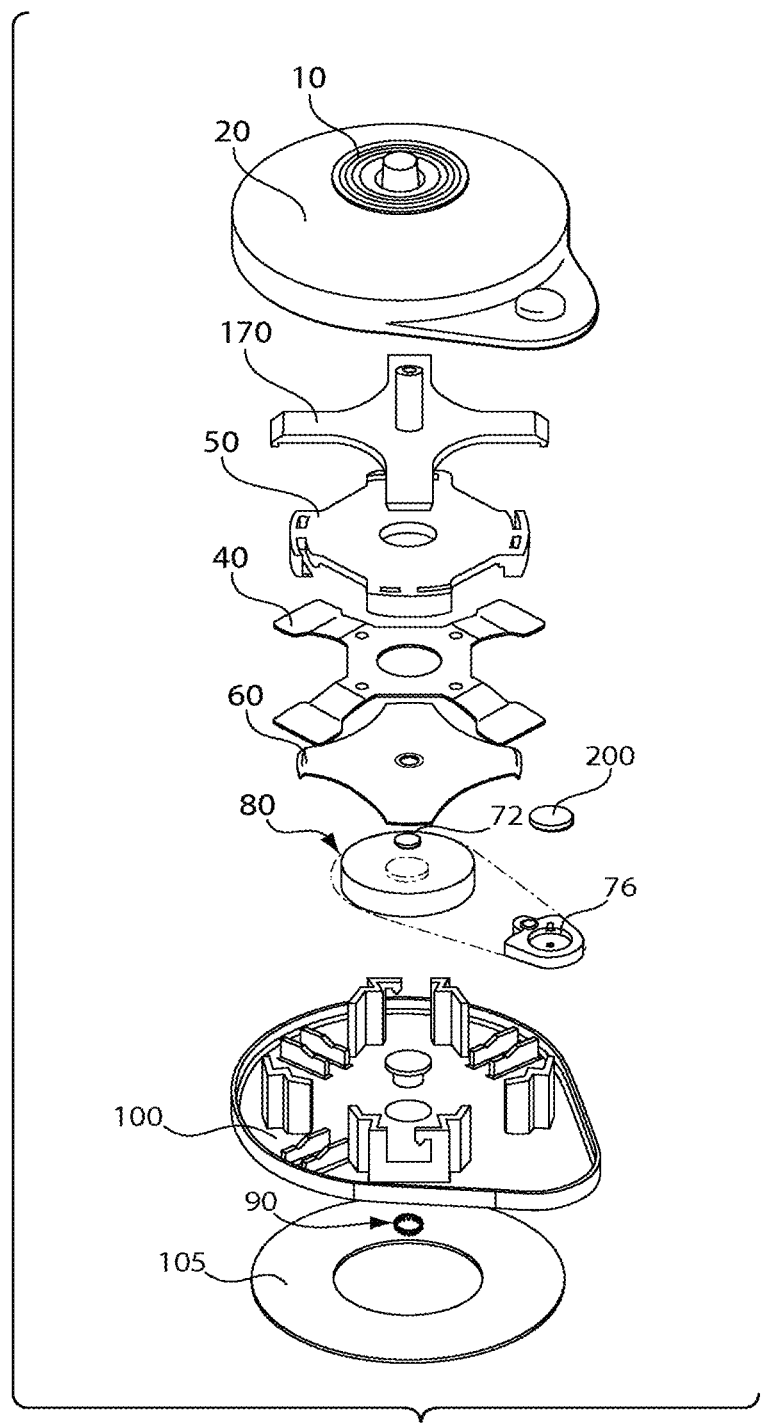
FIG. 17 is an exploded view of the device shown in FIG. 15.
Figure 18:
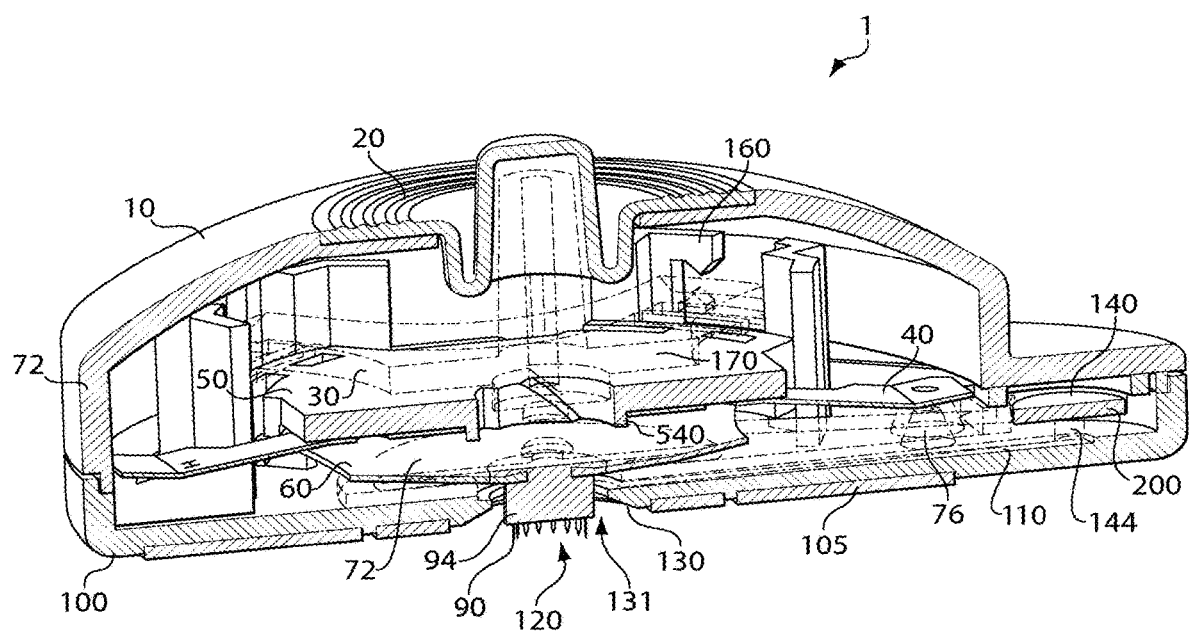
FIG. 18 is a cross-sectional view of the device shown in FIG. 15.
Figure 19:
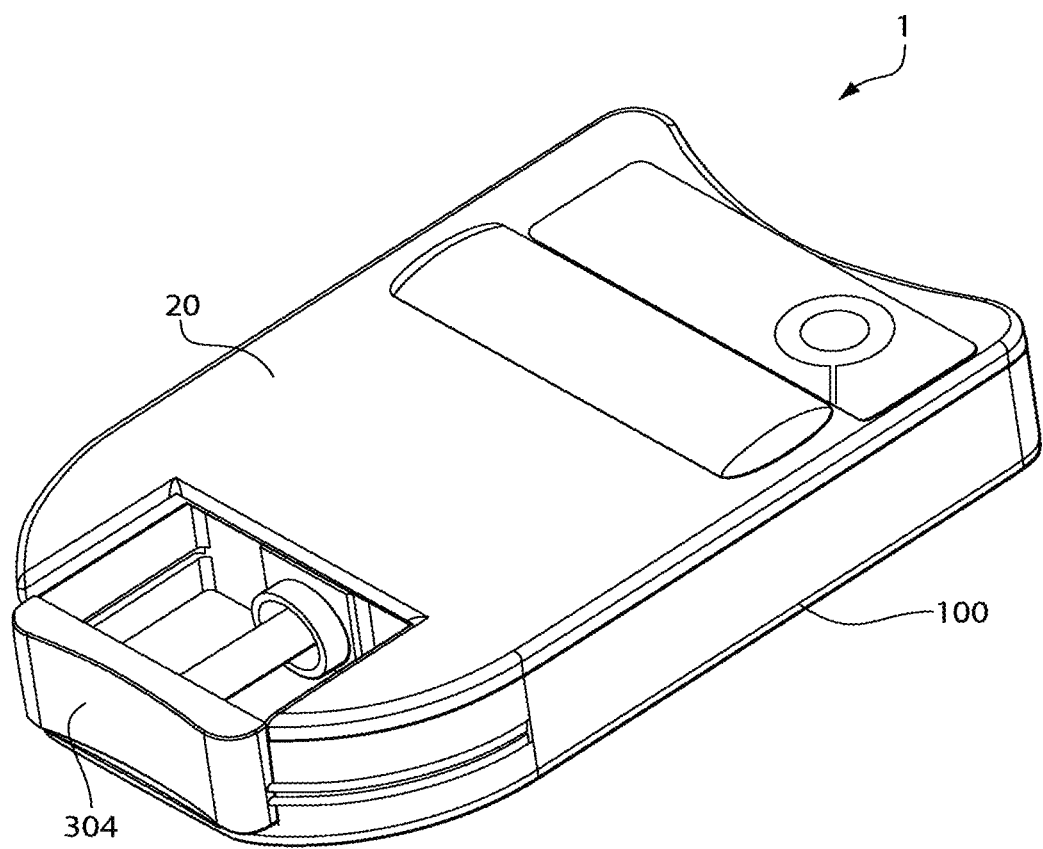
FIG. 19 is a perspective view of a device in yet another embodiment of the invention, having a sliding trigger tip.
Figure 20:
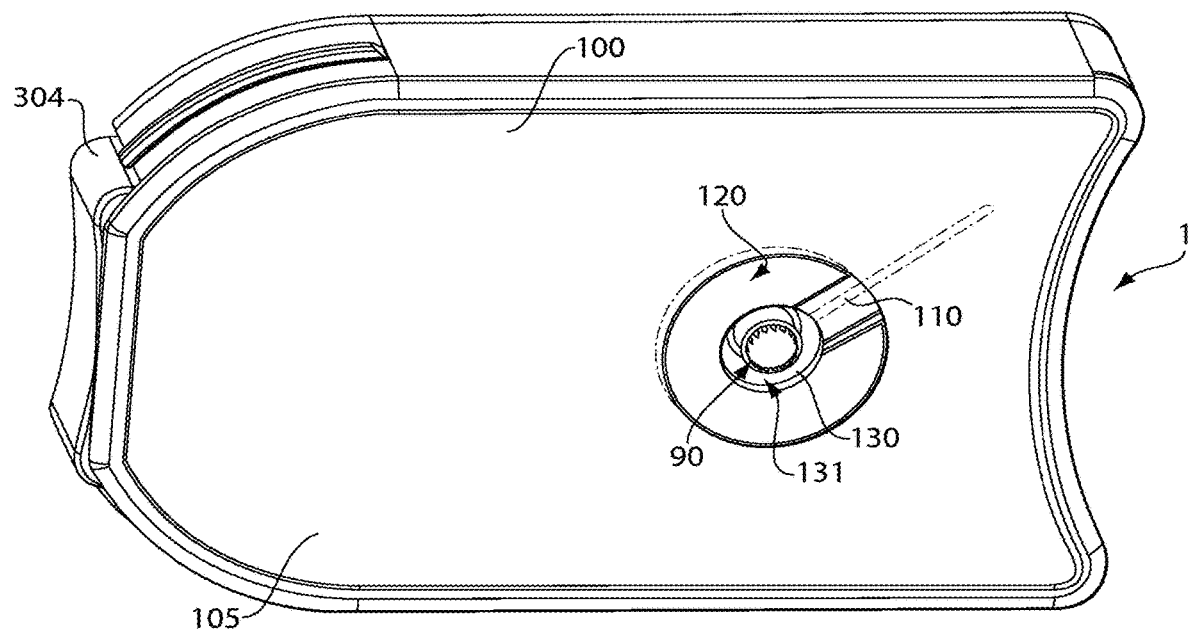
FIG. 20 is a perspective view of the underside of the device shown in FIG. 19.
Figure 21:
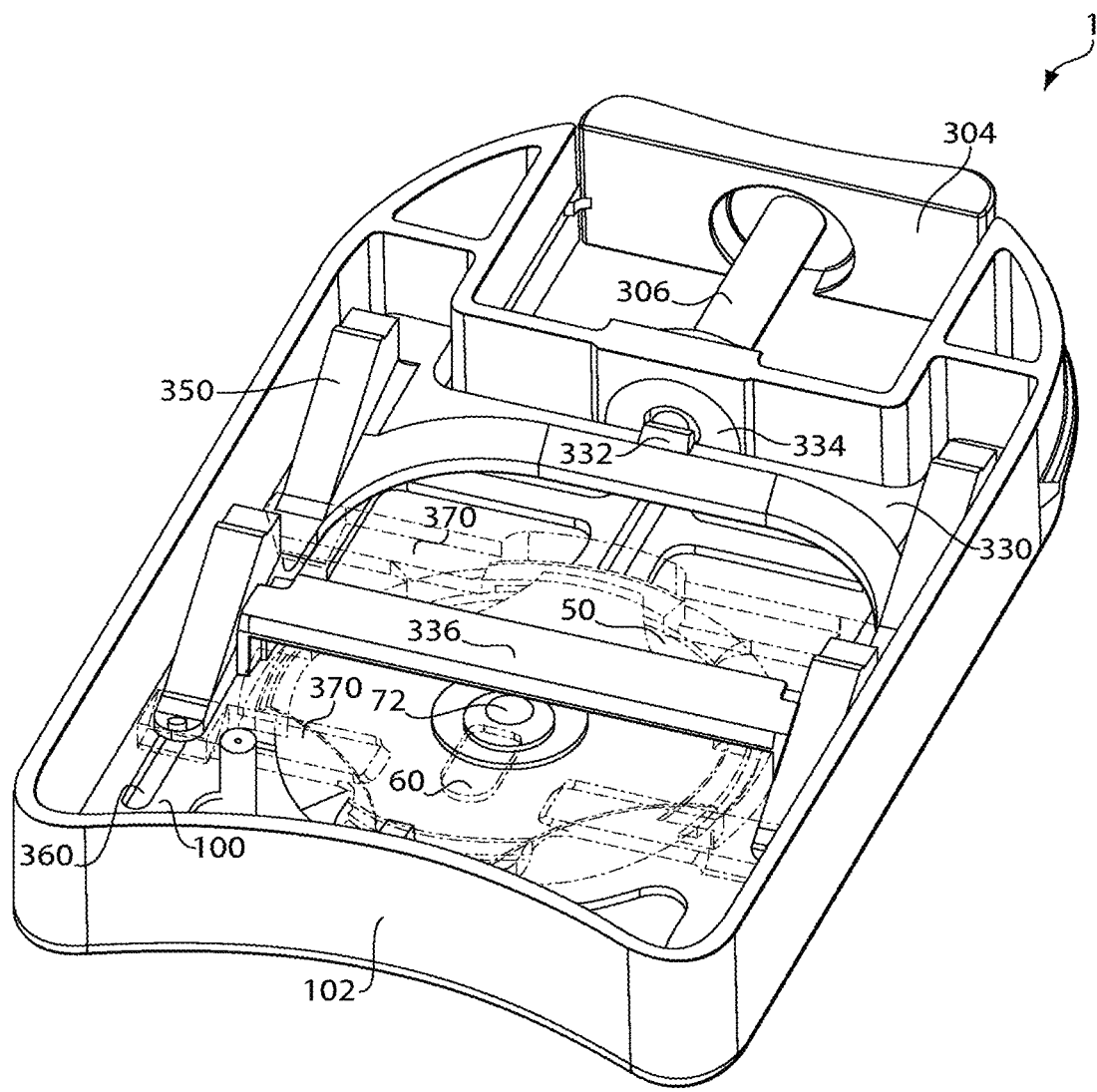
FIG. 21 is a perspective view of the device shown in FIG. 19 with the cover removed.
Figure 22:
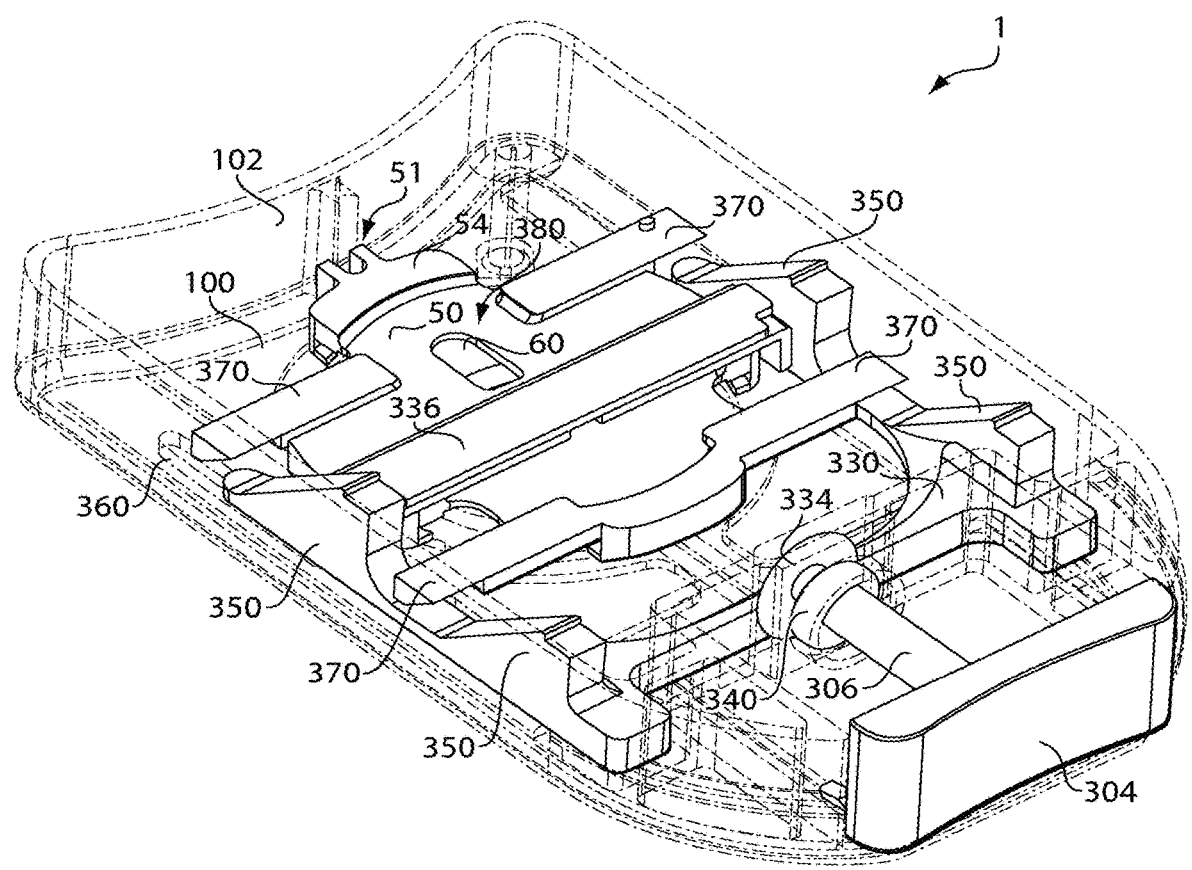
FIG. 22 is a perspective view of the device shown in FIG. 19 with the cover removed and at a different angle than the view shown in FIG. 21.
Figure 23A:
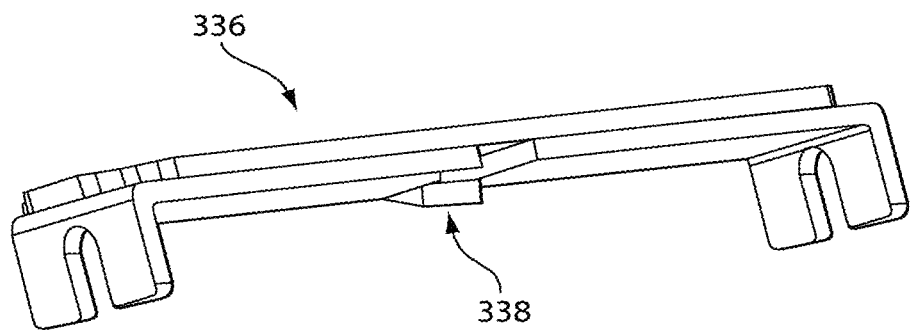
FIG. 23A is an enlargement of a trigger bridge from the device shown in FIG. 22.
Figure 23B:
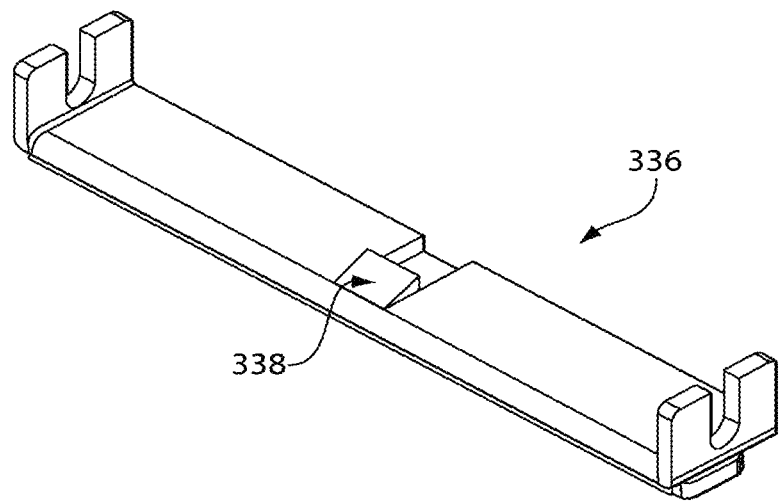
FIG. 23B is a perspective view of the underside of the enlargement shown in FIG. 23A.
Figure 24:
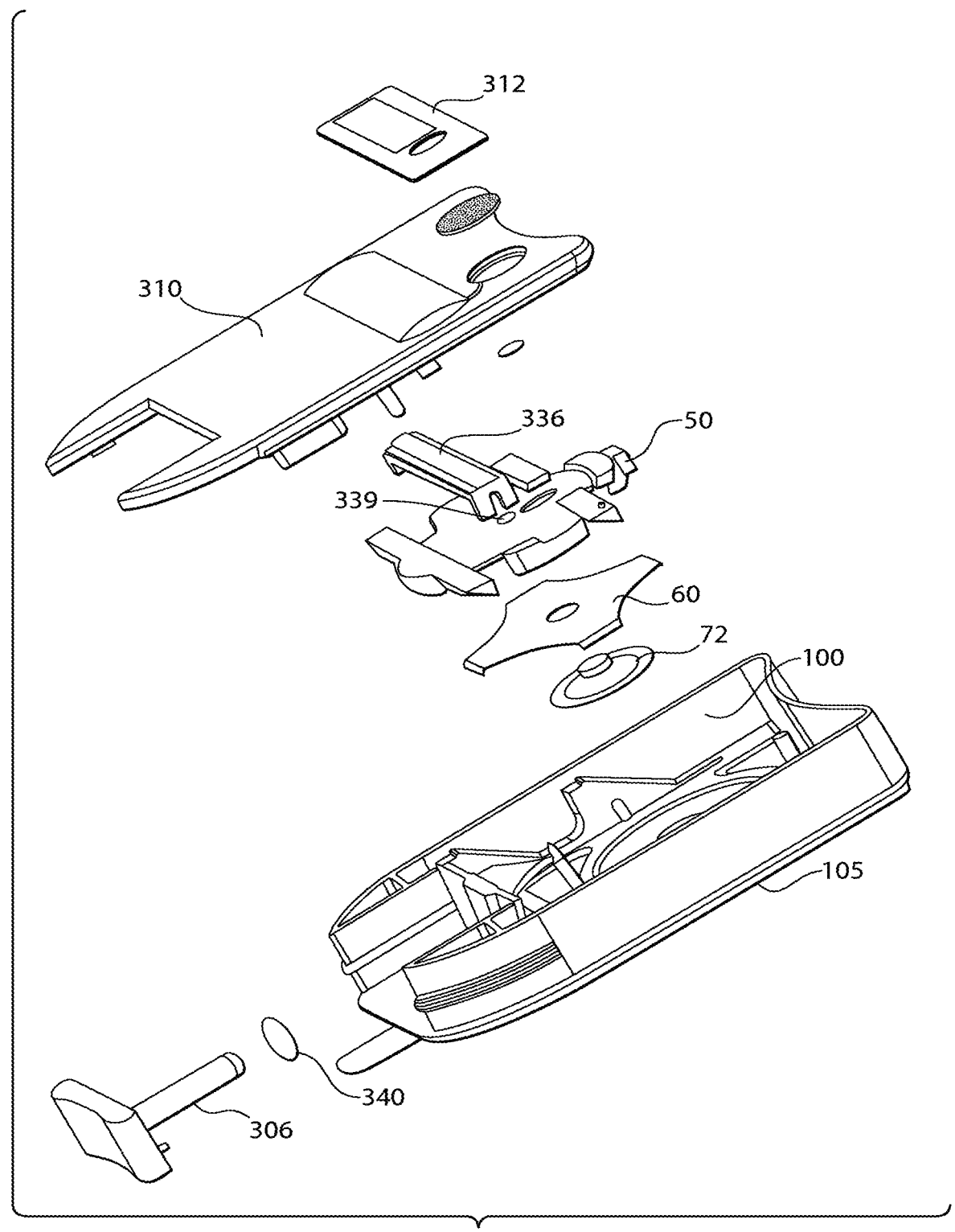
FIG. 24 is an exploded view of the device shown in FIG. 19.
Figure 25:
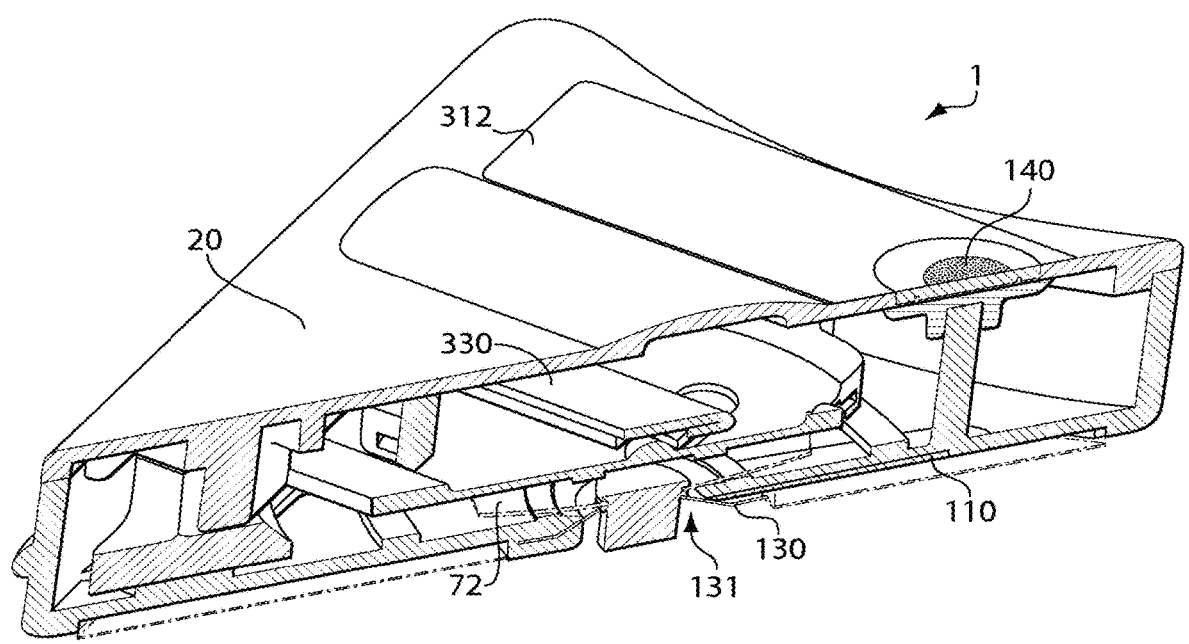
FIG. 25 is a cross-sectional view of the device shown in FIG. 19.

It should be understood that various components of a fluid receiving device may be modified in different ways, and that the embodiment discussed with respect to FIGS. 1-10 should not be used to limit aspects of the invention. For example, in one alternative embodiment, the retraction actuator 40 of a device 1 may include two separate elements. FIGS. 11-14 show an embodiment in which the retraction actuator 40 includes a retractor portion 42 and a seal actuator portion 44. As shown in FIGS. 11 and 12, the retractor portion 42 and the seal actuator portion 44 are stacked and coupled to the effector body 50 via five posts 52. Any number of posts may be used. The post 52 may be formed from or otherwise include Polyester (PCTA or PETG) or other polymer such as ABS, acetal resin, polystyrene, etc. Alternatively, the retractor portion 42 and the seal actuator portion 44 may be coupled to the effector body 50 via a single post, glue, tape, other adhesive, etc. FIG. 12 shows that the retractor portion 42 includes legs 48 that are free to flex relative to the effector 50. The seal actuator portion 44 includes tabs 41 and the seal leg 49 that is coupled to the seal 76. Both the retractor portion 42 and a seal actuator portion 44 otherwise have essentially the same features as the retraction actuator 40 described above. By separating the retraction actuator 40 into two portions, each may be designed and constructed to have desired features. For example, in some embodiments it may be desirable to have the legs 48 made of a highly elastic material, whereas the tabs 41 and seal leg 49 may be made of a less elastic material, e.g., to help release the seal 76 as the retraction actuator 40 moves upwardly. Additionally, as shown in FIG. 13, the membrane 72 may be made independent from the seal 76, e.g., the seal 76 may be formed as part of the seal leg 49 of the actuator 40. In some embodiments, the flow activator 90 may be mechanically coupled to the deployment actuator 60 via a transmission structure 94 such as a post, a rod, or other. As shown in FIG. 13, a post 94 is coupled to the membrane 72, the flow activator 90 and the deployment actuator 60, and may be made relatively stiff or non-compliant, e.g., to help transmit movement from the deployment actuator 60 to the flow activator 90 with little loss. FIGS. 15-18 show yet another embodiment that is very similar to that of FIGS. 1-10, but in which the latch arrangement used to hold the retraction actuator 40 in an initial, compressed state is modified. In this illustrative embodiment, the device 1 contains a rotatable release element 170 that rotates relative to the base 100 during operation of the device. (The rotatable release element 170 and corresponding portions of the base 100 replace the release element 30 and the tabs 41 of the retraction actuator 40 of the FIGS. 1-10 embodiment.) A spinner ramp 174 of the release element 170 initially engages with a lock-out ramp 161 of an effector guide 104 and holds the rotatable release element 170 in place prior to actuation of the device 1. FIG. 16 shows a close-up of the initial engagement prior to actuation of the device 1. However, when the rotatable release element 170 is moved toward the base 100 during device actuation (e.g., depression of the device actuator 10), the release element 170 rotates slightly so that the spinner ramp 174 slides and clears the lock-out ramp 161 as the release element 170 moves towards the base 100. (Slight rotation of the release element 170 may be caused by a ramp or other angled surface on the element 170 contacting a corresponding ramp or other surface of the base 100 so that downward movement of the release element 170 upon actuation of the device actuator 10 causes the desired rotation.) Thereafter, when pressure on the release element 170 is released by the user, the spinner release ramp 175 engages the base release ramp 160 as the release element 170 moves upward so that as the rotatable release element 170 rotates so that the spinner release ramp 175 clears the base release ramp 160. This may allow the retraction actuator 40 to retract, e.g., to retract the flow activator 90. In yet other embodiments, a fluid receiving device 10 may be arranged in other ways, as suggested above. For example, in one embodiment shown in FIGS. 19-25, a fluid receiving device 1 includes a horizontally sliding trigger 304 that can be actuated by a user or other by finger depression. Similar to the embodiments described above and as shown in FIGS. 19 and 20, the device 1 includes a cover 20 and a base 100, and fluid received at an opening 130 of a fluid transporter 120 may be conducted by a channel 110 to a storage chamber 140 (not shown). FIGS. 21 and 22 show internal components of the device 1. An O-ring seal 340 may be located on a trigger shaft 306 of the trigger 304. In another embodiment, a deformable membrane could form the seal. During use, sliding the trigger 304 rearwardly towards a trailing edge 102 of the base 100 causes the trigger shaft 306 to push the trigger pin 332 with a trigger pin cover 334 (see FIG. 22). This motion causes a carriage 330 to slide rearwardly along guides 360 (See FIG. 21) on the base 100 toward the trailing end 102 of the base 100. The guides 360 may be etched into the base 100, may be protruded from the base 100, or have any other suitable arrangement. As the carriage 330 moves rearwardly, a trigger bridge 336 connected to the carriage 330 moves rearwardly relative to the effector body 50. The underside of the trigger bridge 336 includes a trigger tab 338, as can be seen in FIGS. 23A and 23B. The trigger tab 338 engages with a protrusion 339 (see FIG. 24) on the top of the effector body 50 so that as the trigger bridge 336 moves rearwardly, the trigger tab 338 moves the effector body 50 downwardly a sufficient amount to actuate a deployment actuator 60, which has a configuration like that in the embodiments described above. This causes the deployment actuator 60 to deploy the flow activator 90, e.g., to extend needles from the opening 130. Continued movement of the carriage 330 in the rearward direction causes a retraction actuator of the trigger (in the form of wedges 350) to slide beneath lifting struts 370 on the effector body 50. As the wedges 350 slide beneath the lifting struts 370, the effector 50 is lifted upwardly away from base 100, thereby retracting the flow activator 90, which is attached to the effector body 50 via the deployment actuator 60, and membrane 72 in a way similar to the embodiments above. The trigger tab 338 may be received in an opening 380 in the effector body 50, allowing a central portion of the effector body 50 to flex upwardly and allowing further retraction of the flow activator 90.

Figure 26A:
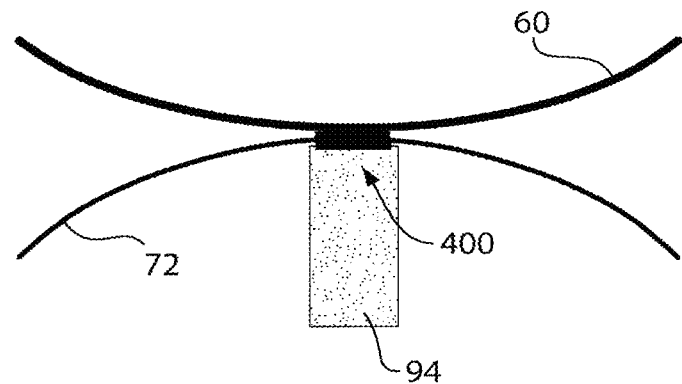
FIGS. 26A-26D show various arrangements for connecting a flow activator to a deployment actuator.
Figure 26B:
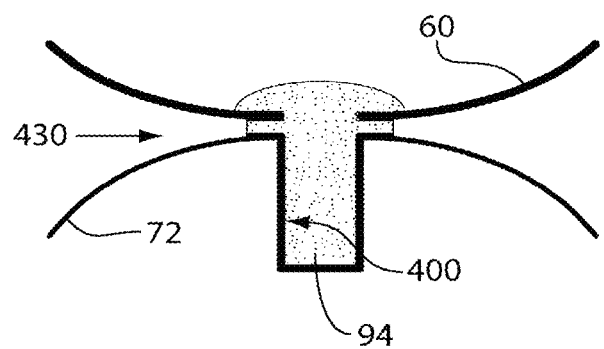
Figure 26C:
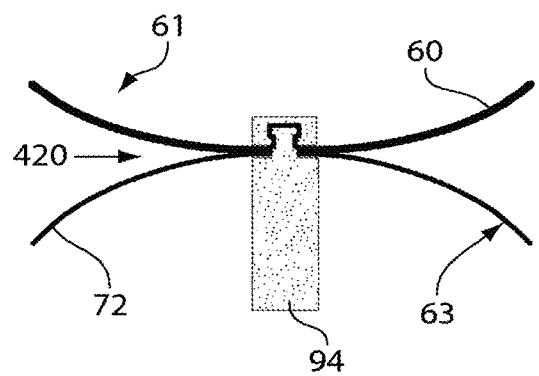
Figure 26D:
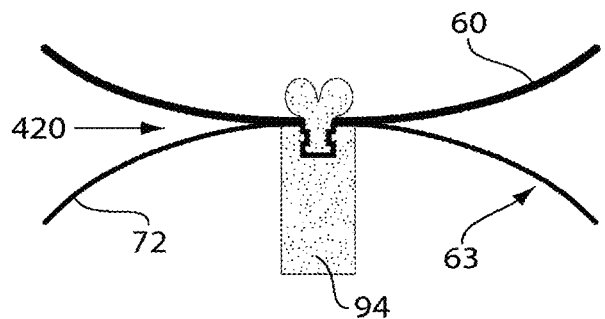

According to one aspect, connection of a flow actuator to a deployment actuator may be done in a variety of different ways, as suggested above. For example, FIG. 26A shows a schematic arrangement in which a post 94 used to connect a flow activator (not shown) to a membrane 72 and/or a deployment actuator 60 may be made by an adhesive 400. In another embodiment shown in FIG. 26B, the post 94 may be received into a cavity (or hole) in the membrane 72 as well as a hole in the deployment actuator 60. Engagement of the post 94 with the respective holes or cavities may be made in any suitable way, such as by interference or friction fit, adhesive, riveting, and so on. In this embodiment, the post 94 is engaged with a cavity of the membrane 72 by an adhesive 400 and has a rivet-type head that engages with the hole in the deployment actuator 60. The rivet head of the post 94 may be formed by plastically deforming part of the post 94, or the post 94 may include a flexible material arranged so that an upper portion of the rivet head may be resiliently deformed and forced through the hole of the actuator 60. FIG. 26C shows yet another embodiment in which a membrane 72 is joined to a deployment actuator by extending a portion of the membrane 72 through an opening in the actuator 60 and crimping or otherwise deforming the portion of the membrane 72 that extends through the opening. Alternately, a clip, band or other element may be clamped onto the membrane portion to maintain engagement of the membrane and actuator 60. The post 94 may be attached to both the membrane and actuator as part of the same process, e.g., part of the post may function as a clip or band. FIG. 26D shows an embodiment with a two part post 94 where the membrane 72 is trapped between the two parts of the post. The top part of the post extends through a hole in the deployment actuator 60 or is heat staked to create an interference fit between the post and the deployment actuator 60. A portion of the post 94 may be forced through an opening at the connection point, and thereby be engaged with the deployment actuator 60.

Figure 28:
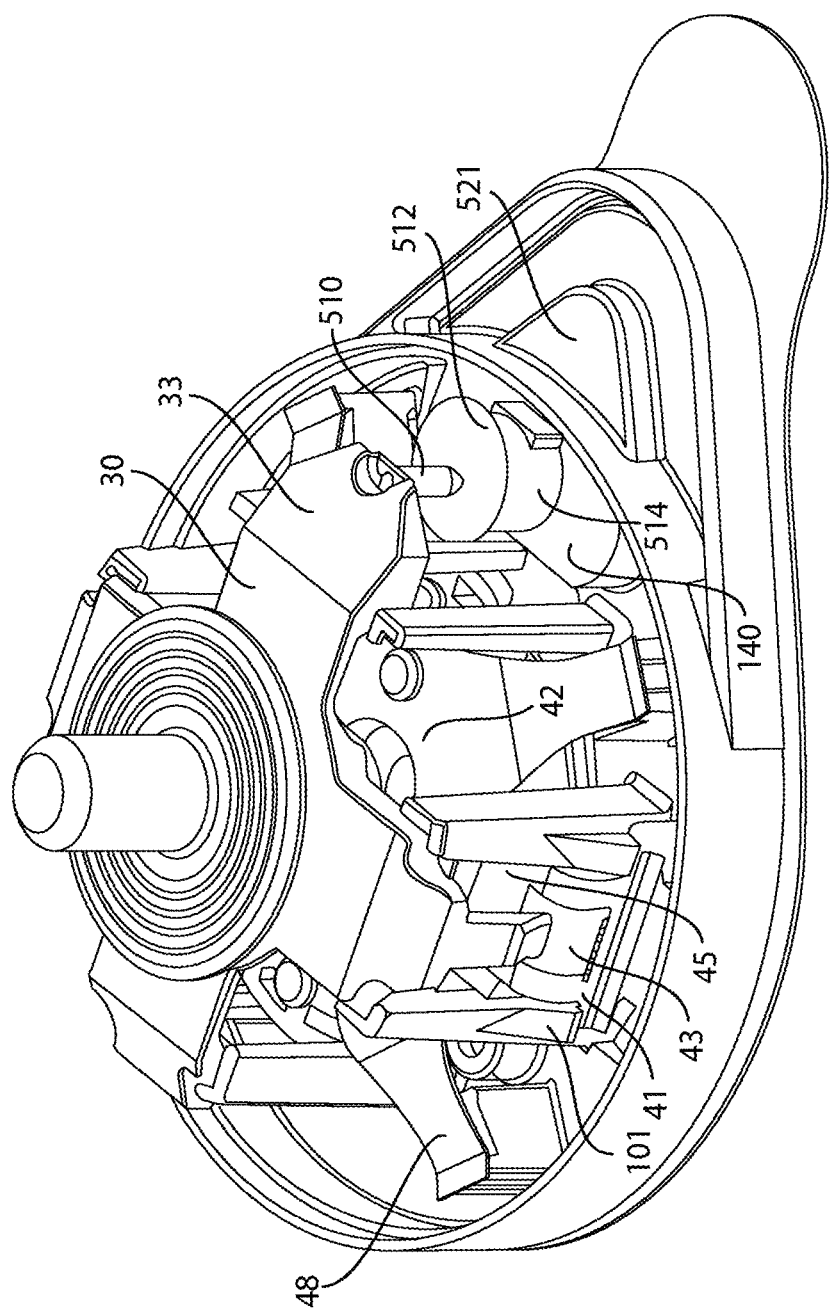
FIG. 28 is a perspective view of the device shown in FIG. 27 with the cover removed.
Figure 29:
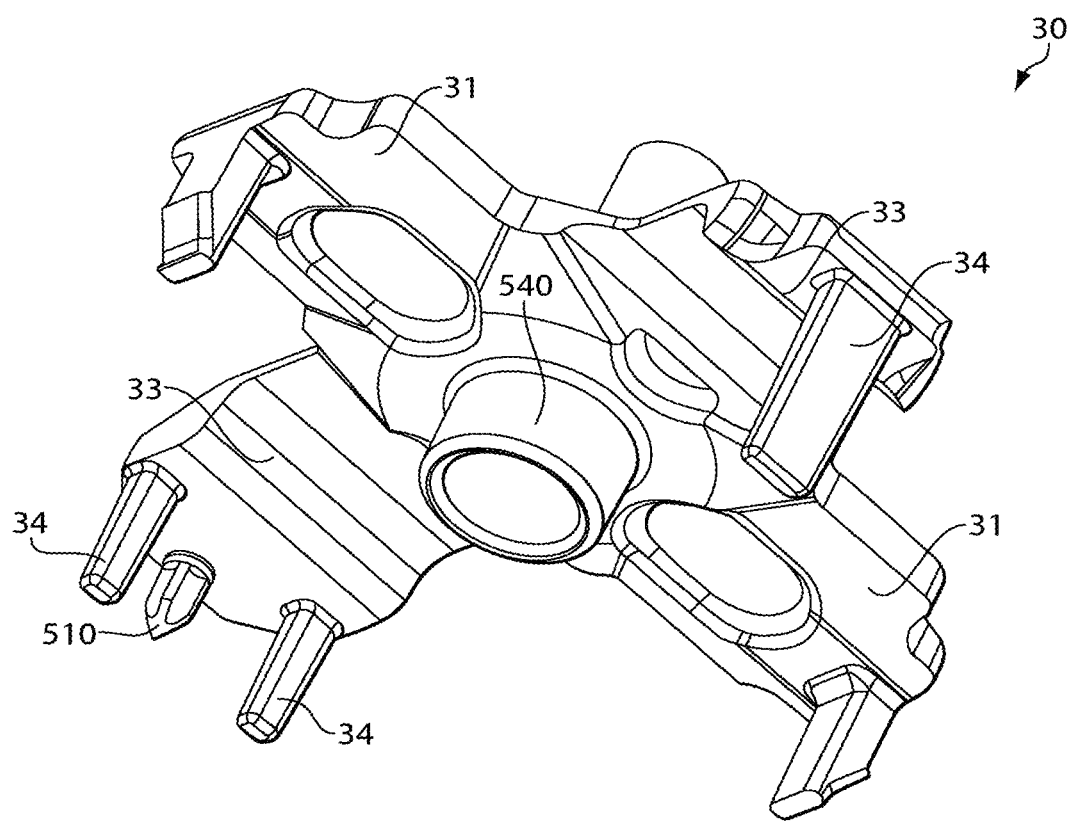
FIG. 29 is an enlarged view of a release element including resistance arms.
Figure 30:
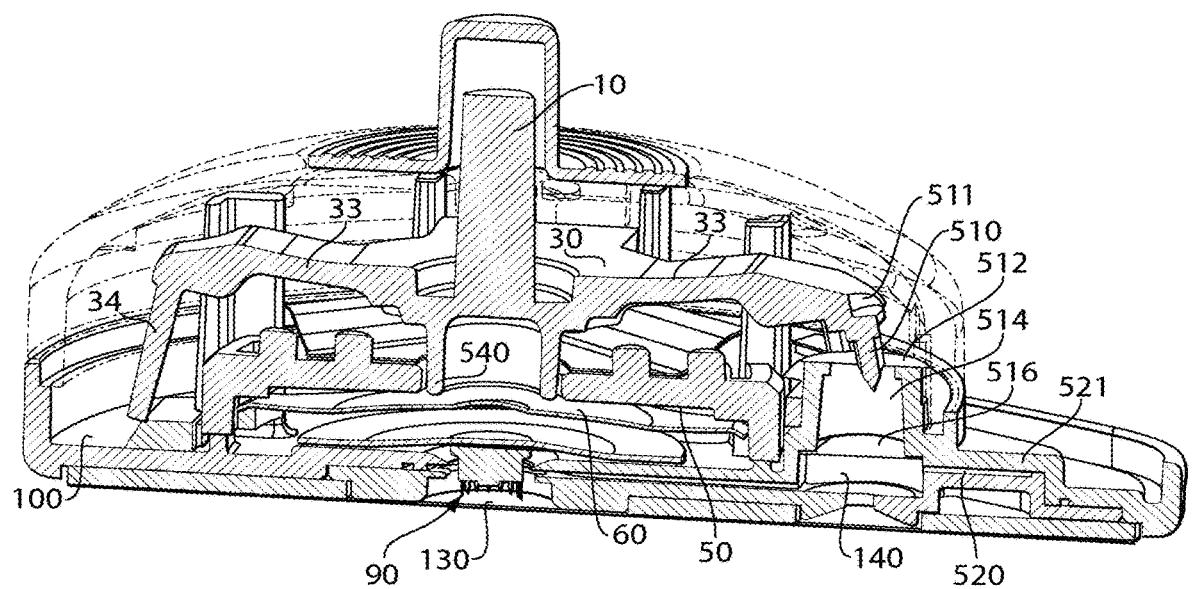
FIG. 30 is another cross-sectional view of a device similar to the one shown in FIG. 27 depicting flexing of the release element.

According to one aspect, the order of operations with regards to deployment and retraction of the flow activator, vacuum release, and the receiving of fluid may be arranged in various sequences. In some embodiments, vacuum release prior to deployment of the flow activator may help to decrease a pressure differential across the deployment actuator and thereby increase insertion depth of the flow activator. For example, in some embodiments, the order of operations may be arranged as follows: vacuum release occurs first, then deployment of the flow activator, and finally, retraction of the flow activator. In some cases, fluid receipt may occur before or after retraction, as this aspect is not limited in this regard. In some cases, fluid receipt may begin before retraction but may not complete until during or after retraction. In some cases, fluid receipt may not begin until during or after retraction. Vacuum release may be accomplished in a variety of different ways, as described in previous embodiments. For example, in one embodiment shown in FIGS. 27-30, a spike 510 is attached to the end of an arm 33 of release element 30. Vacuum may be stored in a vacuum source 156, e.g., a majority of space enclosed by the cover 20, base 100, and membrane 72. Initially, a seal 512 may prevent communication between the vacuum source 156 and the opening 130. Upon downward movement of device actuator 10, spike 510 also moves in a downward direction, pierces seal 512, and enters dead volume 514. Spike 510 may be partially hollow and may include a vacuum inlet channel 511 which may help ensure flow between the vacuum source 156 and the dead volume 514. As a result, puncturing seal 512 with spike 510 effectively opens communication between vacuum source 156 and opening 130. This initial application of vacuum or other relatively low pressure at the area near opening 130 may cause skin to be drawn into or nearer to the opening. Subsequently, further downward movement of device actuator 10 causes actuation ring 540 to contact and actuate deployment actuator 60. As described in previous embodiments, actuation of deployment actuator 60 may cause the flow activator 90 to at least partially extend from the opening 130 or otherwise move to pierce a subject's skin and cause fluid to be released. Fluid may enter the opening 130, and the vacuum released from vacuum source 156 may draw fluid toward and/or into storage chamber 140. A hydrophobic stop membrane 516 that permits passage of air but prevents passage of liquid (such as liquids including water) may be positioned between storage chamber 140 and dead volume 514. As a result, hydrophobic stop membrane 516 may prevent liquid in storage chamber 140 from entering dead volume 514 and vacuum source 156. When storage chamber 140 has been filled with liquid, hydrophobic stop membrane 516 may effectively cooperate with the filled storage chamber 140 to seal off communication between vacuum source 156 and opening 130. After deployment of flow activator 90, effector 50 and retraction actuator (here, composed of locking portion 45 and retractor 42—see FIG. 28) may cooperate to retract flow activator 90 as described in previous embodiments. Similar to the embodiment in FIG. 12 discussed previously, here the retraction actuator may comprise two separated components, locking portion 45 and retractor 42. In this embodiment, however, locking portion 45 differs from the seal actuator portion 44 in FIG. 12 because locking portion 45 does not have an additional seal leg 49 that is used to close communication between vacuum source 156 and opening 130. According to one aspect, in order to permit pressure equilibration across the deployment actuator prior to deployment of the flow activator, a time delay may exist between vacuum release and deployment of the flow activator. In one embodiment, a release element may be arranged to exhibit an increased resistance against downward vertical movement, thereby creating a time delay between vacuum release and deployment of the flow activator. For example, as shown in FIG. 29, release element 30 may include resistance arms 33 in addition to release arms 31. Resistance arms 33 may include legs 34. As shown in FIG. 30, as release element 30 moves in the downward deployment direction, legs 34 may contact base 100 and may cause latch release 30 to flex radially outward, thereby creating lateral movement of spike 510 to facilitate tearing of seal 512 for vacuum release. After vacuum release, contact between legs 34 and base 100 may also provide an increased resistance against downward vertical movement, which may delay deployment of flow activator 90 by delaying contact between actuation ring 540 with deployment actuator 60.

Figure 31:
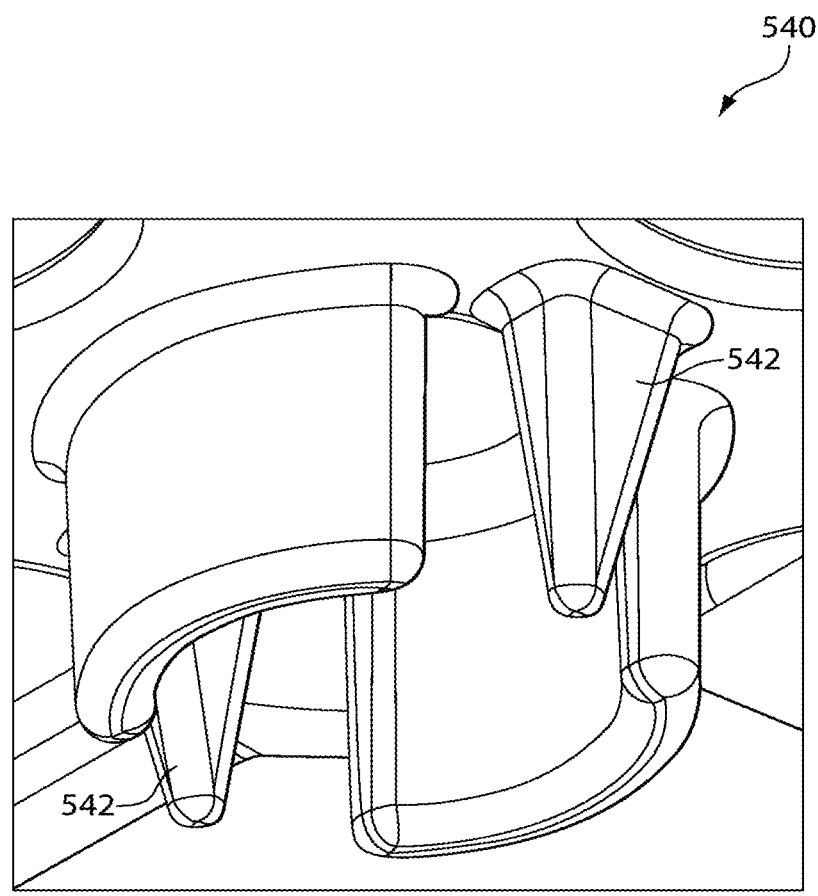
FIG. 31 is an enlarged view of an actuation ring of a release element having tapered legs.
Figure 32A:
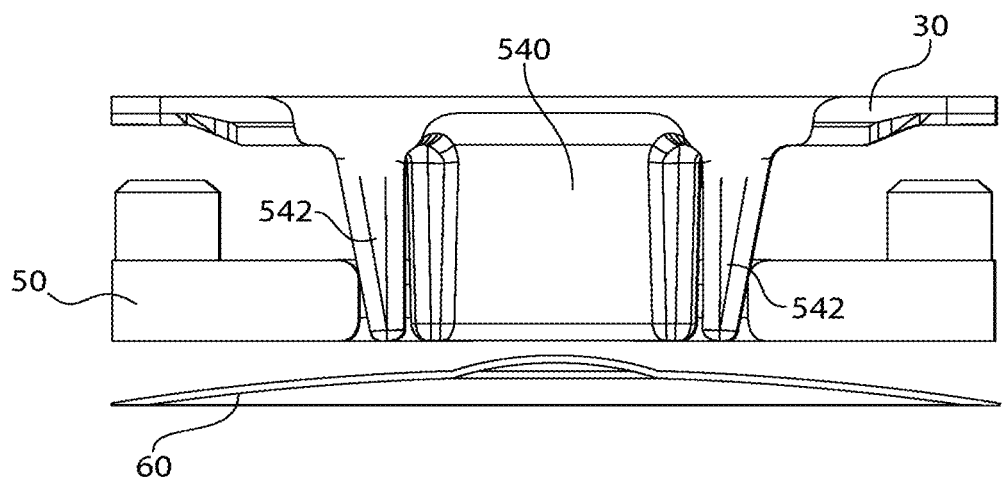
FIG. 32A depicts initial contact between a release element and an effector.
Figure 32B:
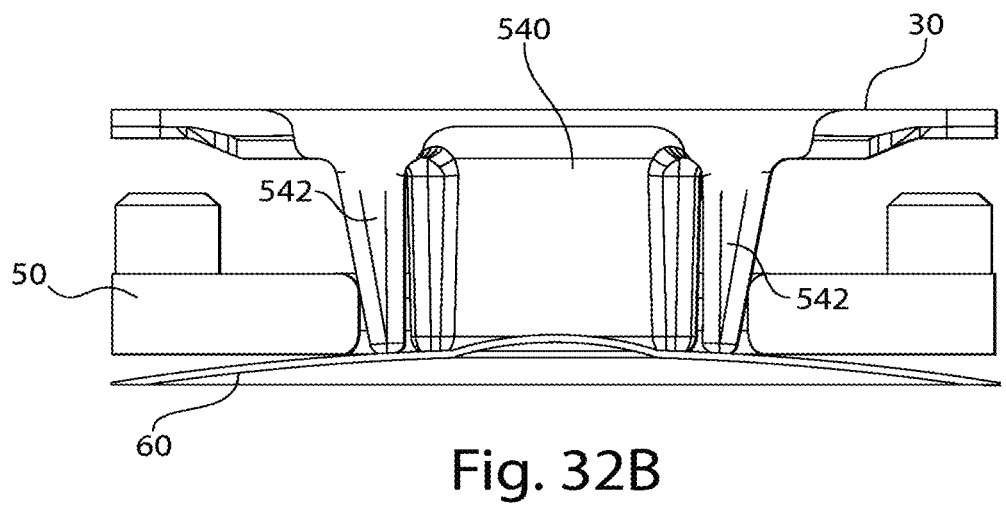
FIG. 32B depicts an interference engagement between an actuation ring of the release element and the effector when the actuation ring has begun to contact a deployment actuator.

According to one aspect, holding the device effector rigidly to the base of the device may help to reduce energy loss when the deployment actuator is actuated. In some cases, stress on the effector or poor fit between components may cause the effector to be positioned incorrectly instead of being held down flush against the base. In certain situations, incorrect positioning of the effector may reduce the translation of energy to the deployment actuator and flow activator during actuation of the device. In one embodiment, an interference fit between the release element and the effector may serve to hold the effector down flush against the base of the device and thereby ensure proper positioning of the effector. In one example, as shown in FIG. 30, the device actuator 10 may be directly attached or otherwise coupled to the release element 30. An actuation ring 540 may be present at the base of the release element 30. The base of the release element 30 may engage the effector 50 by means of an interference fit between the actuation ring 540 and the effector 50. As shown in FIG. 31, actuation ring 540 may include legs 542 that are tapered for increased lateral flexibility. FIG. 32A depicts initial contact between release element 30 and effector 50 prior to flow activator deployment, where the actuation ring 540 has not yet contacted deployment actuator 60. As release element 30 moves further downward, release element 30 becomes engaged in an interference fit with effector 50, as shown in FIG. 32B. FIG. 32B depicts release element 30 and effector 50 just prior to flow activator deployment, where the actuation ring 540 has achieved initial contact with deployment actuator 60. The interference fit permits direct application of pressure to the effector 50 prior to actuation of the deployment actuator 60 in order to ensure that the effector is held flush against the base. Such an arrangement may help ensure correct positioning of the effector and allow energy to translate directly from the device actuator 10 and release element 30 to the deployment actuator 60. Of course, other arrangements are possible, as this aspect is not limited in this regard. For example, the effector may be held flush against the device base by a wave spring or coil spring located beneath the release element, or by a leaf spring, coil spring, foam, an elastic bladder, or other suitable feature molded on the underside of the release element.

Figure 27:
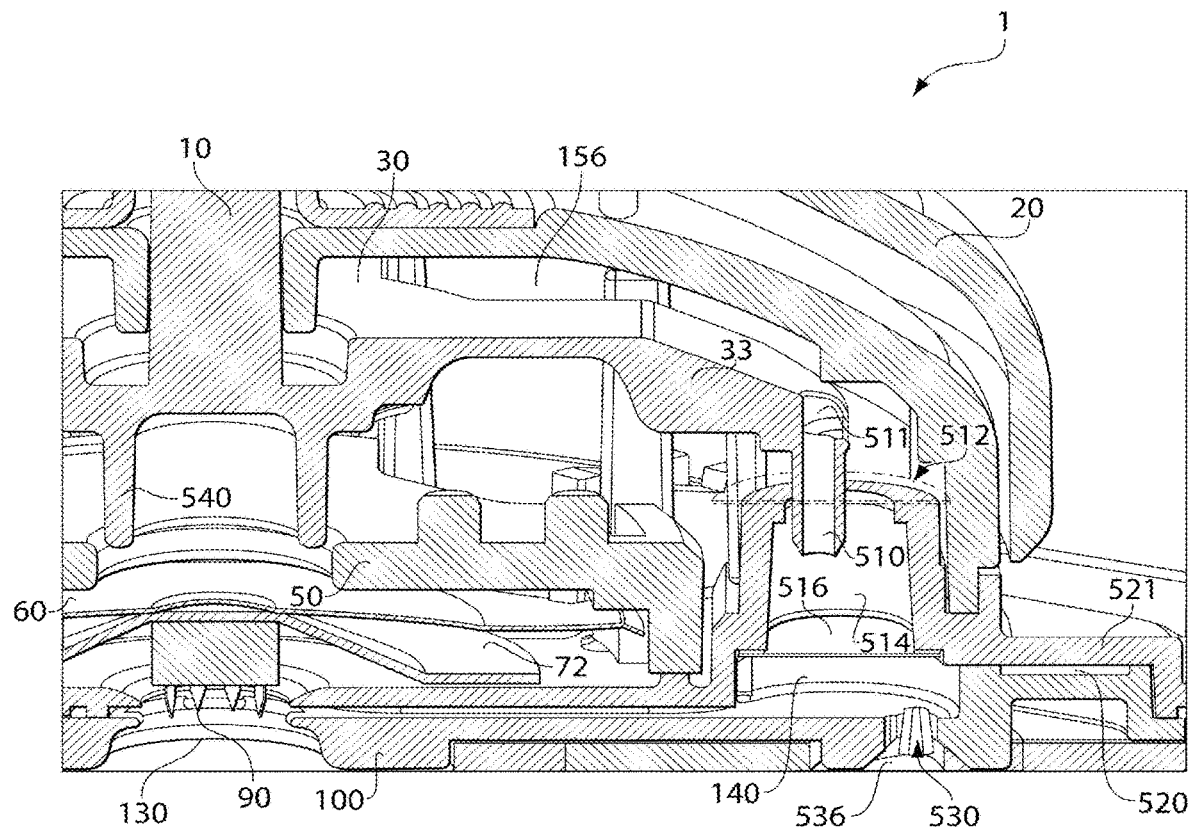
FIG. 27 is a cross-sectional view of a device in yet another embodiment of the invention, having a hollow spike for vacuum release.
Figure 33:
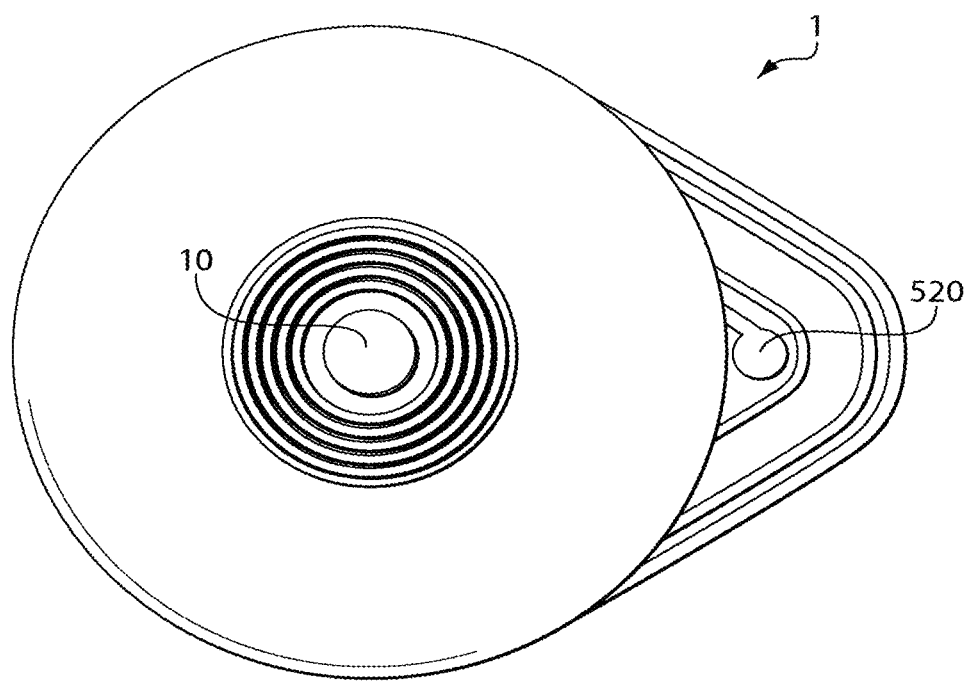
FIG. 33 is an overhead view of a device having an indicator.
Figure 34:
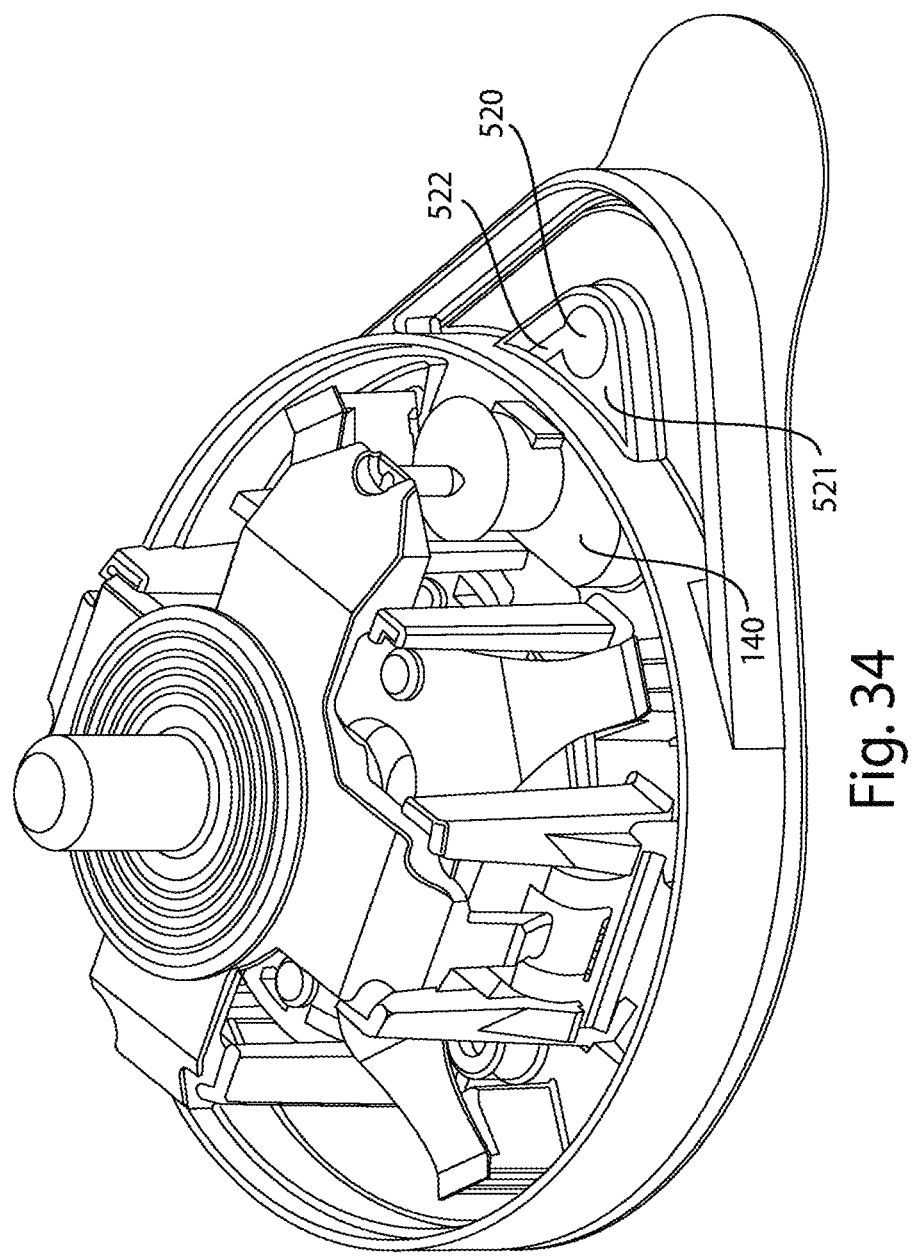
FIG. 34 is a perspective view of the device shown in FIG. 33 with the cover removed.

According to one aspect, the device may enable an indication when the receiving of fluid is complete. Such indication may notify a user that the device can be removed from the skin. In one embodiment, shown in FIGS. 27, 33, and 34, a visual indication may be provided by an indicator 520. Indicator 520 may change color when the receiving of fluid is complete. In one example, indicator 520 may change from clear to the color of the received fluid. As shown in FIGS. 27 and 34, indicator 520 may include a flat disc of space that can receive and hold fluid. Indicator 520 may be in open communication with storage chamber 140. During the receiving of fluid, when fluid reaches the top of storage chamber 140, fluid may enter a passage 522 that connects storage chamber 140 to indicator 520. Fluid may enter and travel through passage 522 into indicator 520 due to capillary action, wicking, pressure differential, or via any other suitable force. In some instances, indicator 520 may include a solid or liquid substance that changes color upon contact with the received fluid. In this way, a user may receive an indication that the receiving of fluid is complete without actual sight of the received fluid. For example, indicator 520 may turn a color that is different than the actual collected fluid. In some embodiments, the device may include an indicator cover 521 that may be transparent or translucent to allow a user to view indicator 520. In some embodiments, indicator cover 521 may be tinted a color to change the appearance of the color of the fluid. In some cases, indicator cover 521 may be removable. Of course, it should be appreciated that the indication may be visual, audible, or tactile, as this aspect is not limited in this regard. For example, filling of storage chamber 140 may trigger the device to emit an audible sound indicating that the receiving of fluid is complete. In some instances, the audible sound may be a mechanical click due to interaction between the device actuator, release element, effector, retraction actuator, deployment actuator, and/or flow activator. In some instances, the audible sound may be an alarm that is triggered due to fluid reaching the top of storage chamber 140. Alternatively or in addition, the user may receive tactile feedback indicating that the receiving of fluid is complete. For example, the device actuator, release element, effector, retraction actuator, deployment actuator, and/or flow activator may be arranged to interact such that the user actuating device actuator experiences a sudden increase or decrease in physical resistance from the device actuator. As another example, the components of the device may include a detent-type interaction that provides tactile feedback to the user. Furthermore, the indications, feedback, and/or alarms may occur at any point in the device actuation process, as indications are not limited to the completion of the receiving of fluid. For example, the device may enable an indication when vacuum has been released, when the flow activator has been deployed and/or retracted, when the receiving of fluid has begun, etc. The device may also enable an indication or alarm when an insufficient volume fluid has been received, or if the type of fluid received is inappropriate.

Figure 35:
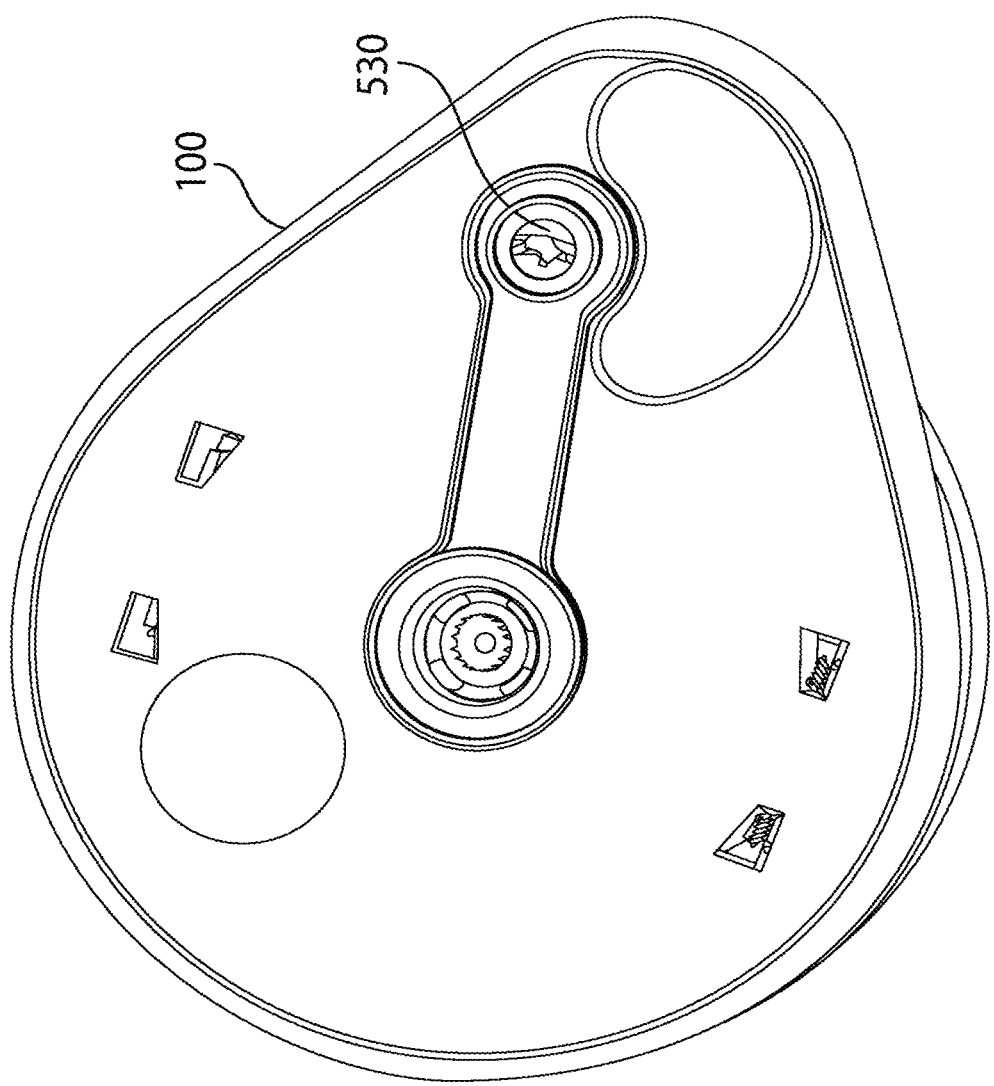
FIG. 35 is a perspective view of the underside of a device in yet another embodiment of the invention, having an access port.
Figure 36A:
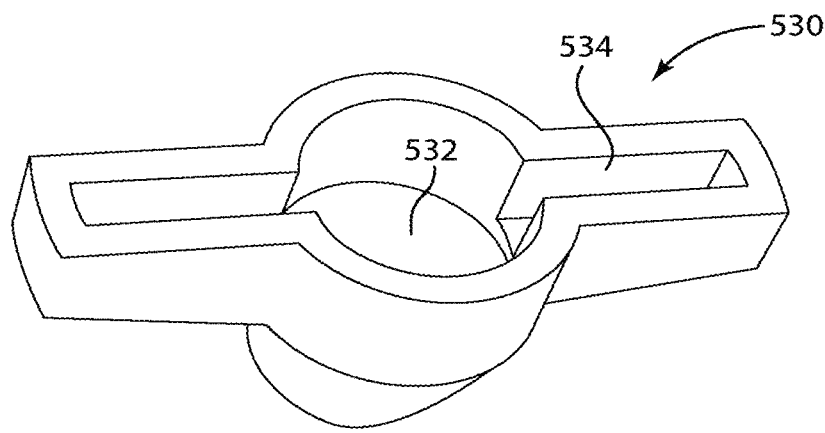
FIG. 36A is an enlarged view of an access port similar to the one shown in FIG. 35.
Figure 36B:
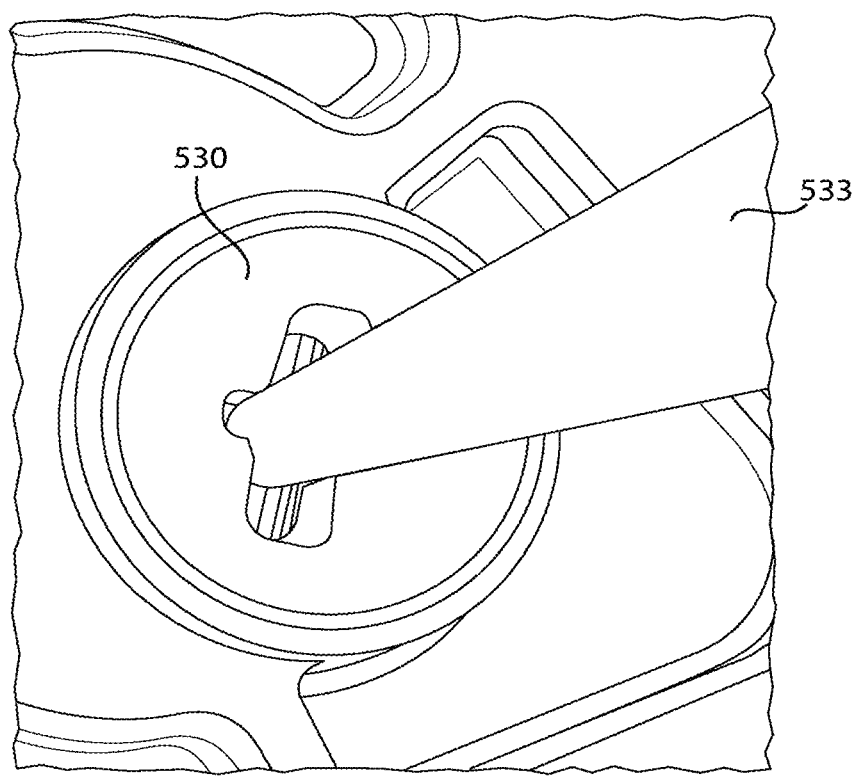
FIG. 36B is an enlarged view of a pipette interacting with an access port similar to the one shown in FIG. 35.
Figure 37:
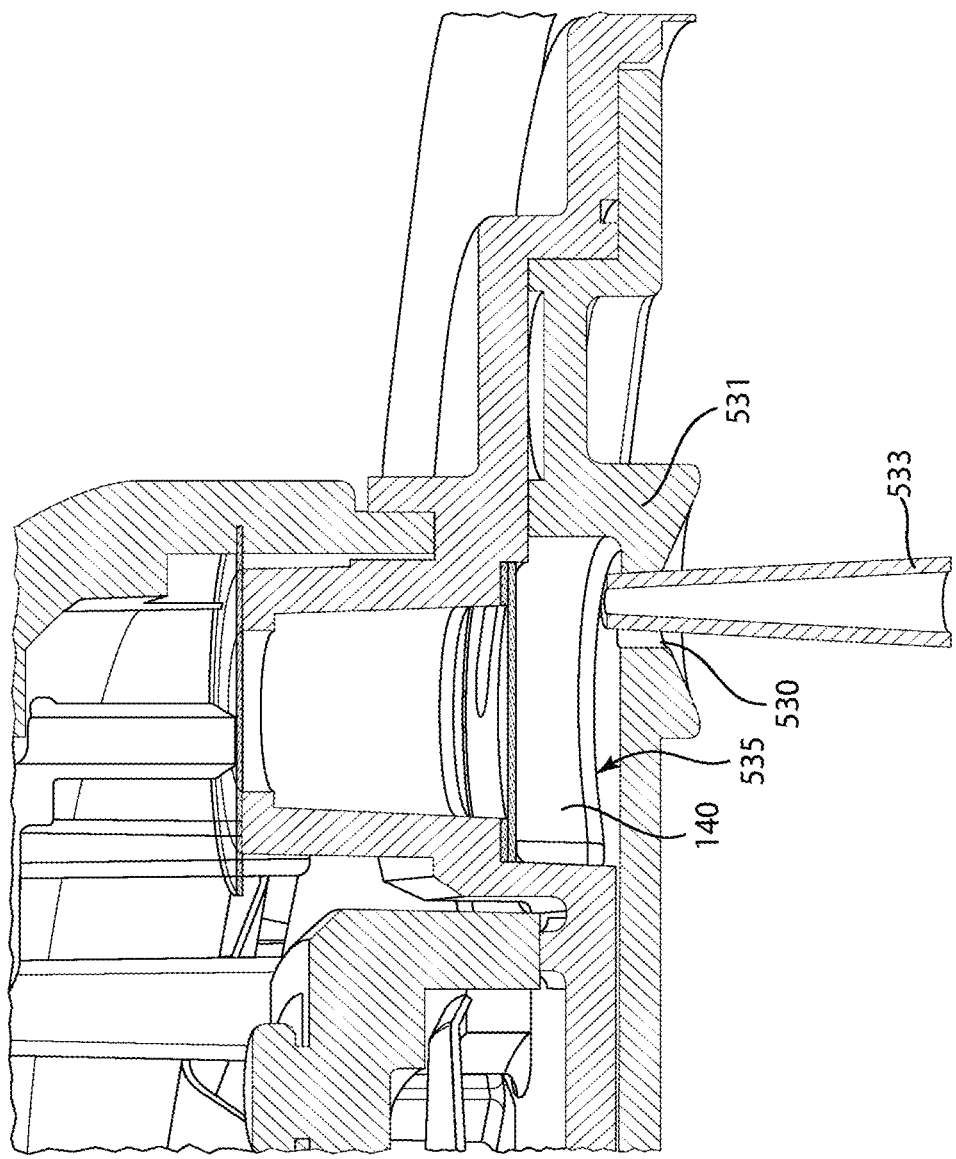
FIG. 37 is an enlarged view of a pipette interacting with an access port and a storage chamber.
Figure 38:
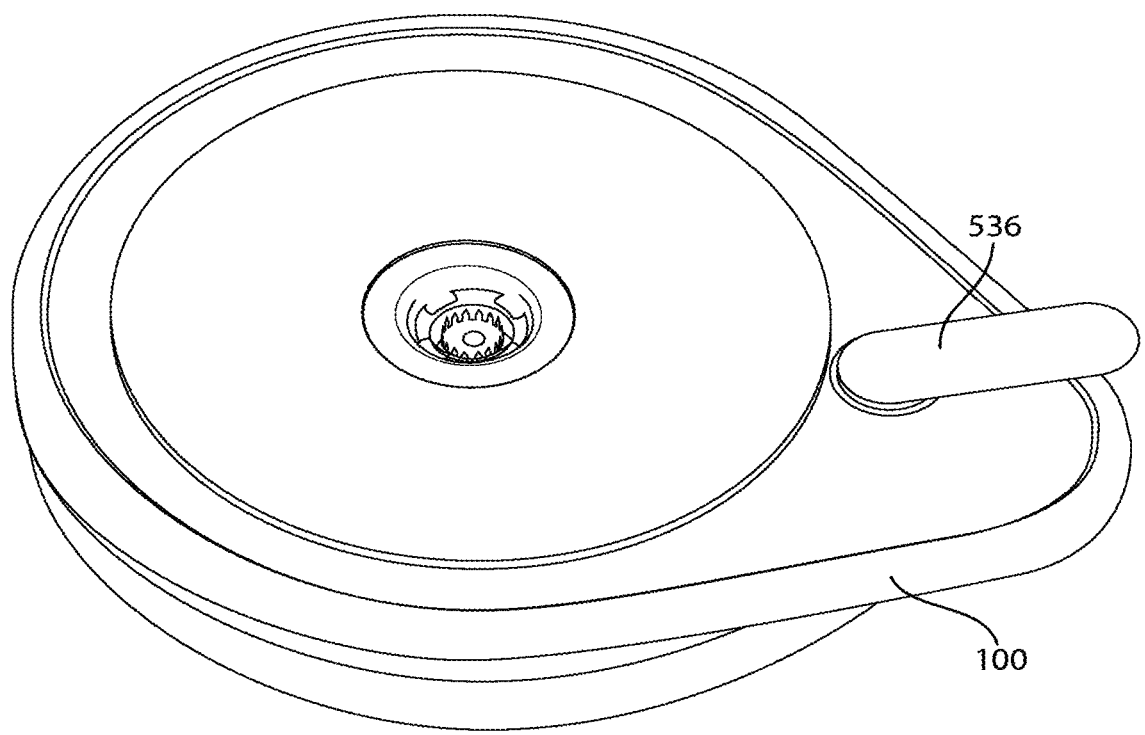
FIG. 38 is an underside view of a device with a seal covering an access port.
Figure 39:
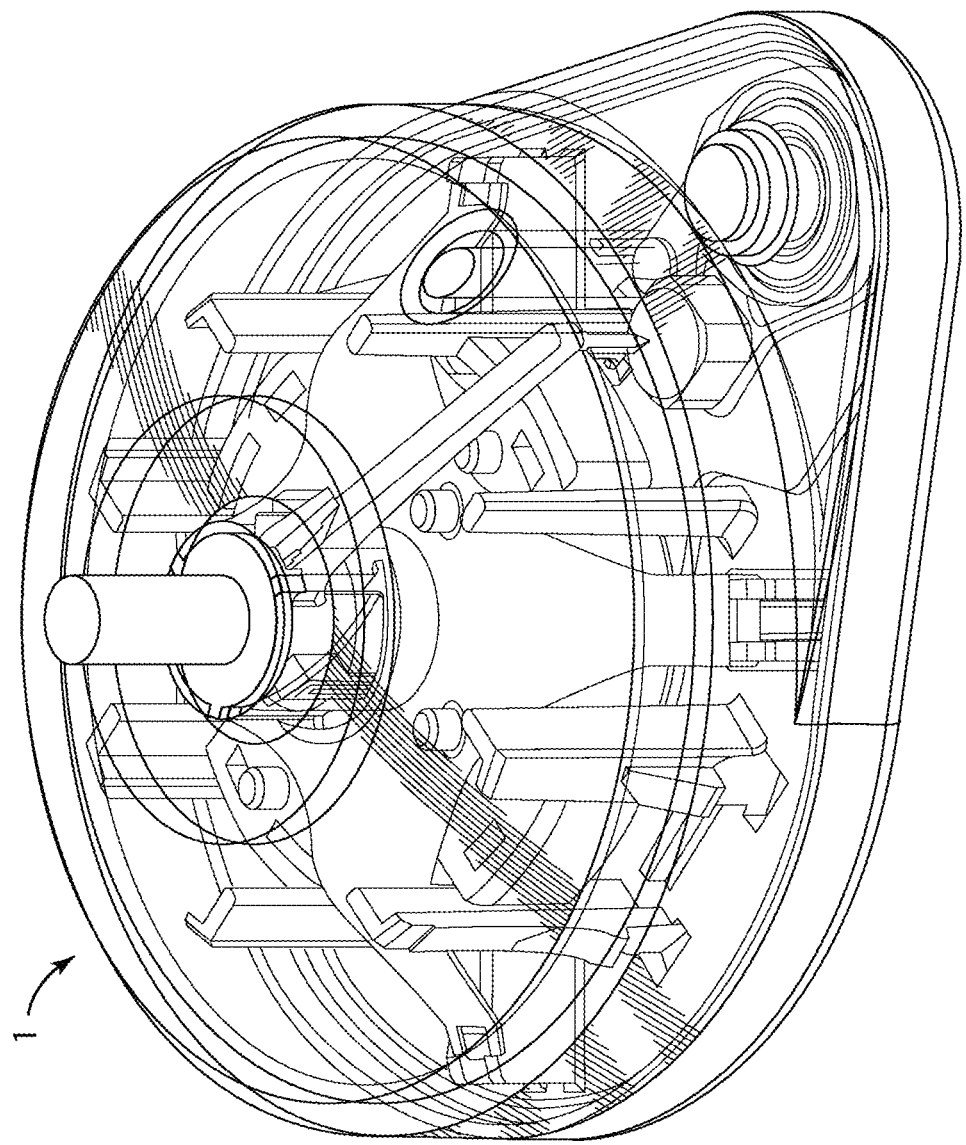
FIG. 39 is a perspective view of a device in yet another embodiment of the invention, having a rotatable release element that interacts with the device cover.

According to one aspect, the device may allow a user to access fluid that is received in the storage chamber of the device. In some embodiments, an access port connected to the storage chamber may allow the user to directly access fluid in the storage chamber. In one embodiment, as shown in FIG. 35, an access port 530 may be located at the base of the device. Of course, it should be appreciated that the access port 530 may be located at any location of the device, as this aspect is not limited in this regard. In some embodiments, a user may remove the fluid using a variety of tools such as a pipette, capillary tube, or other suitable tool. In some embodiments, a user may access the fluid in the storage chamber without removal of the fluid from the chamber. For example, a user may measure the pH of the fluid by contacting a strip of pH paper with the fluid. In another example, a user may require access to the collected fluid in order to add a substance or chemical to the fluid while it is held in the storage chamber. In some embodiments, access port 530 may be shaped to permit insertion of objects of different shapes, such as strips as well as pipettes or capillary tubes. In one example, shown in FIGS. 36A-B, access port 530 may include a hole 532 to receive cylindrical objects such as pipettes and capillary tubes, and may include a slot 534 to receive rectangular or wide objects such as strips. Of course, other shapes and geometries of the access port are possible, such as a simple hole, slot, square hole, or multiple holes, as this aspect is not limited in this regard. In some embodiments, the access port may be positioned to increase ease of fluid removal from the storage chamber. In one example, shown in FIG. 37, access port 530 may be positioned near the side wall 531 of storage chamber 140. Positioning access port 530 away from the center of storage chamber 140 may help to decrease forces such as capillary action that may cause the fluid to resist removal from the storage chamber. Alternatively or in addition, the bottom of storage chamber may be arranged at a slant such that fluid is slanted downward toward the access port. Storage chamber 140 may further include a circular groove that runs around the bottom periphery 535 of the storage chamber where the bottom of the storage chamber meets side wall 531. Such a groove may urge fluid toward access port 530 via wicking, capillary action, or other suitable force. In some embodiments, a seal may prevent fluid from flowing through the access port. In one example, the seal may be located inside the storage chamber, in which case a user punctures the seal with a pipette or other suitable tool. In another example, as shown in FIG. 38, the seal 536 may be located outside the storage chamber on the base 100, in which case a user may peel off or puncture the seal to access the fluid in the storage chamber. Of course, it should be appreciated that other methods of sealing the access port are possible, as this aspect is not limited in this regard.

Figure 40A:
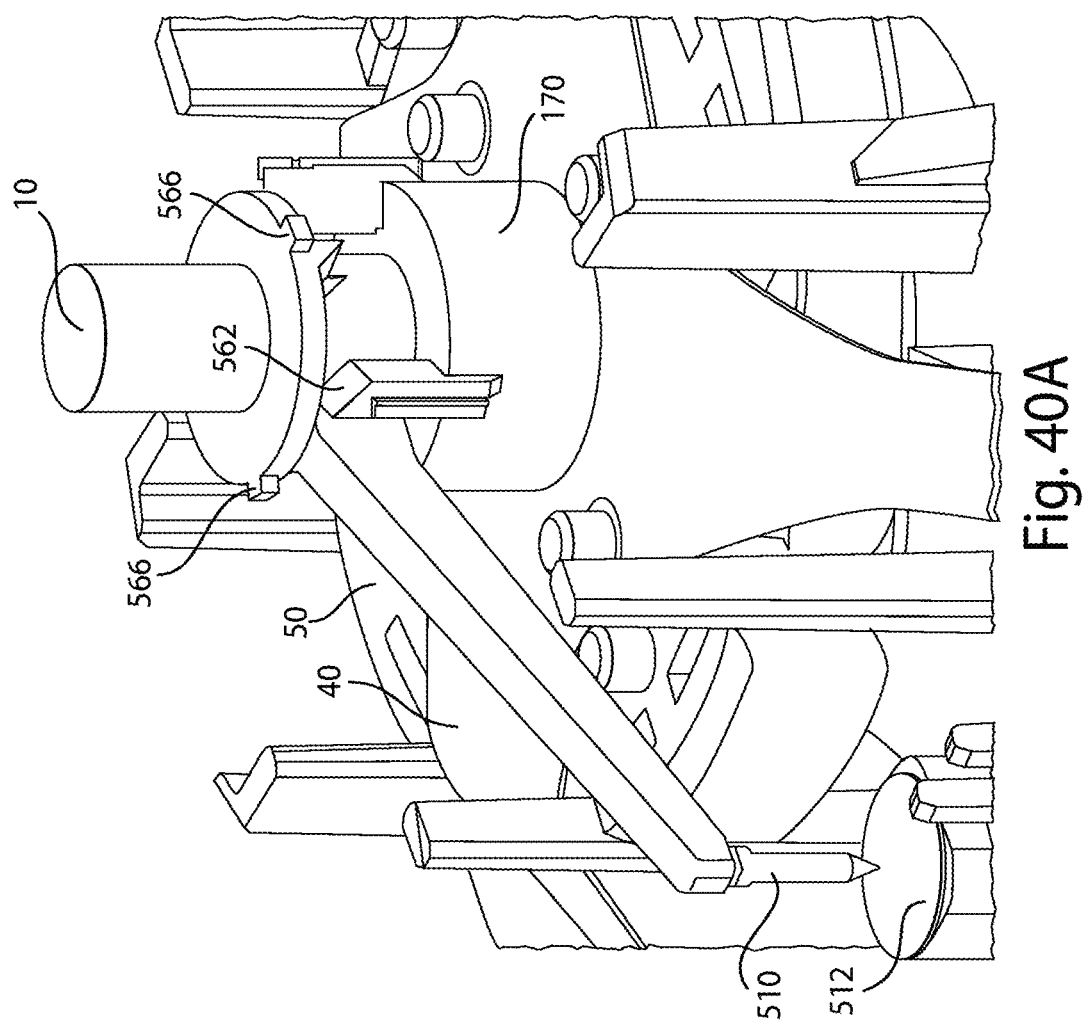
FIG. 40A is a close-up view of the device shown in FIG. 39 with the cover removed.
Figure 40B:
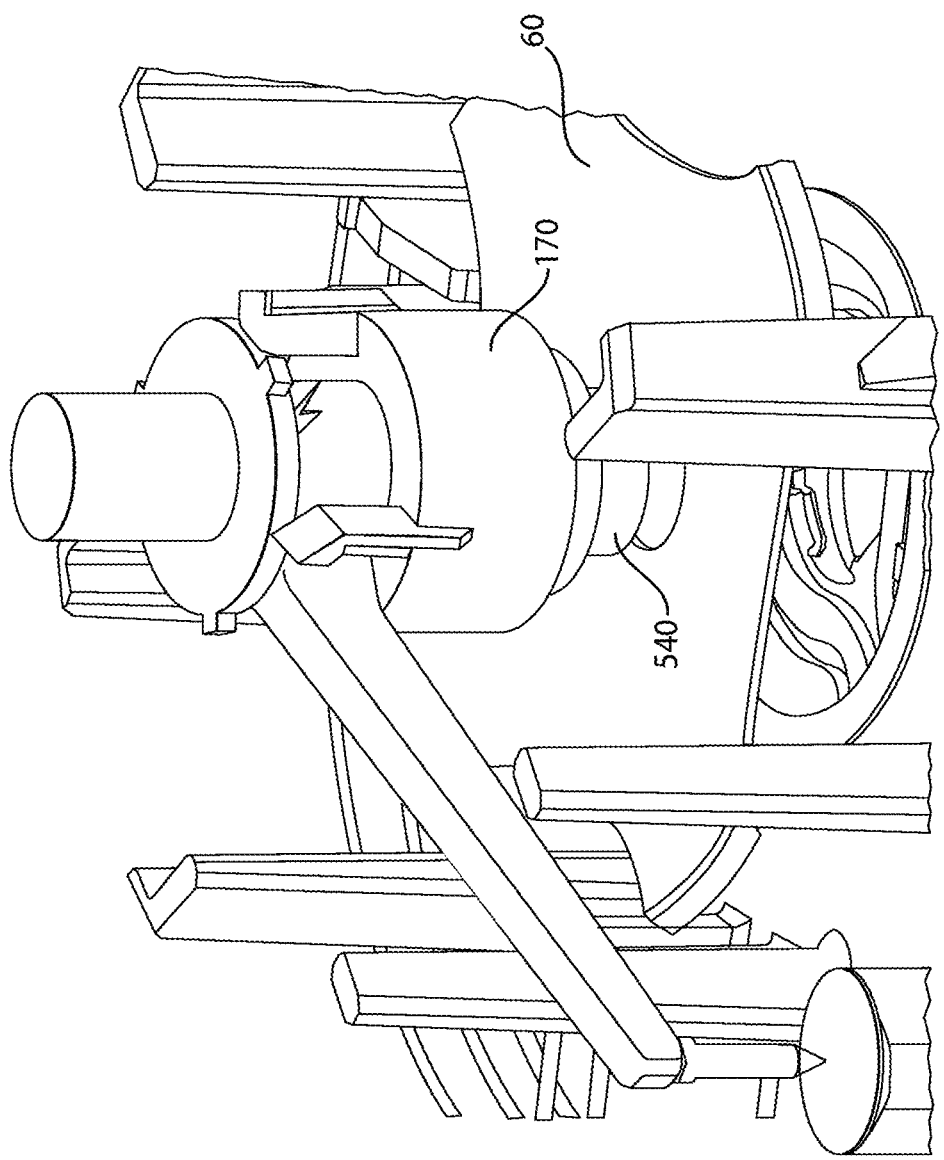
FIG. 40B is the close-up view shown in FIG. 40A with the retraction actuator and effector hidden from view.
Figure 41:
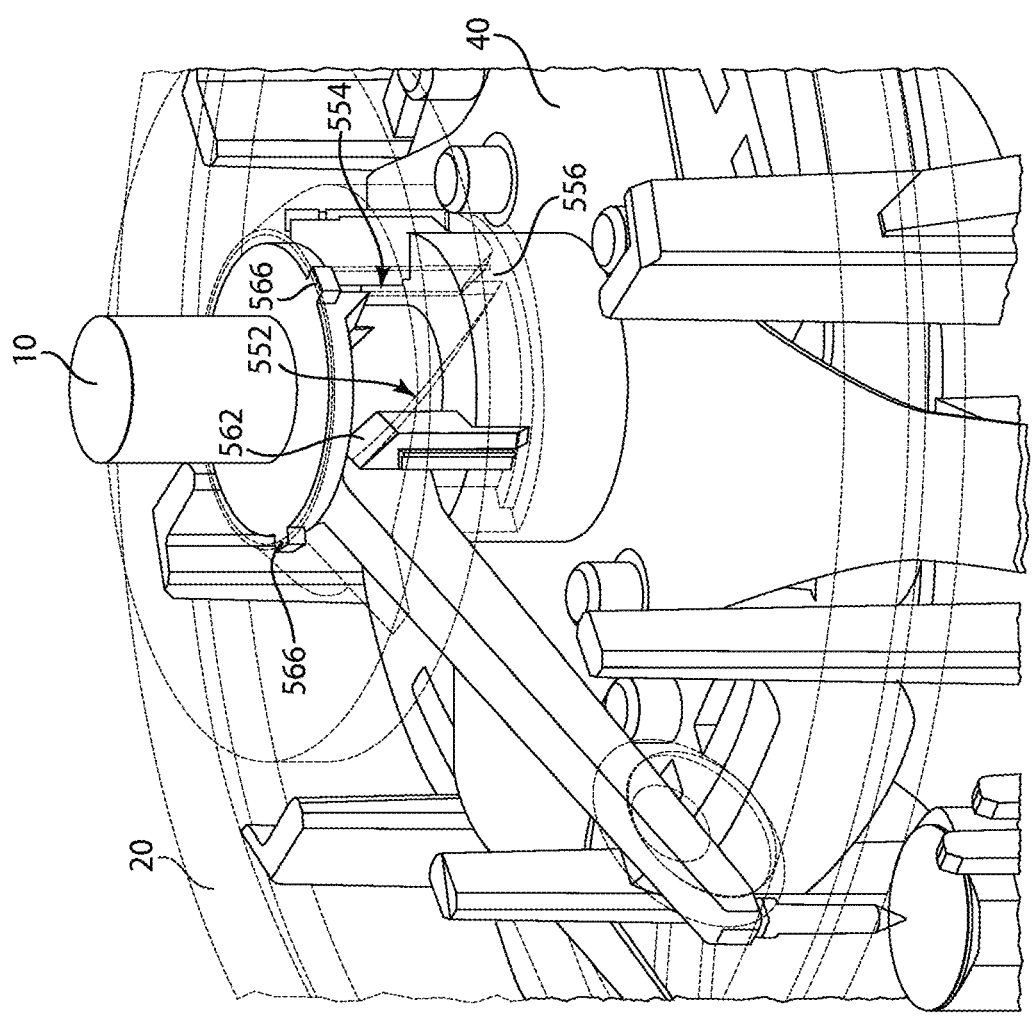
FIG. 41 is the close-up view shown in FIG. 40A with the device cover shown in phantom.
Figure 42:
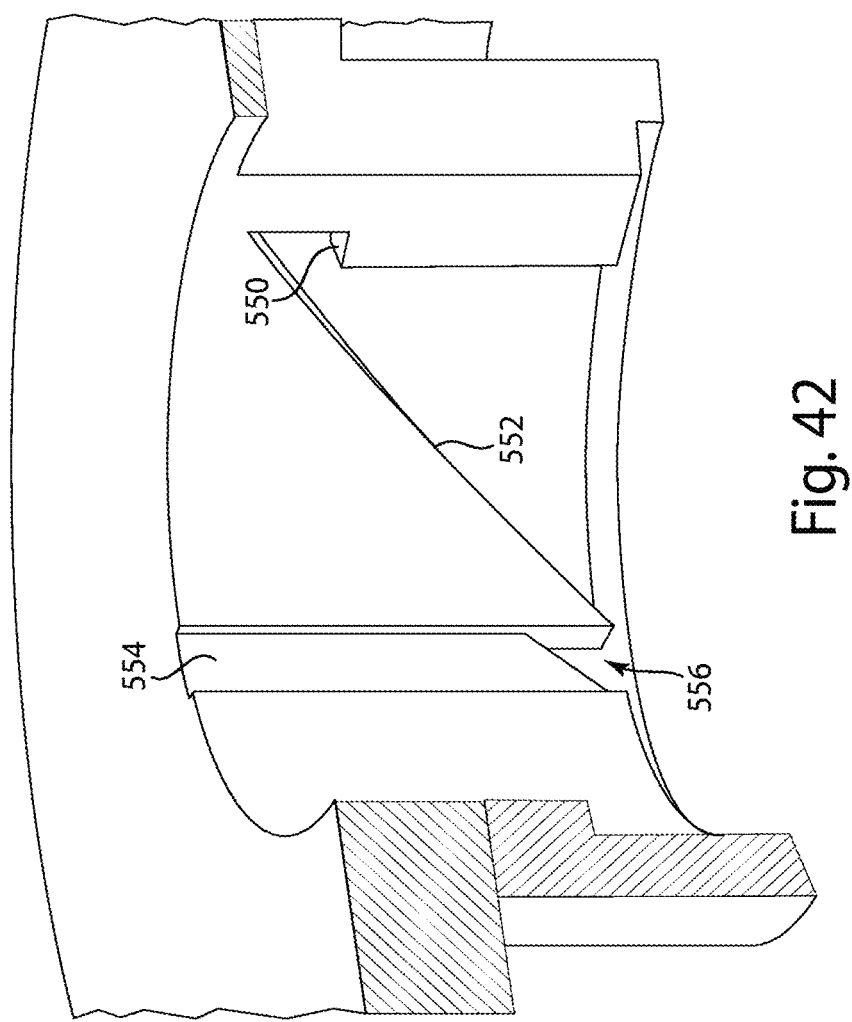
FIG. 42 is an enlarged view of a portion of the device cover from the device shown in FIG. 39.
Figure 43:
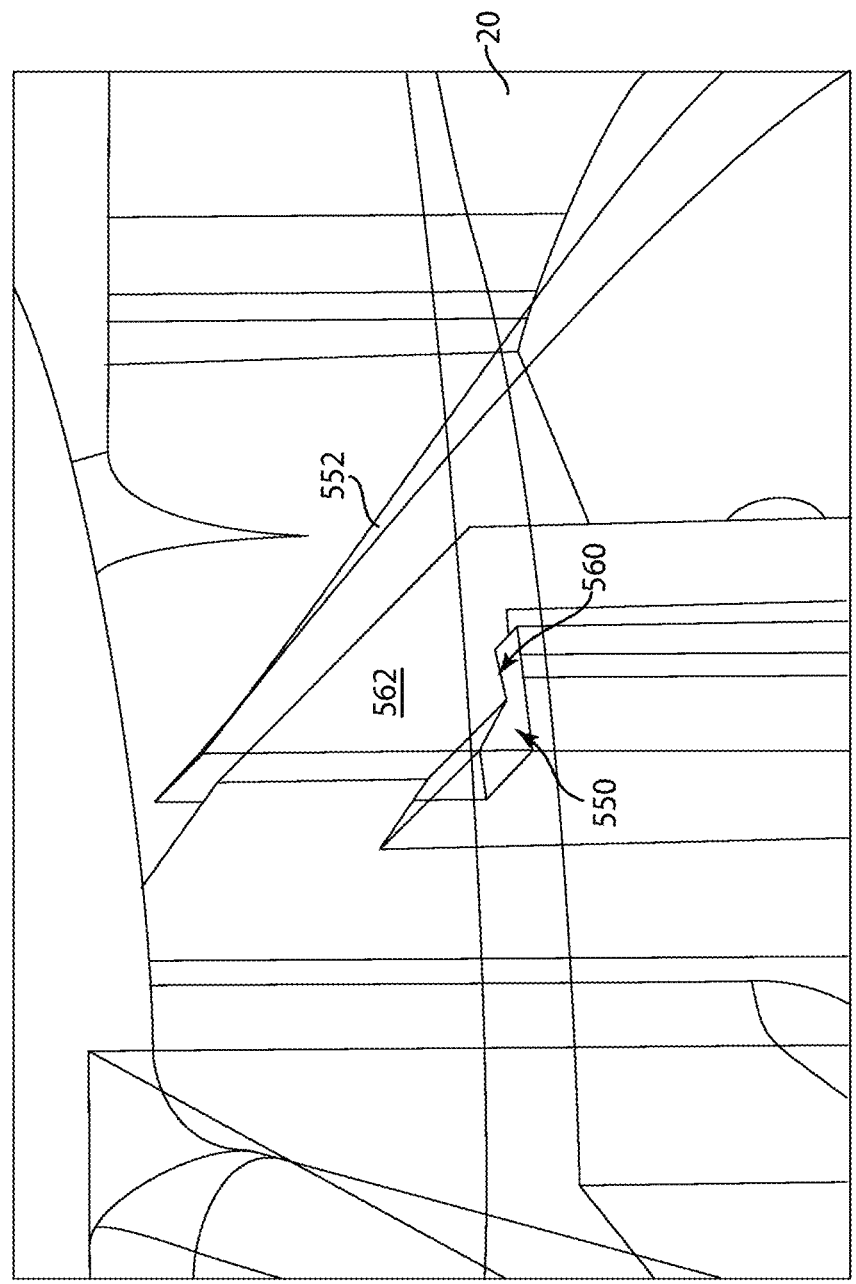
FIG. 43 is a close-up view of a spinner ramp of the device shown in FIG. 39 interacting with the device cover, where the device cover is shown in phantom.

In one alternative embodiment, a rotatable release element may be arranged to permit vacuum release prior to flow activator deployment. FIGS. 39-43 show one example of a device with a rotatable release element. In these figures, the device is depicted its post-deployment, retracted state. The device includes rotatable release element 170 that is free to rotate relative to device actuator 10 (see FIGS. 40A-B). Device actuator 10 is attached to spike 510 such that downward movement of device actuator 10 causes downward movement of spike 510, which then pierces seal 512 for vacuum release. As discussed previously, piercing seal 512 opens communication between the vacuum source and the device opening, allowing vacuum to be applied at the device opening. Device actuator 10 also includes tabs 566 that interact with a slide groove 554 formed on the device cover 20 (see FIGS. 41 and 42) to constrain movement of device actuator 10 to the vertical direction. The rotatable release element 170 includes a spinner ramp 562 that interacts with a pre-deployment lockout 556 and a cover ramp 552 (see FIGS. 41 and 42) formed on the cover 20. As shown in FIG. 40B, the retraction actuator 40 and effector 50 are hidden from view to show that rotatable release element 170 also includes an actuation ring 540 that actuates deployment actuator 60 upon contact with the top surface of the deployment actuator 60. (In FIG. 40B, deployment actuator 60 is shown in its post-deployment state and is therefore arranged concave downward away from actuation ring 540.) Prior to deployment, spinner ramp 562 is held within pre-deployment lockout 556 such that actuation ring 540 on the release element 170 is held at a distance close to the top surface of the deployment actuator 60. Engagement between spinner ramp 562 and pre-deployment lockout 556 also locks retraction actuator 40 in a compressed, high-energy state. Depression of device actuator 10 in the downward direction may first cause spike 510 to pierce seal 512 for vacuum release, then cause actuation ring 540 on the release element 170 to contact and actuate deployment actuator 60, thereby deploying the flow activator, as discussed in previous embodiments. At the same time, depression of actuator 10 in the downward direction also causes spinner ramp 562 to clear pre-deployment lockout 556, releasing retraction actuator 40 from its compressed, high energy-state. Retraction actuator 40 releases its stored potential energy as it decompresses by moving in the upward retraction direction, causing spinner ramp 562 to slide against cover ramp 552 in the upward direction. As a result, the entire rotatable element 170 rotates clockwise as it also moves upward in the retraction direction. Upward movement of the retraction actuator 40 causes the flow activator to retract, as described in previous embodiments. Finally, as shown in FIG. 43, when spinner ramp 562 reaches the end of the cover ramp 552, engagement edge 560 of the spinner ramp 562 engages with post-deployment lockout 550 to lock the device in the retracted state.

According to one aspect, actuation of the flow activator may occur in direct response to vacuum release without requiring additional external actuation. In one embodiment, a pressure differential across the deployment actuator may cause the deployment actuator to deploy the flow activator. In previously discussed embodiments, such as in the FIGS. 1-5 embodiment, vacuum may be stored in a vacuum source 156, e.g., a majority of space enclosed between the device cover 20, base 100, and membrane seal 72. According to the present aspect, however, in one example, atmospheric or ambient pressure is stored in the space enclosed by the cover, base, and membrane seal rather than a vacuum source. The vacuum source is stored in another location either within the device or external to the device rather than above the deployment actuator. As a result, prior to actuation of the device, the pressure at the top surface of the deployment actuator is at atmospheric or ambient pressure instead of at vacuum pressure. Opening communication between the vacuum source and the device opening may expose the bottom surface of the deployment actuator to vacuum pressure, thereby creating a pressure differential across the deployment actuator: atmospheric or ambient pressure above the deployment actuator and vacuum pressure below. The pressure differential across the deployment actuator may actuate the deployment actuator and subsequently cause deployment of the flow activator. Such an arrangement may allow vacuum to reach the device opening prior to deployment of the flow activator.

Figure 44:
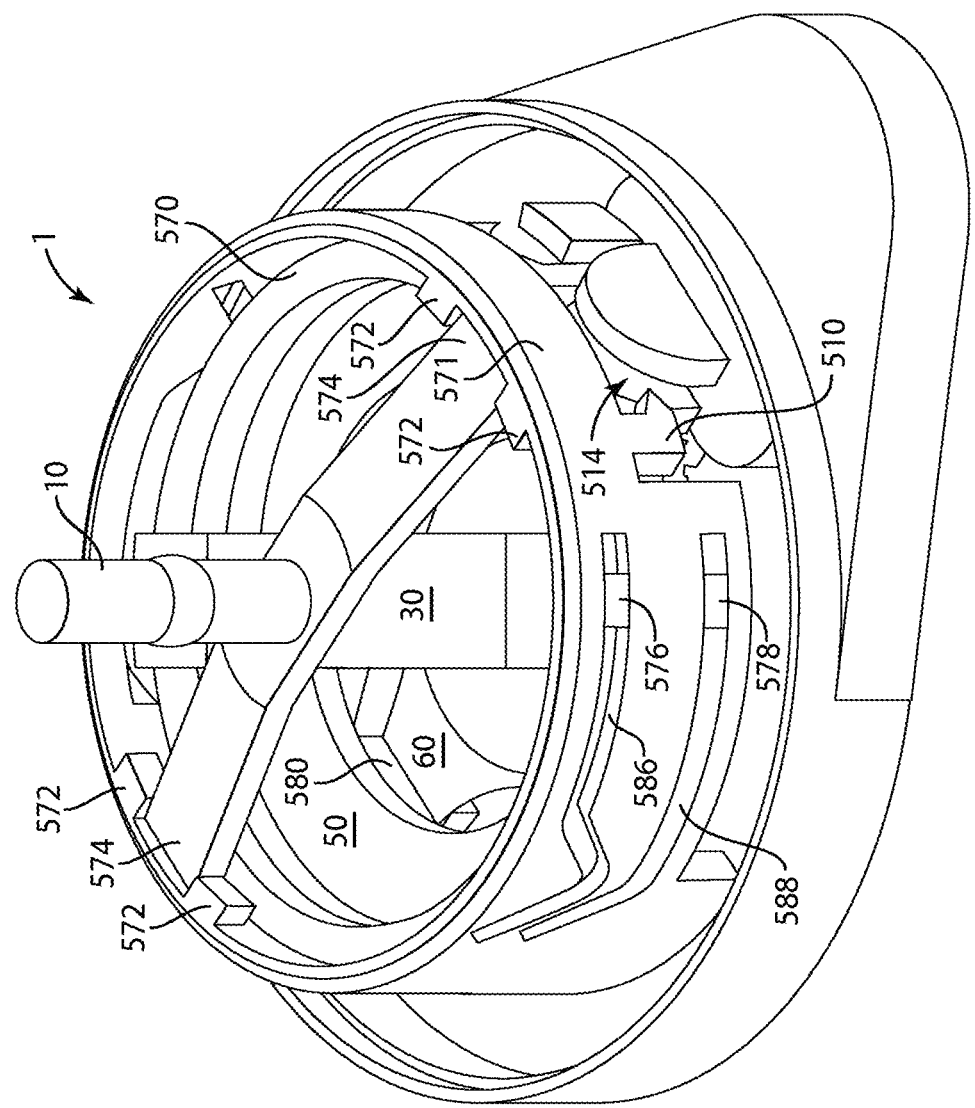
FIG. 44 is a perspective view of a device with the cover removed in yet another embodiment of the invention, having a release element and a torsion spring.
Figure 45:
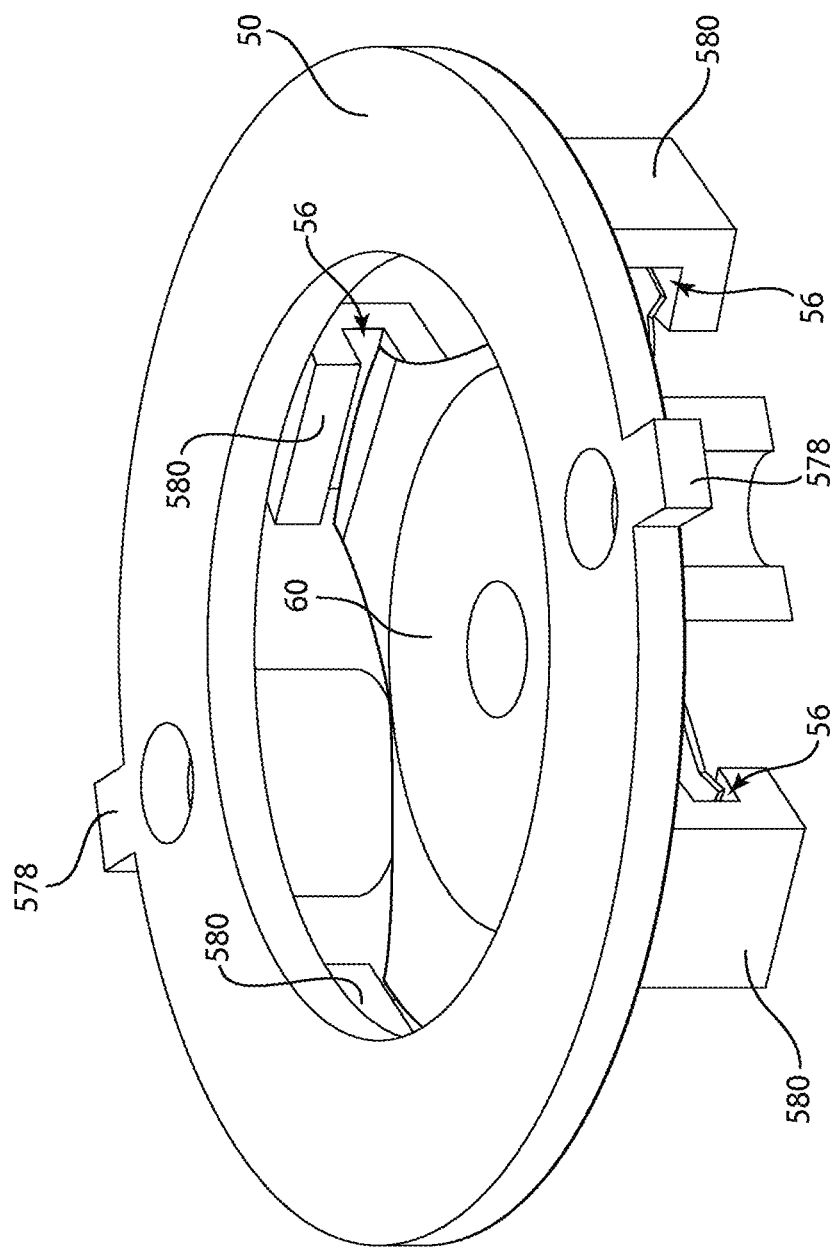
FIG. 45 is an enlarged view of the effector and deployment actuator from the device shown in FIG. 44.
Figure 46A:
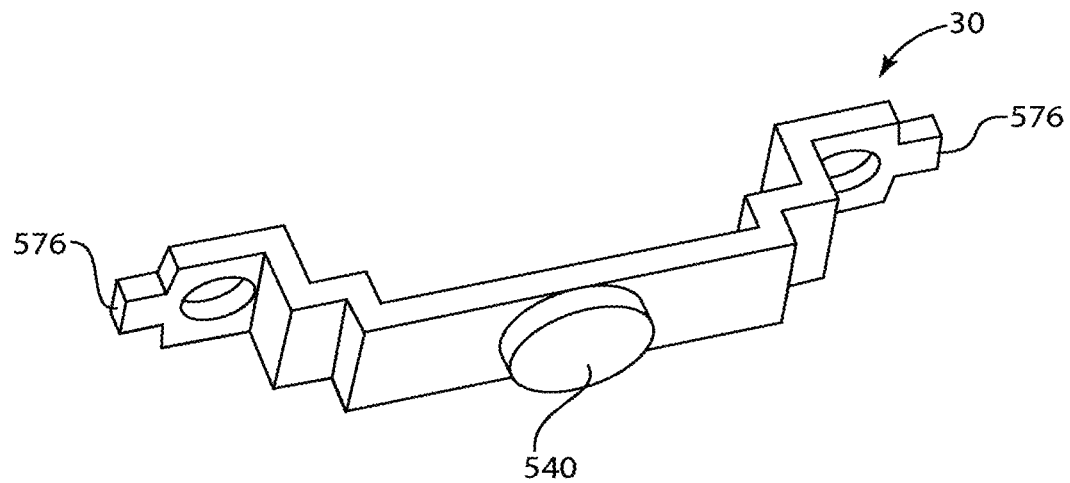
FIG. 46A is a bottom perspective view of the release element from the device shown in FIG. 44.
Figure 46B:
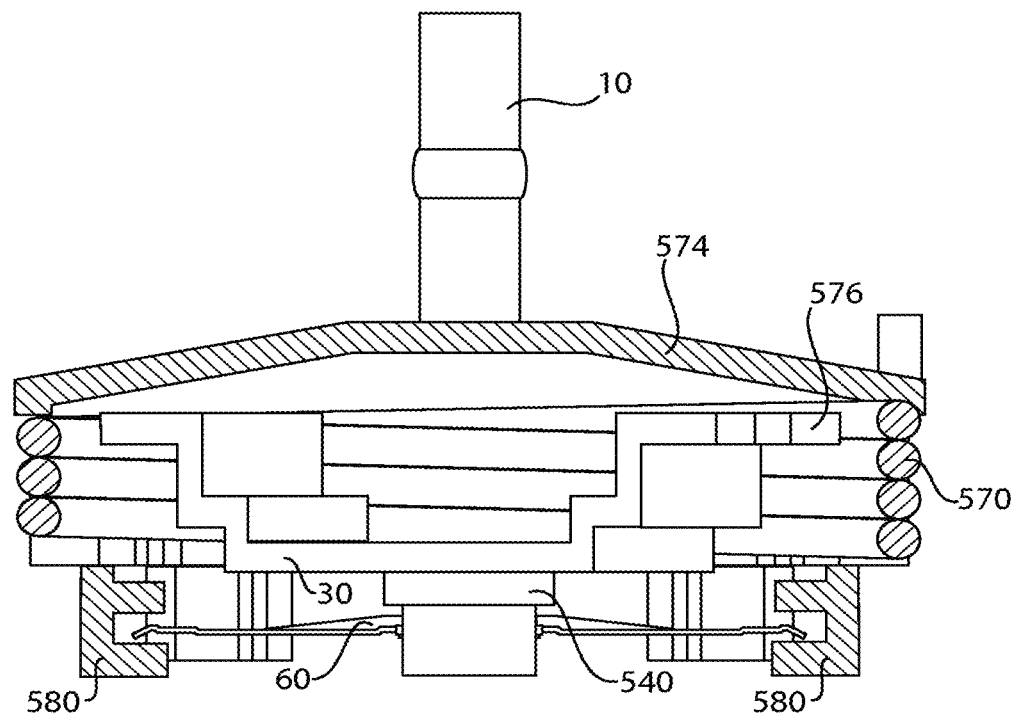
FIG. 46B is a side view of the device shown in FIG. 44 with the base hidden and the torsion spring and effector shown in phantom.

According to one aspect, the sequence of events starting from the initial actuation of the device to the end of receipt of fluid may be user-independent, meaning that, after an initial trigger, the entire sequence of events occurs automatically regardless of the subsequent magnitude of pressure, torque, speed, impact, or other force applied to the device actuator after the trigger. In one embodiment, the device may include a torsion spring that permits a user-independent sequence of actuation events. For example, as shown in FIG. 44, device 1 includes a torsion spring 570 that may serve as a retraction actuator. In FIG. 44, device 1 is depicted in its pre-deployed, high-energy state, with a coiled torsion spring 570 attached to cam 571. Potential energy may be stored in coiled torsion spring 570, and the spring may be attached to cam 571 such that the spring is biased to rotate cam 571 in the counterclockwise direction. Engagement between the ends of the actuator arm 574 and lockout protrusions 572 attached to cam 571 prevent rotation of cam 571 and thereby prevent the uncoiling of torsion spring 570. Device actuator 10 may be actuated by a downward force, causing the ends of actuator arm 574 to slide vertically downward relative to lock-out protrusions 572. Once the ends of actuator arm 574 slide below and clear the lower surface of lock-out protrusions 572, cam 571 is free to rotate, allowing torsion spring 570 to uncoil and release its stored potential energy. Release of torsion spring 570 may serve as the trigger from which all subsequent user-independent events follow. Uncoiling of torsion spring 570 causes cam 571 to rotate in the counterclockwise direction. Cam 571 may be attached to a spike 510 that tears through a seal (not shown) covering dead volume 514, opening communication between a vacuum source and the opening of the device. As shown in FIG. 45, effector 50 may be attached to deployment actuator 60 via holders 580 and grooves 56. In addition, the effector 50 may include effector tabs 578. As shown in FIGS. 46A-B, release element 30 may include an actuation ring 540 and release element tabs 576. As shown in FIG. 44, effector tab 578 may cooperate with a lower track 588. During rotation of cam 571 in the counterclockwise direction, tab 578 interacts with the profile of lower track 588. As the lower track 588 slants upward at the end of its profile, tab 578 is pushed upward by lower track 588. As a result, effector 50 is raised in the vertically upward retraction direction. Similarly, the release element tab 576 of release element 30 cooperates with an upper track 586. During counterclockwise rotation of cam 571, tab 576 interacts with the profile of upper track 586. As the profile of upper track 586 dips downward, tab 576 is pushed downward by upper track 586. As a result, release element 30 is lowered vertically downward in the deployment direction, causing the actuation ring 540 of release element 30 to contact and actuate deployment actuator 60 (see FIGS. 46A-B), thereby actuating a flow activator (not shown) in a manner described in previous embodiments. As track 586 slants upward at the end of the profile, release element 30 is raised in the vertically upward retraction direction. After actuation of the deployment actuator 60, both the release element 30 and the effector 50 are lifted in the retraction direction due to the upward slanting of both upper track 586 and lower track 588, thereby causing retraction of the flow activator (not shown), which is connected to the deployment actuator 60 and effector 50. Of course, it should be appreciated that other suitable arrangements for achieving a user-independent sequence of events are possible, as this aspect is not limited in this regard.

Figure 47:
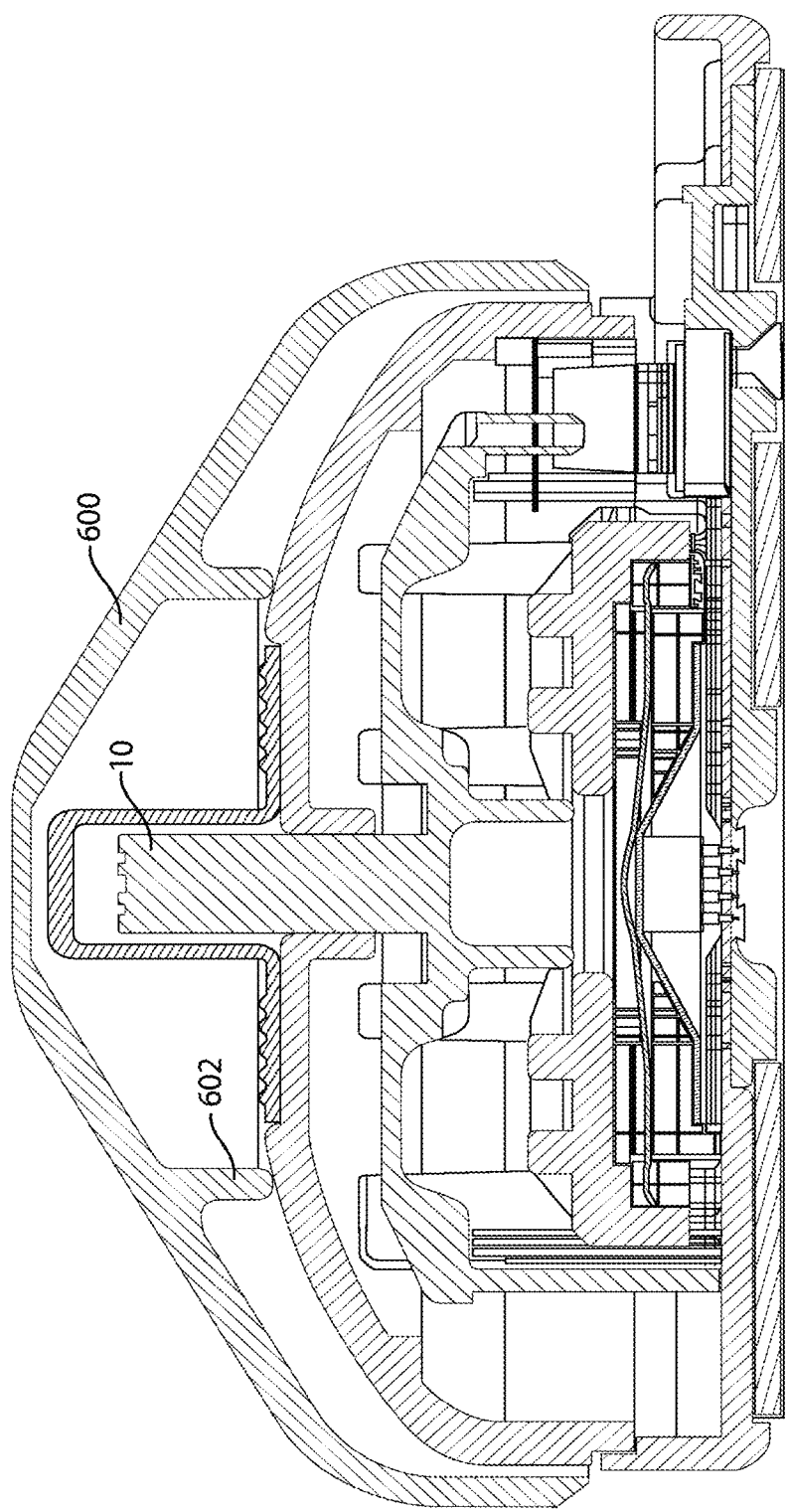
FIG. 47 is a cross-sectional view of a device in yet another embodiment of the invention, having a protective cap.

According to one aspect, the device may include a protective feature or mechanism used to avoid inadvertent or pre-mature actuation. In one embodiment, the protective feature may include a physical barrier or covering that prevents actuation of the device actuator. For example, as shown in FIG. 47, the device may include a cap 600 with a spacer ring 602 that prevents compression of device actuator 10. Cap 600 may be removed by a user when the device is ready to be actuated. In one embodiment, the protective feature may be incorporated into the device actuator or other components of the device. For example, the device actuator may include a lost-motion type arrangement in which the device actuator must travel a pre-defined distance before deployment of the deployment actuator is triggered. In another example, the device actuator may require application of a minimum pressure or torque before actuation occurs. In yet another example, device actuator may include a safety-lock type arrangement in which the user must first twist the device actuator before pushing it down. Of course, it should be appreciated that other methods of avoiding inadvertent actuation are possible, as this aspect is not limited in this regard. In addition, the above-mentioned safety features can be combined in any manner within a single device.

Figure 48A:
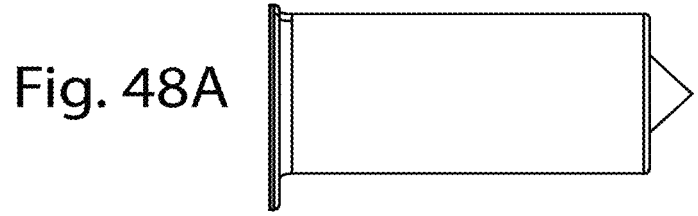
FIGS. 48A-G are enlarged views of various spike geometries.
Figure 48B:
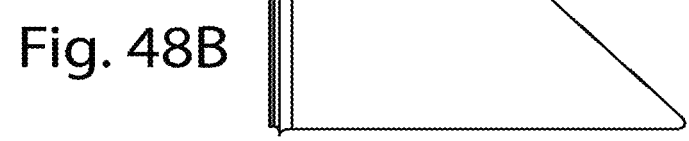
Figure 48C:
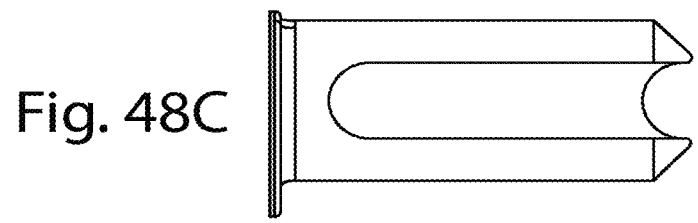
Figure 48D:
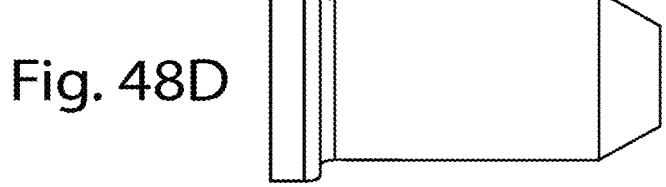
Figure 48E:
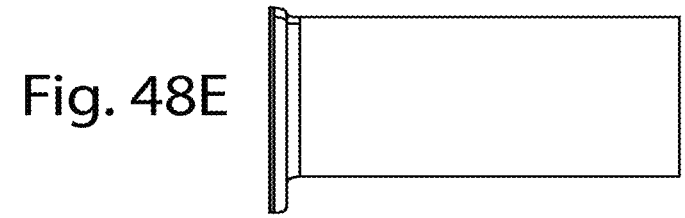
Figure 48F:
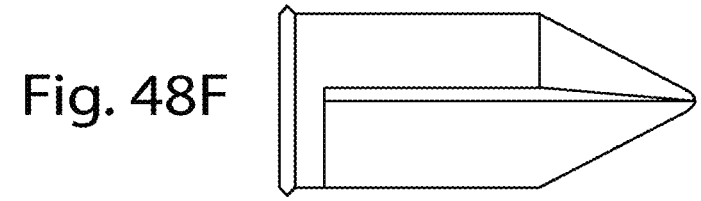
Figure 48G:
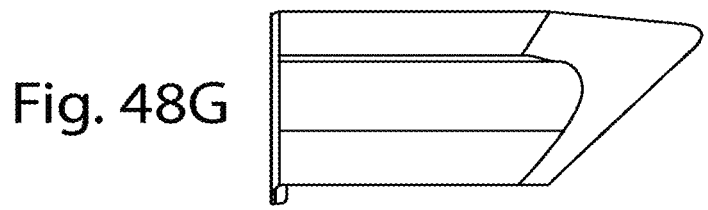

Some of the previously described embodiments include a spike used to pierce a seal in order to open communication between a vacuum source and the device opening. According to one aspect, a wide variety of spike geometries are possible. For example, FIGS. 48A-G depict various possible spike geometries, such as a cylinder with a pointer at the end (FIG. 48A), a cylinder with a slanted end (FIG. 48B), a bifurcated arrangement (FIG. 48C), a hollow cylinder with beveled tip (FIG. 48D), a simple cylinder that may be solid or hollow (FIG. 48E), a pointed spike with an indented portion (FIG. 48F), and a V-shaped spike with a longitudinal groove (FIG. 48G). Of course, it should be appreciated that any geometry suitable for seal piercing or tearing may be used for the spike geometry, as this aspect is not limited in this regard. Further details regarding optional arrangements for needles, which may be included as part of a flow activator, are provided below.

As mentioned above, needles included with a flow activator may be arranged in a variety of different ways, depending on the intended application. For example, the needle(s) may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. The needle(s) may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. For example, in one embodiment, the needle(s) may have a rectangular cross section having dimensions of 175 micrometers by 50 micrometers. In one set of embodiments, the needle(s) may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc.

In one embodiment, the needle(s) is(are) a microneedle (s). Typically, a microneedle will have an average cross-sectional dimension (e.g., diameter) of less than about a millimeter. It should be understood that references to "needle" or "microneedle" as discussed herein are by way of example and ease of presentation only, and that in other embodiments, more than one needle and/or microneedle may be present in any of the descriptions herein. As an example, microneedles such as those disclosed in U.S. Pat. No. 6,334,856, issued Jan. 1, 2002, entitled "Microneedle Devices and Methods of Manufacture and Use Thereof," by Allen, et al., may be used to deliver to and/or withdraw fluids (or other materials) from a subject. The microneedles may be hollow or solid, and may be formed from any suitable material, e.g., metals, ceramics, semiconductors, organics, polymers, and/or composites. Examples include, but are not limited to, medical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters. In some cases, more than one needle or microneedle may be used. For example, arrays of needles or microneedles may be used, and the needles or microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of needles or microneedles. Typically, a microneedle will have an average cross-sectional dimension (e.g., diameter) of less than about a micron.

Those of ordinary skill in the art can arrange needles relative to the skin or other surface for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin or other surface at approximately 90°.

In some cases, the needles (or microneedles) may be present in an array selected such that the density of needles within the array is between about 0.5 needles/mm$^2$ and about 10 needles/mm$^2$, and in some cases, the density may be between about 0.6 needles/mm$^2$ and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the skin and/or beneath the skin of the subject. The needles may be chosen to have smaller or larger areas (or smaller or large diameters), so long as the area of contact for the needles to the skin is sufficient to allow adequate blood flow from the skin of the subject to the device. For example, in certain embodiments, the needles may be selected to have a combined skin-penetration area of at least about 500 nm$^2$, at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, at least about 300,000 microns$^2$, at least about 500,000 microns$^2$, at least about 800,000 microns$^2$, at least about 8,000,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum penetration into the skin of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound, etc. to assist with the flow of blood from the skin of the subject, or the coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A device for receiving fluid from a subject, comprising:
a device actuator;
a housing including an opening to receive fluid into the housing;
a vacuum source;
a flow path fluidly coupleable to the vacuum source to cause fluid to be drawn into the opening and along the flow path;
a membrane positioned along the flow path downstream of the opening that permits passage of air but prevents passage of liquids; and
one or more needles arranged to be inserted into a subject to cause fluid to be released from the subject.

2. The device of claim 1, wherein actuating the device actuator enables fluid communication between the opening and the vacuum source.

3. The device of claim 2, further comprising a flow control element that prevents fluid communication between the opening and the vacuum source, the flow control element being configured to enable fluid communication between the opening and the vacuum source after actuation of the device actuator.

4. The device of claim 1, further comprising a deployment actuator configured to move the one or more needles in a deployment direction toward or through the opening, in response to actuation of the device actuator.

5. The device of claim 4, wherein the deployment actuator includes a bistable element coupled to the one or more needles, the bistable element being arranged to move from a first stable state to a second stable state in response to actuation of the device actuator, wherein motion of the bistable element from the first stable state to the second stable state moves the one or more needles in a deployment direction toward or through the opening, and wherein the bistable element is incapable of moving from the second stable state to the first stable state in the absence of an external force on the bistable element.

6. The device of claim 4, wherein the device actuator and the deployment actuator are arranged such that actuation of the device actuator causes the one or more needles to reach the subject after fluid communication between the opening and the vacuum source is enabled.

7. The device of claim 1, further comprising a retraction actuator configured to move the one or more needles in a retraction direction away from the opening, in response to actuation of the device actuator.

8. The device of claim 7, wherein the retraction actuator has stored potential energy prior to any deployment movement of the one or more needles.

9. The device of claim 7, wherein the retraction actuator has a pre-deployment state prior to any deployment movement of the one or more needles and a post-retraction state after the retraction actuator has moved the one or more needles in the retraction direction away from the opening, and wherein stored potential energy of the retraction actuator is less in the post-retraction state than in the pre-deployment state.

10. The device of claim 9, wherein a post-retraction distance of the one or more needles from the opening is greater than a post-deployment distance of the one or more needles from the opening.

11. The device of claim 9, wherein the retraction actuator has decreased stored potential energy in the post-retraction state than in the pre-deployment state.

12. The device of claim 8, wherein the stored potential energy increases as the one or more needles move toward a deployment direction toward or through the opening.

13. The device of claim 8, wherein release of the stored potential energy causes movement of the one or more needles in the retraction direction.

14. The device of claim 7, wherein the retraction actuator comprises a spring.

15. The device of claim 1, wherein the flow path comprises a microfluidic channel.

16. The device of claim 1, wherein the vacuum source comprises a vacuum chamber that is at a pressure less than ambient prior to actuation of the device actuator.

17. The device of claim 1, wherein the membrane is positioned along the flow path upstream of the vacuum source.

18. The device of claim 16, further comprising a storage chamber for receiving the fluid, wherein the membrane is positioned along the flow path downstream of the storage chamber and upstream of the vacuum chamber.

19. The device of claim 18, wherein the vacuum chamber is spaced from the storage chamber.

20. The device of claim 16, wherein the housing comprises a covering and base, and wherein the covering defines a portion of the vacuum chamber.

21. A device for receiving fluid from a subject, comprising:
a device actuator;
a housing including an opening to receive fluid into the housing;
a flow path fluidly coupleable to a vacuum source to cause fluid to be drawn into the opening and along the flow path;
a membrane positioned along the flow path downstream of the opening that permits passage of air but prevents passage of liquids; and
one or more needles that are configured to move relative to the housing to insert into a subject and cause fluid to be released from the subject.

22. The device of claim 21, further comprising a deployment actuator configured to move the one or more needles in a deployment direction toward or through the opening in response to actuation of the device actuator.

23. The device of claim 22, wherein the deployment actuator includes a bistable element coupled to the one or more needles, the bistable element being arranged to move from a first stable state to a second stable state in response to actuation of the device actuator, wherein motion of the bistable element from the first stable state to the second stable state moves the one or more needles in a deployment direction toward or through the opening, and wherein the bistable element is incapable of moving from the second stable state to the first stable state in the absence of an external force on the bistable element.

24. The device of claim 21, further comprising a retraction actuator configured to move the one or more needles in a retraction direction away from the opening in response to actuation of the device actuator.

25. The device of claim 24, wherein the retraction actuator has stored potential energy prior to any deployment movement of the one or more needles.

26. The device of claim 24, wherein the retraction actuator has a pre-deployment state prior to any deployment movement of the one or more needles and a post-retraction state after the retraction actuator has moved the one or more needles in the retraction direction away from the opening, and wherein stored potential energy of the retraction actuator is less in the post-retraction state than in the pre-deployment state.

27. The device of claim 26, wherein a post-retraction distance of the one or more needles from the opening is greater than a post-deployment distance of the one or more needles from the opening.

28. The device of claim 26, wherein the retraction actuator has decreased stored potential energy in the post-retraction state than in the pre-deployment state.

29. The device of claim 25, wherein the stored potential energy increases as the one or more needles move toward a deployment direction toward or through the opening.

30. The device of claim 25, wherein release of the stored potential energy causes movement of the one or more needles in the retraction direction.

31. The device of claim 24, wherein the retraction actuator comprises a spring.

32. The device of claim 21, wherein the flow path comprises a microfluidic channel.

* * * * *

UNITED STATES PATENT AND TRADEMARK OFFICE
CERTIFICATE OF CORRECTION

PATENT NO. : 10,799,166 B2
APPLICATION NO. : 15/634354
DATED : October 13, 2020
INVENTOR(S) : Javier Gonzalez-Zugasti et al.

It is certified that error appears in the above-identified patent and that said Letters Patent is hereby corrected as shown below:

On the Title Page

Item (63) should read:
(63) Continuation of application No. 14/328,892, filed on Jul. 11. 2014, now Pat. No. 9,730,624, which is a continuation of application No. 13/680,351, filed on Nov. 19, 2012, now Pat. No. 8,821,412, which is a continuation-in-part of application No. 13/456,570, filed on Apr. 26, 2012, now Pat. No. 8,827,971, said application No. 13/680,351 is a continuation-in-part of application No. 13/456,394, filed on Apr. 26, 2012, now Pat. No. 9,295,417, said application No. 13/680,351 is a continuation-in-part of application No. 13/456,505, filed on Apr. 26, 2012, now Pat. No. 9,119,578, said application No. 13/680,351 is a continuation-in-part of application No. 13/456,546, filed on Apr. 26, 2012, now abandoned, said application No. 13/680,351 is a continuation-in-part of application No. PCT/US2011/047565, filed on Aug. 12, 2011, said application No. 13/680,351 is a continuation-in-part of application No. PCT/US2011/043698, filed on Jul. 12, 2011, said application No. 13/680,351 is a continuation-in-part of application No. 13/166,451, filed on Jun. 22, 2011, now Pat. No. 9,033,898, said application No. 13/680,351 is a continuation-in-part of application No. 13/016,575, filed on Jan. 28, 2011, now Pat. No. 9,041,541, said application No. 13/680,351 is a continuation-in-part of application No. 13/006,165, filed on Jan. 13, 2011, now abandoned, said Signed and Sealed this
Twelfth Day of January, 2021

Andrei Iancu
*Director of the United States Patent and Trademark Office* application No. 13/680,351 is a continuation-in-part of application No. 13/006,177, filed on Jan. 13, 2011, now abandoned, said application No. 13/680,351 is a continuation-in-part of application No. 12/953,744, filed on Nov. 24, 2010, now abandoned, said application No. 13/680,351 is a continuation-in-part of application No. 12/915,735, filed on Oct. 29, 2010, now abandoned, said application No. 13/680,351 is a continuation-in-part of application No. 12/915,789, filed on Oct. 29, 2010, now abandoned, said application No. 13/680,351 is a continuation-in-part of application No. 12/915,820, filed on Oct. 29, 2010, now abandoned, said application No. 13/680,351 is a continuation-in-part of application No. 12/716,229, filed on Mar. 2, 2010, now Pat. No. 9,113,836, said application No. 13/680,351 is a continuation-in-part of application No. 12/716,226, filed on Mar. 2, 2010, now abandoned.

In the Claims

Column 34, Lines 29-32, Claim 4 should read:
4. The device of claim 1, further comprising a deployment actuator configured to move the one or more needles in a deployment direction toward or through the opening in response to actuation of the device actuator.

Column 34, Lines 49-52, Claim 7 should read:
7. The device of claim 1, further comprising a retraction actuator configured to move the one or more needles in a retraction direction away from the opening in response to actuation of the device actuator.